US005422110A

United States Patent [19]

Potter et al.

[11] Patent Number: 5,422,110

[45] Date of Patent: Jun. 6, 1995

[54] ENHANCED IMMUNOGENICITY USING LEUKOTOXIN CHIMERAS

[75] Inventors: Andrew A. Potter; Mark J. Redmond; Huw P. A. Hughes, all of Saskatchewan, Canada

[73] Assignee: University of Saskatchewan, Saskatoon, Canada

[21] Appl. No.: 960,932

[22] Filed: Oct. 14, 1992

Related U.S. Application Data

[63] Continuation-in-part of Ser. No. 779,171, Oct. 16, 1991, abandoned.

[51] Int. Cl.[6] ...................... A61K 39/102; C12N 15/31

[52] U.S. Cl. .............................. 424/255.1; 424/184.1; 424/190.1; 424/192.1; 424/234.1; 530/350; 530/825; 435/69.3; 435/172.1; 435/172.3; 435/69.1; 536/23.4; 536/23.7

[58] Field of Search .................. 530/350, 825; 424/88, 424/92, 184.1, 190.1, 192.1, 234.1, 255.1; 435/69.3, 172.1, 172.3, 69.7; 536/23.4, 23.7; 935/13, 47

[56] References Cited

U.S. PATENT DOCUMENTS

| | | | |
|---|---|---|---|
| 4,722,840 | 2/1988 | Valenzuela et al. . | |
| 4,867,973 | 9/1989 | Goers et al. | 424/85.91 |
| 4,957,739 | 9/1990 | Berget et al. | 424/92 |
| 4,975,420 | 12/1990 | Silversides et al. | 514/15 |
| 5,028,423 | 7/1991 | Prickett . | |
| 5,055,400 | 10/1991 | Lo et al. . | |
| 5,238,823 | 8/1993 | Potter et al. | 435/69.52 |

FOREIGN PATENT DOCUMENTS

| | | |
|---|---|---|
| WO90/10458 | 9/1990 | WIPO . |
| WO91/15237 | 10/1991 | WIPO . |
| WO92/03558 | 3/1992 | WIPO . |

OTHER PUBLICATIONS

Phalipin, A. et al. Gene 55:255–263 (1987).
Buggemann, P. et al BioTechniques 10(2):202–209 (1991).
Forestier, C. et al. 1991. Infection and Immunity 59(11):4212–4220.
Sad, S. et al. 1991. Immunology 74:223–227.
Que et al. 1988. Infection & Immunity 56(10):2645–2649.
Bittle et al., *Nature* (1982) 298:30–33.
Muller et al., *Proc. Natl. Acad. Sci.* (1982) 79:569–573.
Schutze et al., *J. Immunol.* (1985) 135(4):2319–2322.
Lowell et al., *Science* (1988) 240:800–802.
Morein et al., *Nature* (1984) 308:457–460.
Neurath et al., *Mol. Immunol.* (1989) 26(1):53–62.
Redmond et al., *Mol. Immunol.* (1991) 28(3):269–278.
Kingsman and Kingsman, *Vaccine* (1988) 6:304–306.
Valenzuela et al., *Bio/Technology* (1985) 3:323–326.
Delpeyroux et al., *Science* (1986) 233:472–475.
Clarke et al., *Vaccines 88* Ginsberg, H., et al., Eds., (1988) pp. 127–131.
Burke et al., *Nature* (1988) 332:81–82.
Haynes et al., *Bio/Technology* (1986) 4:637–641.
Gentry et al., *Vet. Immunology and Immunopathology* (1985) 9:239–250.
Strathdee and Lo, *Infect. Immun.* (1987) 55(12):3233–3236.
Lo et al., *Infect. Immun.* (1985) 50(3):667–671.

*Primary Examiner*—Hazel F. Sidberry
*Assistant Examiner*—Michael S. Tuscan
*Attorney, Agent, or Firm*—Reed & Robins

[57] ABSTRACT

New immunological carrier systems, DNA encoding the same, and the use of these systems, are disclosed. The carrier systems include chimeric proteins which comprise a leukotoxin polypeptide fused to a selected antigen. The leukotoxin functions to increase the immunogenicity of the antigen fused thereto.

12 Claims, 45 Drawing Sheets

Figure 3-1

```
        10         20         30         40         50         60         70         80         90
  *     *     *     *     *     *     *     *     *     *     *     *     *     *     *     *     *     *
ATG GCT ACT GTT ATA GAT CTA AGC TTC CCA AAA ACT GGG GCA AAA AAA ATT ATC CTC TAT ATT CCC CAA AAT TAC CAA TAT GAT ACT GAA
TAC CGA TGA CAA TAT CTA GAT TCG AAG GGT TTT TGA CCC CGT TTT TTT TAA TAG GAG ATA TAA GGG GTT TTA ATG GTT ATA CTA TGA CTT
Met Ala Thr Val Ile Asp Leu Ser Phe Pro Lys Thr Gly Ala Lys Lys Ile Ile Leu Tyr Ile Pro Gln Asn Tyr Gln Tyr Asp Thr Glu>
___c___c___c___c___c___c___c___c___c___c____RECOMBINANT LEUKOTOXIN PEPTIDE_c___c___c___c___c___c___c___c___c___c___c___>
___a___a___VECTOR SEQUENCE_a___a___a__>

        100        110        120        130        140        150        160        170        180
  *     *     *     *     *     *     *     *     *     *     *     *     *     *     *     *     *     *
CAA GGT AAT GGT TTA CAG GAT TTA GTC AAA GCG GCC GAA GAG TTG GGG ATT GAG GTA CAA AGA GAA GAA CGC AAT AAT ATT GCA ACA GCT
GTT CCA TTA CCA AAT GTC CTA AAT CAG TTT CGC CGG CTT CTC AAC CCC TAA CTC CAT GTT TCT CTT CTT GCG TTA TTA TAA CGT TGT CGA
Gln Gly Asn Gly Leu Gln Asp Leu Val Lys Ala Ala Glu Glu Leu Gly Ile Glu Val Gln Arg Glu Glu Arg Asn Asn Ile Ala Thr Ala>
___c___c___c___c___c___c___c___c___c___c____RECOMBINANT LEUKOTOXIN PEPTIDE_c___c___c___c___c___c___c___c___c___c___c___>

        190        200        210        220        230        240        250        260        270
  *     *     *     *     *     *     *     *     *     *     *     *     *     *     *     *     *     *
CAA ACC AGT TTA GGC ACG ATT CAA ACC GCT ATT GGC TTA ACT GAG CGT GGC ATT GTG TTA TCC GCT CCA CAA ATT GAT AAA TTG CTA CAG
GTT TGG TCA AAT CCG TGC TAA GTT TGG CGA TAA CCG AAT TGA CTC GCA CCG TAA CAC AAT AGG CGA GGT GTT TAA CTA TTT AAC GAT GTC
Gln Thr Ser Leu Gly Thr Ile Gln Thr Ala Ile Gly Leu Thr Glu Arg Gly Ile Val Leu Ser Ala Pro Gln Ile Asp Lys Leu Leu Gln>
___c___c___c___c___c___c___c___c___c___c____RECOMBINANT LEUKOTOXIN PEPTIDE_c___c___c___c___c___c___c___c___c___c___c___>
```

Figure 3-2

```
         280       290       300       310       320       330       340       350       360
      *   *   *   *   *   *   *   *   *   *   *   *   *   *   *   *   *   *
AAA ACT AAA GCA GGC CAA GCA TTA GGT TCT GCC GAA AGC ATT GTA CAA AAT GCA AAT AAA GCC AAA ACT GTA TTA TCT GGC ATT CAA TCT
TTT TGA TTT CGT CCG GTT CGT AAT CCA AGA CGG CTT TCG TAA CAT GTT TTA CGT TTA TTT CGG TTT TGA CAT AAT AGA CCG TAA GTT AGA
Lys Thr Lys Ala Gly Gln Ala Leu Gly Ser Ala Glu Ser Ile Val Gln Asn Ala Asn Lys Ala Lys Thr Val Leu Ser Gly Ile Gln Ser>
___c___c___c___c___c___c___c___c___c___c____RECOMBINANT LEUKOTOXIN PEPTIDE_c___c___c___c___c___c___c___c___c___c___c___>

         370       380       390       400       410       420       430       440       450
      *   *   *   *   *   *   *   *   *   *   *   *   *   *   *   *   *   *
ATT TTA GGC TCA GTA TTG GCT GGA ATG GAT TTA GAT GAG GCC TTA CAG AAT AAC AGC AAC CAA CAT GCT CTT GCT AAA GCT GGC TTG GAG
TAA AAT CCG AGT CAT AAC CGA CCT TAC CTA AAT CTA CTC CGG AAT GTC TTA TTG TCG TTG GTT GTA CGA GAA CGA TTT CGA CCG AAC CTC
Ile Leu Gly Ser Val Leu Ala Gly Met Asp Leu Asp Glu Ala Leu Gln Asn Asn Ser Asn Gln His Ala Leu Ala Lys Ala Gly Leu Glu>
___c___c___c___c___c___c___c___c___c___c____RECOMBINANT LEUKOTOXIN PEPTIDE_c___c___c___c___c___c___c___c___c___c___c___>

         460       470       480       490       500       510       520       530       540
      *   *   *   *   *   *   *   *   *   *   *   *   *   *   *   *   *   *
CTA ACA AAT TCA TTA ATT GAA AAT ATT GCT AAT TCA GTA AAA ACA CTT GAC GAA TTT GGT GAG CAA ATT AGT CAA TTT GGT TCA AAA CTA
GAT TGT TTA AGT AAT TAA CTT TTA TAA CGA TTA AGT CAT TTT TGT GAA CTG CTT AAA CCA CTC GTT TAA TCA GTT AAA CCA AGT TTT GAT
Leu Thr Asn Ser Leu Ile Glu Asn Ile Ala Asn Ser Val Lys Thr Leu Asp Glu Phe Gly Glu Gln Ile Ser Gln Phe Gly Ser Lys Leu>
___c___c___c___c___c___c___c___c___c___c____RECOMBINANT LEUKOTOXIN REPTIDE_c___c___c___c___c___c___c___c___c___c___c___>

         550       560       570       580       590       600       610       620       630
      *   *   *   *   *   *   *   *   *   *   *   *   *   *   *   *   *   *
CAA AAT ATC AAA GGC TTA GGG ACT TTA GGA GAC AAA CTC AAA AAT ATC GGT GGA CTT GAT AAA GCT GGC CTT GGT TTA GAT GTT ATC TCA
GTT TTA TAG TTT CCG AAT CCC TGA AAT CCT CTG TTT GAG TTT TTA TAG CCA CCT GAA CTA TTT CGA CCG GAA CCA AAT CTA CAA TAG AGT
Gln Asn Ile Lys Gly Leu Gly Thr Leu Gly Asp Lys Leu Lys Asn Ile Gly Gly Leu Asp Lys Ala Gly Leu Gly Leu Asp Val Ile Ser>
___c___c___c___c___c___c___c___c___c___c____RECOMBINANT LEUKOTOXIN PEPTIDE_c___c___c___c___c___c___c___c___c___c___c___>
```

Figure 3-3

```
        640         650         660         670         680         690         700         710         720
  *     *     *     *     *     *     *     *     *     *     *     *     *     *     *     *     *     *
GGG CTA TTA TCG GGC GCA ACA GCT GCA CTT GTA CTT GCA GAT AAA AAT GCT TCA ACA GCT AAA AAA GTG GGT GCG GGT TTT GAA TTG GCA
CCC GAT AAT AGC CCG CGT TGT CGA CGT GAA CAT GAA CGT CTA TTT TTA CGA AGT TGT CGA TTT TTT CAC CCA CGC CCA AAA CTT AAC CGT
Gly Leu Leu Ser Gly Ala Thr Ala Ala Leu Val Leu Ala Asp Lys Asn Ala Ser Thr Ala Lys Lys Val Gly Ala Gly Phe Glu Leu Ala>
___c___c___c___c___c___c___c___c___c___c____RECOMBINANT LEUKOTOXIN PEPTIDE_c___c___c___c___c___c___c___c___c___c___c___>

        730         740         750         760         770         780         790         800         810
  *     *     *     *     *     *     *     *     *     *     *     *     *     *     *     *     *     *
AAC CAA GTT GTT GGT AAT ATT ACC AAA GCC GTT TCT TCT TAC ATT TTA GCC CAA CGT GTT GCA GCA GGT TTA TCT TCA ACT GGG CCT GTG
TTG GTT CAA CAA CCA TTA TAA TGG TTT CGG CAA AGA AGA ATG TAA AAT CGG GTT GCA CAA CGT CGT CCA AAT AGA AGT TGA CCC GGA CAC
Asn Gln Val Val Gly Asn Ile Thr Lys Ala Val Ser Ser Tyr Ile Leu Ala Gln Arg Val Ala Ala Gly Leu Ser Ser Thr Gly Pro Val>
___c___c___c___c___c___c___c___c___c___c____RECOMBINANT LEUKOTOXIN PEPTIDE_c___c___c___c___c___c___c___c___c___c___c___>

        820         830         840         850         860         870         880         890         900
  *     *     *     *     *     *     *     *     *     *     *     *     *     *     *     *     *     *
GCT GCT TTA ATT GCT TCT ACT GTT TCT CTT GCG ATT AGC CCA TTA GCA TTT GCC GGT ATT GCC GAT AAA TTT AAT CAT GCA AAA AGT TTA
CGA CGA AAT TAA CGA AGA TGA CAA AGA GAA CGC TAA TCG GGT AAT CGT AAA CGG CCA TAA CGG CTA TTT AAA TTA GTA CGT TTT TCA AAT
Ala Ala Leu Ile Ala Ser Thr Val Ser Leu Ala Ile Ser Pro Leu Ala Phe Ala Gly Ile Ala Asp Lys Phe Asn His Ala Lys Ser Leu>
___c___c___c___c___c___c___c___c___c___c____RECOMBINANT LEUKOTOXIN PEPTIDE_c___c___c___c___c___c___c___c___c___c___c___>
```

Figure 3-4

```
        910         920         930         940         950         960         970         980         990
     *     *     *     *     *     *     *     *     *     *     *     *     *     *     *     *     *     *
GAG AGT TAT GCC GAA CGC TTT AAA AAA TTA GGC TAT GAC GGA GAT AAT TTA TTA GCA GAA TAT CAG CGG GGA ACA GGG ACT ATT GAT GCA
CTC TCA ATA CGG CTT GCG AAA TTT TTT AAT CCG ATA CTG CCT CTA TTA AAT AAT CGT CTT ATA GTC GCC CCT TGT CCC TGA TAA CTA CGT
Glu Ser Tyr Ala Glu Arg Phe Lys Lys Leu Gly Tyr Asp Gly Asp Asn Leu Leu Ala Glu Tyr Gln Arg Gly Thr Gly Thr Ile Asp Ala>
___c___c___c___c___c___c___c___c___c___c____RECOMBINANT LEUKOTOXIN PEPTIDE_c___c___c___c___c___c___c___c___c___c___c___>

       1000        1010        1020        1030        1040        1050        1060        1070        1080
     *     *     *     *     *     *     *     *     *     *     *     *     *     *     *     *     *     *
TCG GTT ACT GCA ATT AAT ACC GCA TTG GCC GCT ATT GCT GGT GGT GTG TCT GCT GCT GCA GCC GGC TCG GTT ATT GCT TCA CCG ATT GCC
AGC CAA TGA CGT TAA TTA TGG CGT AAC CGG CGA TAA CGA CCA CCA CAC AGA CGA CGA CGT CGG CCG AGC CAA TAA CGA AGT GGC TAA CGG
Ser Val Thr Ala Ile Asn Thr Ala Leu Ala Ala Ile Ala Gly Gly Val Ser Ala Ala Ala Ala Gly Ser Val Ile Ala Ser Pro Ile Ala>
___c___c___c___c___c___c___c___c___c___c____RECOMBINANT LEUKOTOXIN PEPTIDE_c___c___c___c___c___c___c___c___c___c___c___>

       1090        1100        1110        1120        1130        1140        1150        1160        1170
     *     *     *     *     *     *     *     *     *     *     *     *     *     *     *     *     *     *
TTA TTA GTA TCT GGG ATT ACC GGT GTA ATT TCT ACG ATT CTG CAA TAT TCT AAA CAA GCA ATG TTT GAG CAC GTT GCA AAT AAA ATT CAT
AAT AAT CAT AGA CCC TAA TGG CCA CAT TAA AGA TGC TAA GAC GTT ATA AGA TTT GTT CGT TAC AAA CTC GTG CAA CGT TTA TTT TAA GTA
Leu Leu Val Ser Gly Ile Thr Gly Val Ile Ser Thr Ile Leu Gln Tyr Ser Lys Gln Ala Met Phe Glu His Val Ala Asn Lys Ile His>
___c___c___c___c___c___c___c___c___c___c____RECOMBINANT LEUKOTOXIN PEPTIDE_c___c___c___c___c___c___c___c___c___c___c___>

       1180        1190        1200        1210        1220        1230        1240        1250        1260
     *     *     *     *     *     *     *     *     *     *     *     *     *     *     *     *     *     *
AAC AAA ATT GTA GAA TGG GAA AAA AAT AAT CAC GGT AAG AAC TAC TTT GAA AAT GGT TAC GAT GCC CGT TAT CTT GCG AAT TTA CAA GAT
TTG TTT TAA CAT CTT ACC CTT TTT TTA TTA GTG CCA TTC TTG ATG AAA CTT TTA CCA ATG CTA CGG GCA ATA GAA CGC TTA AAT GTT CTA
Asn Lys Ile Val Glu Trp Glu Lys Asn Asn His Gly Lys Asn Tyr Phe Glu Asn Gly Tyr Asp Ala Arg Tyr Leu Ala Asn Leu Gln Asp>
___c___c___c___c___c___c___c___c___c___c____RECOMBINANT LEUKOTOXIN PEPTIDE_c___c___c___c___c___c___c___c___c___c___c___>
```

Figure 3-5

```
          1270            1280            1290             1300             1310             1320             1330             1340            1350
       *       *       *       *       *       *       *       *       *       *       *       *       *       *       *       *       *       *
AAT ATG AAA TTC TTA CTG AAC TTA AAC AAA GAG TTA CAG GCA GAA CGT GTC ATC GCT ATT ACT CAG CAG CAA TGG GAT AAC AAC ATT GGT
TTA TAC TTT AAG AAT GAC TTG AAT TTG TTT CTC AAT GTC CGT CTT GCA CAG TAG CGA TAA TGA GTC GTC GTT ACC CTA TTG TTG TAA CCA
Asn Met Lys Phe Leu Leu Asn Leu Asn Lys Glu Leu Gln Ala Glu Arg Val Ile Ala Ile Thr Gln Gln Gln Trp Asp Asn Asn Ile Gly>
___c___c___c___c___c___c___c___c___c___c____RECOMBINANT LEUKOTOXIN PEPTIDE_c___c___c___c___c___c___c___c___c___c___c___>

          1360            1370            1380             1390             1400             1410             1420             1430            1440
       *       *       *       *       *       *       *       *       *       *       *       *       *       *       *       *       *       *
GAT TTA GCT GGT ATT AGC CGT TTA GGT GAA AAA GTC CTT AGT GGT AAA GCC TAT GTG GAT GCG TTT GAA GAA GGC AAA CAC ATT AAA GCC
CTA AAT CGA CCA TAA TCG GCA AAT CCA CTT TTT CAG GAA TCA CCA TTT CGG ATA CAC CTA CGC AAA CTT CTT CCG TTT GTG TAA TTT CGG
Asp Leu Ala Gly Ile Ser Arg Leu Gly Glu Lys Val Leu Ser Gly Lys Ala Tyr Val Asp Ala Phe Glu Glu Gly Lys His Ile Lys Ala>
___c___c___c___c___c___c___c___c___c___c____RECOMBINANT LEUKOTOXIN PEPTIDE_c___c___c___c___c___c___c___c___c___c___c___>

          1450            1460            1470             1480             1490             1500             1510             1520            1530
       *       *       *       *       *       *       *       *       *       *       *       *       *       *       *       *       *       *
GAT AAA TTA GTA CAG TTG GAT TCG GCA AAC GGT ATT ATT GAT GTG AGT AAT TCG GGT AAA GCG AAA ACT CAG CAT ATC TTA TTC AGA ACG
CTA TTT AAT CAT GTC AAC CTA AGC CGT TTG CCA TAA TAA CTA CAC TCA TTA AGC CCA TTT CGC TTT TGA GTC GTA TAG AAT AAG TCT TGC
Asp Lys Leu Val Gln Leu Asp Ser Ala Asn Gly Ile Ile Asp Val Ser Asn Ser Gly Lys Ala Lys Thr Gln His Ile Leu Phe Arg Thr>
___c___c___c___c___c___c___c___c___c___c____RECOMBINANT LEUKOTOXIN PEPTIDE_c___c___c___c___c___c___c___c___c___c___c___>
```

Figure 3-6

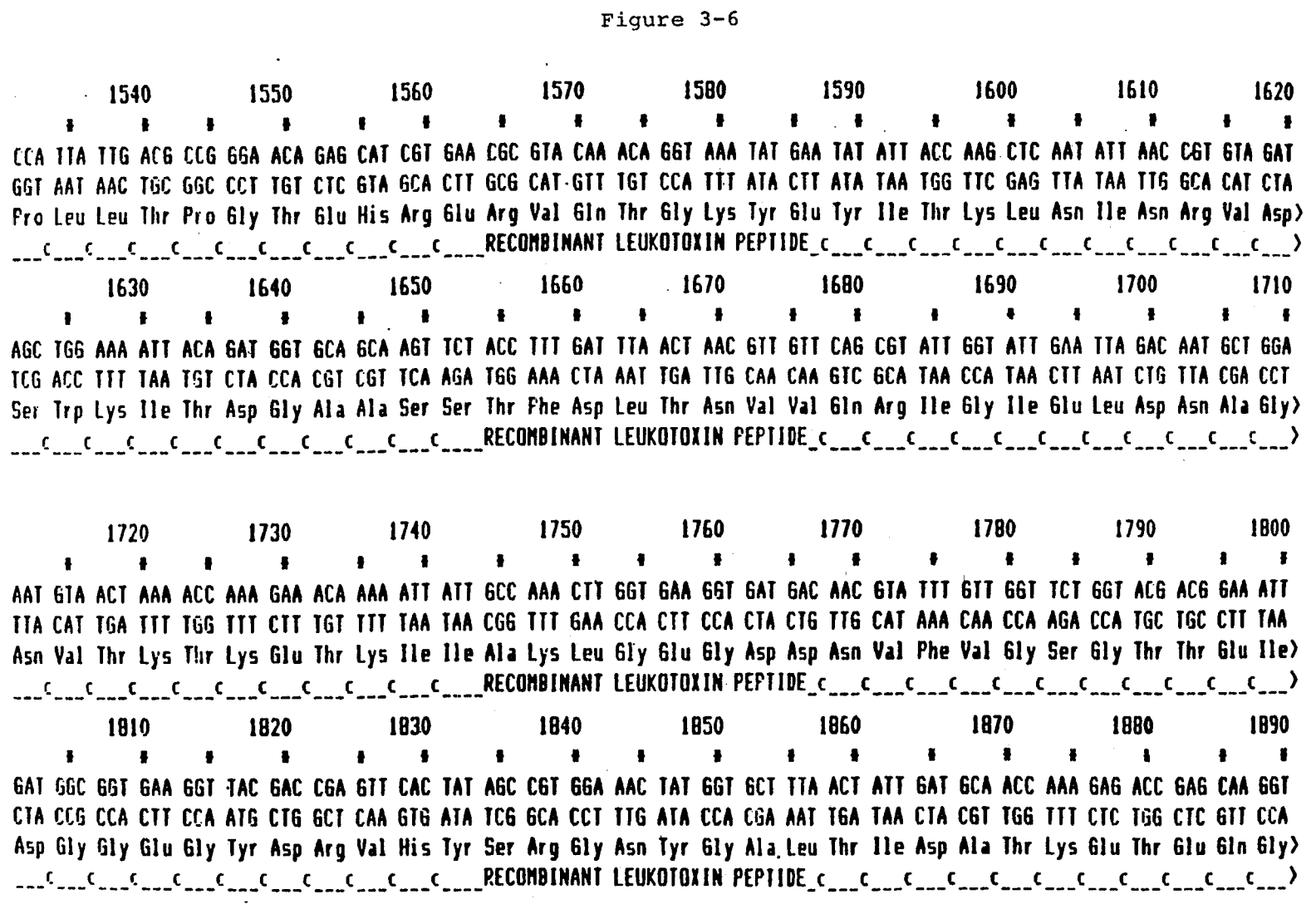

```
       1540      1550      1560      1570      1580      1590      1600      1610      1620
CCA TTA TTG ACG CCG GGA ACA GAG CAT CGT GAA CGC GTA CAA ACA GGT AAA TAT GAA TAT ATT ACC AAG CTC AAT ATT AAC CGT GTA GAT
GGT AAT AAC TGC GGC CCT TGT CTC GTA GCA CTT GCG CAT GTT TGT CCA TTT ATA CTT ATA TAA TGG TTC GAG TTA TAA TTG GCA CAT CTA
Pro Leu Leu Thr Pro Gly Thr Glu His Arg Glu Arg Val Gln Thr Gly Lys Tyr Glu Tyr Ile Thr Lys Leu Asn Ile Asn Arg Val Asp>
___c___c___c___c___c___c___c___c___c___c___RECOMBINANT LEUKOTOXIN PEPTIDE_c___c___c___c___c___c___c___c___c___c___c___>

       1630      1640      1650      1660      1670      1680      1690      1700      1710
AGC TGG AAA ATT ACA GAT GGT GCA GCA AGT TCT ACC TTT GAT TTA ACT AAC GTT GTT CAG CGT ATT GGT ATT GAA TTA GAC AAT GCT GGA
TCG ACC TTT TAA TGT CTA CCA CGT CGT TCA AGA TGG AAA CTA AAT TGA TTG CAA CAA GTC GCA TAA CCA TAA CTT AAT CTG TTA CGA CCT
Ser Trp Lys Ile Thr Asp Gly Ala Ala Ser Ser Thr Phe Asp Leu Thr Asn Val Val Gln Arg Ile Gly Ile Glu Leu Asp Asn Ala Gly>
___c___c___c___c___c___c___c___c___c___c___RECOMBINANT LEUKOTOXIN PEPTIDE_c___c___c___c___c___c___c___c___c___c___c___>

       1720      1730      1740      1750      1760      1770      1780      1790      1800
AAT GTA ACT AAA ACC AAA GAA ACA AAA ATT ATT GCC AAA CTT GGT GAA GGT GAT GAC AAC GTA TTT GTT GGT TCT GGT ACG ACG GAA ATT
TTA CAT TGA TTT TGG TTT CTT TGT TTT TAA TAA CGG TTT GAA CCA CTT CCA CTA CTG TTG CAT AAA CAA CCA AGA CCA TGC TGC CTT TAA
Asn Val Thr Lys Thr Lys Glu Thr Lys Ile Ile Ala Lys Leu Gly Glu Gly Asp Asp Asn Val Phe Val Gly Ser Gly Thr Thr Glu Ile>
___c___c___c___c___c___c___c___c___c___c___RECOMBINANT LEUKOTOXIN PEPTIDE_c___c___c___c___c___c___c___c___c___c___c___>

       1810      1820      1830      1840      1850      1860      1870      1880      1890
GAT GGC GGT GAA GGT TAC GAC CGA GTT CAC TAT AGC CGT GGA AAC TAT GGT GCT TTA ACT ATT GAT GCA ACC AAA GAG ACC GAG CAA GGT
CTA CCG CCA CTT CCA ATG CTG GCT CAA GTG ATA TCG GCA CCT TTG ATA CCA CGA AAT TGA TAA CTA CGT TGG TTT CTC TGG CTC GTT CCA
Asp Gly Gly Glu Gly Tyr Asp Arg Val His Tyr Ser Arg Gly Asn Tyr Gly Ala Leu Thr Ile Asp Ala Thr Lys Glu Thr Glu Gln Gly>
___c___c___c___c___c___c___c___c___c___c___RECOMBINANT LEUKOTOXIN PEPTIDE_c___c___c___c___c___c___c___c___c___c___c___>
```

Figure 3-7

```
       1900      1910      1920      1930      1940      1950      1960      1970      1980
         *    *    *    *    *    *    *    *    *    *    *    *    *    *    *    *    *    *
AGT TAT ACC GTA AAT CGT TTC GTA GAA ACC GGT AAA GCA CTA CAC GAA GTG ACT TCA ACC CAT ACC GCA TTA GTG GGC AAC CGT GAA GAA
TCA ATA TGG CAT TTA GCA AAG CAT CTT TGG CCA TTT CGT GAT GTG CTT CAC TGA AGT TGG GTA TGG CGT AAT CAC CCG TTG GCA CTT CTT
Ser Tyr Thr Val Asn Arg Phe Val Glu Thr Gly Lys Ala Leu His Glu Val Thr Ser Thr His Thr Ala Leu Val Gly Asn Arg Glu Glu>
___c___c___c___c___c___c___c___c___c___c____RECOMBINANT LEUKOTOXIN PEPTIDE_c___c___c___c___c___c___c___c___c___c___c___>

       1990      2000      2010      2020      2030      2040      2050      2060      2070
         *    *    *    *    *    *    *    *    *    *    *    *    *    *    *    *    *    *
AAA ATA GAA TAT CGT CAT AGC AAT AAC CAG CAC CAT GCC GGT TAT TAC ACC AAA GAT ACC TTG AAA GCT GTT GAA GAA ATT ATC GGT ACA
TTT TAT CTT ATA GCA GTA TCG TTA TTG GTC GTG GTA CGG CCA ATA ATG TGG TTT CTA TGG AAC TTT CGA CAA CTT CTT TAA TAG CCA TGT
Lys Ile Glu Tyr Arg His Ser Asn Asn Gln His His Ala Gly Tyr Tyr Thr Lys Asp Thr Leu Lys Ala Val Glu Glu Ile Ile Gly Thr>
___c___c___c___c___c___c___c___c___c___c____RECOMBINANT LEUKOTOXIN PEPTIDE_c___c___c___c___c___c___c___c___c___c___c___>

       2080      2090      2100      2110      2120      2130      2140      2150      2160
         *    *    *    *    *    *    *    *    *    *    *    *    *    *    *    *    *    *
TCA CAT AAC GAT ATC TTT AAA GGT AGT AAG TTC AAT GAT GCC TTT AAC GGT GGT GAT GGT GTC GAT ACT ATT GAC GGT AAC GAC GGC AAT
AGT GTA TTG CTA TAG AAA TTT CCA TCA TTC AAG TTA CTA CGG AAA TTG CCA CCA CTA CCA CAG CTA TGA TAA CTG CCA TTG CTG CCG TTA
Ser His Asn Asp Ile Phe Lys Gly Ser Lys Phe Asn Asp Ala Phe Asn Gly Gly Asp Gly Val Asp Thr Ile Asp Gly Asn Asp Gly Asn>
___c___c___c___c___c___c___c___c___c___c____RECOMBINANT LEUKOTOXIN PEPTIDE_c___c___c___c___c___c___c___c___c___c___c___>
```

Figure 3-8

```
        2170      2180      2190      2200      2210      2220      2230      2240      2250
         *    *    *    *    *    *    *    *    *    *    *    *    *    *    *    *    *    *
GAC CGC TTA TTT GGT GGT AAA GGC GAT GAT ATT CTC GAT GGT GGA AAT GGT GAT GAT TTT ATC GAT GGC GGT AAA GGC AAC GAC CTA TTA
CTG GCG AAT AAA CCA CCA TTT CCG CTA CTA TAA GAG CTA CCA CCT TTA CCA CTA CTA AAA TAG CTA CCG CCA TTT CCG TTG CTG GAT AAT
Asp Arg Leu Phe Gly Gly Lys Gly Asp Asp Ile Leu Asp Gly Gly Asn Gly Asp Asp Phe Ile Asp Gly Gly Lys Gly Asn Asp Leu Leu>
___c___c___c___c___c___c___c___c___c___c____RECOMBINANT LEUKOTOXIN PEPTIDE_c___c___c___c___c___c___c___c___c___c___c___>

        2260      2270      2280      2290      2300      2310      2320      2330      2340
         *    *    *    *    *    *    *    *    *    *    *    *    *    *    *    *    *    *
CAC GGT GGC AAG GGC GAT GAT ATT TTC GTT CAC CGT AAA GGC GAT GGT AAT GAT ATT ATT ACC GAT TCT GAC GGC AAT GAT AAA TTA TCA
GTG CCA CCG TTC CCG CTA CTA TAA AAG CAA GTG GCA TTT CCG CTA CCA TTA CTA TAA TAA TGG CTA AGA CTG CCG TTA CTA TTT AAT AGT
His Gly Gly Lys Gly Asp Asp Ile Phe Val His Arg Lys Gly Asp Gly Asn Asp Ile Ile Thr Asp Ser Asp Gly Asn Asp Lys Leu Ser>
___c___c___c___c___c___c___c___c___c___c____RECOMBINANT LEUKOTOXIN PEPTIDE_c___c___c___c___c___c___c___c___c___c___c___>

        2350      2360      2370      2380      2390      2400      2410      2420      2430
         *    *    *    *    *    *    *    *    *    *    *    *    *    *    *    *    *    *
TTC TCT GAT TCG AAC TTA AAA GAT TTA ACA TTT GAA AAA GTT AAA CAT AAT CTT GTC ATC ACG AAT AGC AAA AAA GAG AAA GTG ACC ATT
AAG AGA CTA AGC TTG AAT TTT CTA AAT TGT AAA CTT TTT CAA TTT GTA TTA GAA CAG TAG TGC TTA TCG TTT TTT CTC TTT CAC TGG TAA
Phe Ser Asp Ser Asn Leu Lys Asp Leu Thr Phe Glu Lys Val Lys His Asn Leu Val Ile Thr Asn Ser Lys Lys Glu Lys Val Thr Ile>
___c___c___c___c___c___c___c___c___c___c____RECOMBINANT LEUKOTOXIN PEPTIDE_c___c___c___c___c___c___c___c___c___c___c___>

        2440      2450      2460      2470      2480      2490      2500      2510      2520
         *    *    *    *    *    *    *    *    *    *    *    *    *    *    *    *    *    *
CAA AAC TGG TTC CGA GAG GCT GAT TTT GCT AAA GAA GTG CCT AAT TAT AAA GCA ACT AAA GAT GAG AAA ATC GAA GAA ATC ATC GGT CAA
GTT TTG ACC AAG GCT CTC CGA CTA AAA CGA TTT CTT CAC GGA TTA ATA TTT CGT TGA TTT CTA CTC TTT TAG CTT CTT TAG TAG CCA GTT
Gln Asn Trp Phe Arg Glu Ala Asp Phe Ala Lys Glu Val Pro Asn Tyr Lys Ala Thr Lys Asp Glu Lys Ile Glu Glu Ile Ile Gly Gln>
___c___c___c___c___c___c___c___c___c___c____RECOMBINANT LEUKOTOXIN PEPTIDE_c___c___c___c___c___c___c___c___c___c___c___>
```

Figure 3-9

```
       2530      2540      2550      2560      2570      2580      2590      2600      2610
        *    *    *    *    *    *    *    *    *    *    *    *    *    *    *    *    *    *
AAT GGC GAG CGG ATC ACC TCA AAG CAA GTT GAT GAT CTT ATC GCA AAA GGT AAC GGC AAA ATT ACC CAA GAT GAG CTA TCA AAA GTT GTT
TTA CCG CTC GCC TAG TGG AGT TTC GTT CAA CTA CTA GAA TAG CGT TTT CCA TTG CCG TTT TAA TGG GTT CTA CTC GAT AGT TTT CAA CAA
Asn Gly Glu Arg Ile Thr Ser Lys Gln Val Asp Asp Leu Ile Ala Lys Gly Asn Gly Lys Ile Thr Gln Asp Glu Leu Ser Lys Val Val>
___c___c___c___c___c___c___c___c___c___c____RECOMBINANT LEUKOTOXIN PEPTIDE_c___c___c___c___c___c___c___c___c___c___c___>

       2620      2630      2640      2650      2660      2670      2680      2690      2700
        *    *    *    *    *    *    *    *    *    *    *    *    *    *    *    *    *    *
GAT AAC TAT GAA TTG CTC AAA CAT AGC AAA AAT GTG ACA AAC AGC TTA GAT AAG TTA ATC TCA TCT GTA AGT GCA TTT ACC TCG TCT AAT
CTA TTG ATA CTT AAC GAG TTT GTA TCG TTT TTA CAC TGT TTG TCG AAT CTA TTC AAT TAG AGT AGA CAT TCA CGT AAA TGG AGC AGA TTA
Asp Asn Tyr Glu Leu Leu Lys His Ser Lys Asn Val Thr Asn Ser Leu Asp Lys Leu Ile Ser Ser Val Ser Ala Phe Thr Ser Ser Asn>
___c___c___c___c___c___c___c___c___c___c____RECOMBINANT LEUKOTOXIN PEPTIDE_c___c___c___c___c___c___c___c___c___c___c___>

       2710      2720      2730      2740      2750      2760      2770      2780    2790
        *    *    *    *    *    *    *    *    *    *    *    *    *    *    *    *    *    *
GAT TCG AGA AAT GTA TTA GTG GCT CCA ACT TCA ATG TTG GAT CAA AGT TTA TCT TCT CTT CAA TTT GCT AGG GGA TCC TAG CTAGCTAGCCATG
CTA AGC TCT TTA CAT AAT CAC CGA GGT TGA AGT TAC AAC CTA GTT TCA AAT AGA AGA GAA GTT AAA CGA TCC CCT AGG ATC GATCGATCGGTAC
Asp Ser Arg Asn Val Leu Val Ala Pro Thr Ser Met Leu Asp Gln Ser Leu Ser Ser Leu Gln Phe Ala Arg Gly Ser End>
___c___c___c___c___c___c___c___c___c__RECOMBINANT LEUKOTOXIN PEPTIDE___c___c___c___c___c___c___c___c___c___>
                                                                                          _b___VECTOR SEQUENCE_______>
```

SRIF-1: 5'-GATCCAGCTCTTCTGCCGGCTGCAAAAACTTCTTCTGGAAAACCTTCACCAGCTGCTAGG-3'
SRIF-2: 3'-GTCGAGAAGACGGCCGACGTTTTTGAAGAAGACCTTTTGGAAGTGGTCGACGATCCCTAG-5'

GNRH-1: 5'-GATCTCAGCATTGGAGCTACGGCCTGCGCCCTGGCTAAG-3'
GNRH-2: 3'-AGTCGTAACCTCGATGCCGGACGCGGGACCGATTCCTAG-5'

VP4-1: 5'-GATCTTGCAACATTGTGCCTGTGAGCATTGTGAGCCGCAACATTGTGTACACCCGCGCGCAACCTAACCAAGACATTGTGTAG-3'
VP4-2: 3'-AACGTTGTAACACGGACACTCGTAACACTCGGCGTTGTAACACATGTGGGCGCGCGTTGAATTGGTTCTGTAACACATCCTAG-5'

Figure 4 tac = hybrid trp::lac promoter from E. coli
bla = beta lactamase gene (ampicillin resistance)
lktA = Pasteurella haemolytica structural gene
SRIF = SRIF structural gene
lacl = E. coli lac operon repressor

```
          10         20         30         40
    *      *     *     *     *     *     *     *     *
ATG GCT ACT GTT ATA GAT CTA AGC TTC CCA AAA ACT GGG GCA AAA AAA
TAC CGA TGA CAA TAT CTA GAT TCG AAG GGT TTT TGA CCC CGT TTT TTT
Met Ala Thr Val Ile Asp Leu Ser Phe Pro Lys Thr Gly Ala Lys Lys>
___a___a____RECOMBINANT LEUKOTOXIN PEPTIDE [SPLIT]_a___a___a___>

50         60         70         80         90
 *     *     *     *     *     *     *     *     *     *
ATT ATC CTC TAT ATT CCC CAA AAT TAC CAA TAT GAT ACT GAA CAA GGT
TAA TAG GAG ATA TAA GGG GTT TTA ATG GTT ATA CTA TGA CTT GTT CCA
Ile Ile Leu Tyr Ile Pro Gln Asn Tyr Gln Tyr Asp Thr Glu Gln Gly>
___a___a____RECOMBINANT LEUKOTOXIN PEPTIDE [SPLIT]_a___a___a___>

  100        110        120        130        140
    *     *     *     *     *     *     *     *     *
AAT GGT TTA CAG GAT TTA GTC AAA GCG GCC GAA GAG TTG GGG ATT GAG
TTA CCA AAT GTC CTA AAT CAG TTT CGC CGG CTT CTC AAC CCC TAA CTC
Asn Gly Leu Gln Asp Leu Val Lys Ala Ala Glu Glu Leu Gly Ile Glu>
___a___a____RECOMBINANT LEUKOTOXIN PEPTIDE [SPLIT]_a___a___a___>

    150        160        170        180        190
*     *     *     *     *     *     *     *     *     *
GTA CAA AGA GAA GAA CGC AAT AAT ATT GCA ACA GCT CAA ACC AGT TTA
CAT GTT TCT CTT CTT GCG TTA TTA TAA CGT TGT CGA GTT TGG TCA AAT
Val Gln Arg Glu Glu Arg Asn Asn Ile Ala Thr Ala Gln Thr Ser Leu>
___a___a____RECOMBINANT LEUKOTOXIN PEPTIDE [SPLIT]_a___a___a___>

        200        210        220        230        240
  *     *     *     *     *     *     *     *     *     *
GGC ACG ATT CAA ACC GCT ATT GGC TTA ACT GAG CGT GGC ATT GTG TTA
CCG TGC TAA GTT TGG CGA TAA CCG AAT TGA CTC GCA CCG TAA CAC AAT
Gly Thr Ile Gln Thr Ala Ile Gly Leu Thr Glu Arg Gly Ile Val Leu>
___a___a____RECOMBINANT LEUKOTOXIN PEPTIDE [SPLIT]_a___a___a___>
```

Figure 6-1

```
          250         260         270          280
     *     *     *     *     *     *     *     *     *
TCC GCT CCA CAA ATT GAT AAA TTG CTA CAG AAA ACT AAA GCA GGC CAA
AGG CGA GGT GTT TAA CTA TTT AAC GAT GTC TTT TGA TTT CGT CCG GTT
Ser Ala Pro Gln Ile Asp Lys Leu Leu Gln Lys Thr Lys Ala Gly Gln>
___a___a____RECOMBINANT LEUKOTOXIN PEPTIDE [SPLIT]_a___a___a___>

290         300         310         320         330
 *     *     *     *     *     *     *     *     *     *
GCA TTA GGT TCT GCC GAA AGC ATT GTA CAA AAT GCA AAT AAA GCC AAA
CGT AAT CCA AGA CGG CTT TCG TAA CAT GTT TTA CGT TTA TTT CGG TTT
Ala Leu Gly Ser Ala Glu Ser Ile Val Gln Asn Ala Asn Lys Ala Lys>
___a___a____RECOMBINANT LEUKOTOXIN PEPTIDE [SPLIT]_a___a___a___>

  340         350         360          370         380
     *     *     *     *     *     *     *     *     *
ACT GTA TTA TCT GGC ATT CAA TCT ATT TTA GGC TCA GTA TTG GCT GGA
TGA CAT AAT AGA CCG TAA GTT AGA TAA AAT CCG AGT CAT AAC CGA CCT
Thr Val Leu Ser Gly Ile Gln Ser Ile Leu Gly Ser Val Leu Ala Gly>
___a___a____RECOMBINANT LEUKOTOXIN PEPTIDE [SPLIT]_a___a___a___>

    390          400         410         420          430
 *     *     *     *     *     *     *     *     *     *
ATG GAT TTA GAT GAG GCC TTA CAG AAT AAC AGC AAC CAA CAT GCT CTT
TAC CTA AAT CTA CTC CGG AAT GTC TTA TTG TCG TTG GTT GTA CGA GAA
Met Asp Leu Asp Glu Ala Leu Gln Asn Asn Ser Asn Gln His Ala Leu>
___a___a____RECOMBINANT LEUKOTOXIN PEPTIDE [SPLIT]_a___a___a___>

       440         450          460         470          480
   *     *     *     *     *     *     *     *     *     *
GCT AAA GCT GGC TTG GAG CTA ACA AAT TCA TTA ATT GAA AAT ATT GCT
CGA TTT CGA CCG AAC CTC GAT TGT TTA AGT AAT TAA CTT TTA TAA CGA
Ala Lys Ala Gly Leu Glu Leu Thr Asn Ser Leu Ile Glu Asn Ile Ala>
___a___a____RECOMBINANT LEUKOTOXIN PEPTIDE [SPLIT]_a___a___a___>

          490         500         510         520
     *     *     *     *     *     *     *     *     *
AAT TCA GTA AAA ACA CTT GAC GAA TTT GGT GAG CAA ATT AGT CAA TTT
TTA AGT CAT TTT TGT GAA CTG CTT AAA CCA CTC GTT TAA TCA GTT AAA
Asn Ser Val Lys Thr Leu Asp Glu Phe Gly Glu Gln Ile Ser Gln Phe>
___a___a____RECOMBINANT LEUKOTOXIN PEPTIDE [SPLIT]_a___a___a___>
```

Figure 6-2

```
530          540         550         560         570
 *     *     *     *     *     *     *     *     *     *
GGT TCA AAA CTA CAA AAT ATC AAA GGC TTA GGG ACT TTA GGA GAC AAA
CCA AGT TTT GAT GTT TTA TAG TTT CCG AAT CCC TGA AAT CCT CTG TTT
Gly Ser Lys Leu Gln Asn Ile Lys Gly Leu Gly Thr Leu Gly Asp Lys>
___a___a____RECOMBINANT LEUKOTOXIN PEPTIDE [SPLIT]_a___a___a___>

   580         590         600          610         620
     *     *     *     *     *     *     *     *     *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
___a___a____RECOMBINANT LEUKOTOXIN PEPTIDE [SPLIT]_a___a___a___>

     630         640         650         660         670
 *     *     *     *     *     *     *     *     *     *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
___a___a____RECOMBINANT LEUKOTOXIN PEPTIDE [SPLIT]_a___a___a___>

        680         690          700         710         720
 *     *     *     *     *     *     *     *     *     *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
___a___a____RECOMBINANT LEUKOTOXIN PEPTIDE [SPLIT]_a___a___a___>

           730         740         750         760
     *     *     *     *     *     *     *     *     *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
___a___a____RECOMBINANT LEUKOTOXIN PEPTIDE [SPLIT]_a___a___a___>

770          780         790         800         810
 *     *     *     *     *     *     *     *     *     *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
___a___a____RECOMBINANT LEUKOTOXIN PEPTIDE [SPLIT]_a___a___a___>

   820         830         840          850         860
     *     *     *     *     *     *     *     *     *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
___a___a____RECOMBINANT LEUKOTOXIN PEPTIDE [SPLIT]_a___a___a___>
```

Figure 6-3

```
         870         880         890         900         910
   *     *     *     *     *     *     *     *     *     *
GGT ATT GCC GAT AAA TTT AAT CAT GCA AAA AGT TTA GAG AGT TAT GCC
CCA TAA CGG CTA TTT AAA TTA GTA CGT TTT TCA AAT CTC TCA ATA CGG
Gly Ile Ala Asp Lys Phe Asn His Ala Lys Ser Leu Glu Ser Tyr Ala>
___a___a____RECOMBINANT LEUKOTOXIN PEPTIDE [SPLIT]_a___a___a___>

         920         930         940         950         960
   *     *     *     *     *     *     *     *     *     *
GAA CGC TTT AAA AAA TTA GGC TAT GAC GGA GAT AAT TTA TTA GCA GAA
CTT GCG AAA TTT TTT AAT CCG ATA CTG CCT CTA TTA AAT AAT CGT CTT
Glu Arg Phe Lys Lys Leu Gly Tyr Asp Gly Asp Asn Leu Leu Ala Glu>
___a___a____RECOMBINANT LEUKOTOXIN PEPTIDE [SPLIT]_a___a___a___>

         970         980         990        1000
   *     *     *     *     *     *     *     *     *
TAT CAG CGG GGA ACA GGG ACT ATT GAT GCA TCG GTT ACT GCA ATT AAT
ATA GTC GCC CCT TGT CCC TGA TAA CTA CGT AGC CAA TGA CGT TAA TTA
Tyr Gln Arg Gly Thr Gly Thr Ile Asp Ala Ser Val Thr Ala Ile Asn>
___a___a____RECOMBINANT LEUKOTOXIN PEPTIDE [SPLIT]_a___a___a___>

1010        1020        1030        1040        1050
   *     *     *     *     *     *     *     *     *     *
ACC GCA TTG GCC GCT ATT GCT GGT GGT GTG TCT GCT GCT GCA GCC GGC
TGG CGT AAC CGG CGA TAA CGA CCA CCA CAC AGA CGA CGA CGT CGG CCG
Thr Ala Leu Ala Ala Ile Ala Gly Gly Val Ser Ala Ala Ala Ala Gly>
___a___a____RECOMBINANT LEUKOTOXIN PEPTIDE [SPLIT]_a___a___a___>

   1060        1070        1080        1090        1100
      *     *     *     *     *     *     *     *     *
TCG GTT ATT GCT TCA CCG ATT GCC TTA TTA GTA TCT GGG ATT ACC GGT
AGC CAA TAA CGA AGT GGC TAA CGG AAT AAT CAT AGA CCC TAA TGG CCA
Ser Val Ile Ala Ser Pro Ile Ala Leu Leu Val Ser Gly Ile Thr Gly>
___a___a____RECOMBINANT LEUKOTOXIN PEPTIDE [SPLIT]_a___a___a___>

      1110        1120        1130        1140        1150
   *     *     *     *     *     *     *     *     *     *
GTA ATT TCT ACG ATT CTG CAA TAT TCT AAA CAA GCA ATG TTT GAG CAC
CAT TAA AGA TGC TAA GAC GTT ATA AGA TTT GTT CGT TAC AAA CTC GTG
Val Ile Ser Thr Ile Leu Gln Tyr Ser Lys Gln Ala Met Phe Glu His>
___a___a____RECOMBINANT LEUKOTOXIN PEPTIDE [SPLIT]_a___a___a___>
```

Figure 6-4

```
           1160          1170           1180          1190          1200
    *       *       *      *       *       *      *       *       *     *
GTT GCA AAT AAA ATT CAT AAC AAA ATT GTA GAA TGG GAA AAA AAT AAT
CAA CGT TTA TTT TAA GTA TTG TTT TAA CAT CTT ACC CTT TTT TTA TTA
Val Ala Asn Lys Ile His Asn Lys Ile Val Glu Trp Glu Lys Asn Asn>
___a___a____RECOMBINANT LEUKOTOXIN PEPTIDE [SPLIT]_a___a___a___>

              1210          1220          1230           1240
       *       *      *       *       *      *       *       *      *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___a___a____RECOMBINANT LEUKOTOXIN PEPTIDE [SPLIT]_a___a___a___>

1250          1260           1270          1280          1290
  *       *       *      *       *      *       *       *      *      *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___a___a____RECOMBINANT LEUKOTOXIN PEPTIDE [SPLIT]_a___a___a___>

   1300          1310          1320           1330          1340
      *      *      *       *      *      *       *      *      *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___a___a____RECOMBINANT LEUKOTOXIN PEPTIDE [SPLIT]_a___a___a___>

     1350          1360          1370          1380           1390
  *       *       *      *      *       *      *      *       *      *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___a___a____RECOMBINANT LEUKOTOXIN PEPTIDE [SPLIT]_a___a___a___>

           1400          1410           1420          1430          1440
    *       *       *      *       *       *      *       *       *     *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___a___a____RECOMBINANT LEUKOTOXIN PEPTIDE [SPLIT]_a___a___a___>

              1450          1460          1470           1480
       *       *      *       *       *      *       *       *      *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___a___a____RECOMBINANT LEUKOTOXIN PEPTIDE [SPLIT]_a___a___a___>
```

Figure 6-5

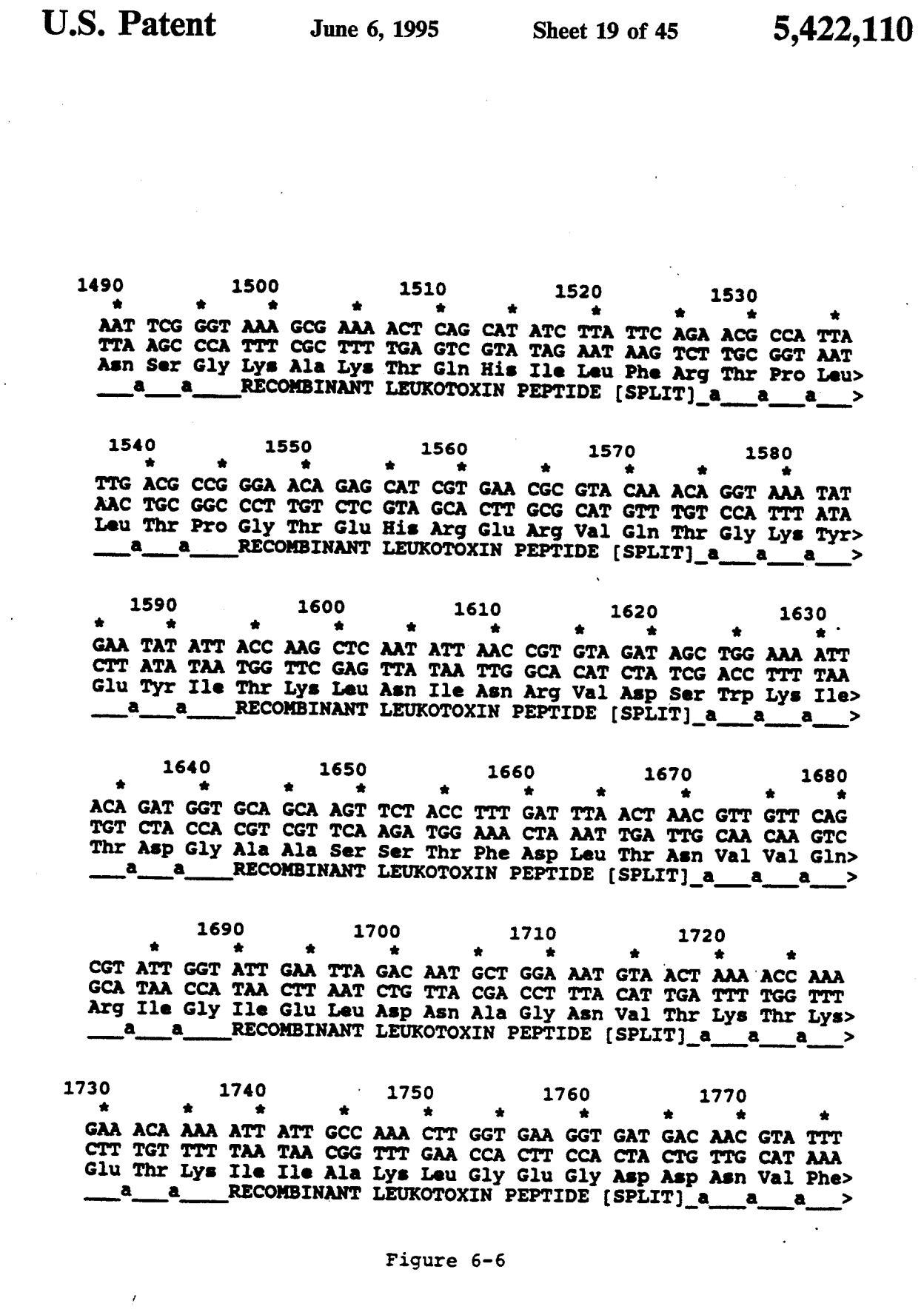

```
1490        1500        1510        1520        1530
AAT TCG GGT AAA GCG AAA ACT CAG CAT ATC TTA TTC AGA ACG CCA TTA
TTA AGC CCA TTT CGC TTT TGA GTC GTA TAG AAT AAG TCT TGC GGT AAT
Asn Ser Gly Lys Ala Lys Thr Gln His Ile Leu Phe Arg Thr Pro Leu>
___a___a____RECOMBINANT LEUKOTOXIN PEPTIDE [SPLIT]_a___a___a___>

1540        1550        1560        1570        1580
TTG ACG CCG GGA ACA GAG CAT CGT GAA CGC GTA CAA ACA GGT AAA TAT
AAC TGC GGC CCT TGT CTC GTA GCA CTT GCG CAT GTT TGT CCA TTT ATA
Leu Thr Pro Gly Thr Glu His Arg Glu Arg Val Gln Thr Gly Lys Tyr>
___a___a____RECOMBINANT LEUKOTOXIN PEPTIDE [SPLIT]_a___a___a___>

1590        1600        1610        1620        1630
GAA TAT ATT ACC AAG CTC AAT ATT AAC CGT GTA GAT AGC TGG AAA ATT
CTT ATA TAA TGG TTC GAG TTA TAA TTG GCA CAT CTA TCG ACC TTT TAA
Glu Tyr Ile Thr Lys Leu Asn Ile Asn Arg Val Asp Ser Trp Lys Ile>
___a___a____RECOMBINANT LEUKOTOXIN PEPTIDE [SPLIT]_a___a___a___>

1640        1650        1660        1670        1680
ACA GAT GGT GCA GCA AGT TCT ACC TTT GAT TTA ACT AAC GTT GTT CAG
TGT CTA CCA CGT CGT TCA AGA TGG AAA CTA AAT TGA TTG CAA CAA GTC
Thr Asp Gly Ala Ala Ser Ser Thr Phe Asp Leu Thr Asn Val Val Gln>
___a___a____RECOMBINANT LEUKOTOXIN PEPTIDE [SPLIT]_a___a___a___>

1690        1700        1710        1720
CGT ATT GGT ATT GAA TTA GAC AAT GCT GGA AAT GTA ACT AAA ACC AAA
GCA TAA CCA TAA CTT AAT CTG TTA CGA CCT TTA CAT TGA TTT TGG TTT
Arg Ile Gly Ile Glu Leu Asp Asn Ala Gly Asn Val Thr Lys Thr Lys>
___a___a____RECOMBINANT LEUKOTOXIN PEPTIDE [SPLIT]_a___a___a___>

1730        1740        1750        1760        1770
GAA ACA AAA ATT ATT GCC AAA CTT GGT GAA GGT GAT GAC AAC GTA TTT
CTT TGT TTT TAA TAA CGG TTT GAA CCA CTT CCA CTA CTG TTG CAT AAA
Glu Thr Lys Ile Ile Ala Lys Leu Gly Glu Gly Asp Asp Asn Val Phe>
___a___a____RECOMBINANT LEUKOTOXIN PEPTIDE [SPLIT]_a___a___a___>
```

Figure 6-6

```
 1780        1790        1800         1810        1820
    *     *     *     *     *     *     *     *     *
GTT GGT TCT GGT ACG ACG GAA ATT GAT GGC GGT GAA GGT TAC GAC CGA
CAA CCA AGA CCA TGC TGC CTT TAA CTA CCG CCA CTT CCA ATG CTG GCT
Val Gly Ser Gly Thr Thr Glu Ile Asp Gly Gly Glu Gly Tyr Asp Arg>
___a___a____RECOMBINANT LEUKOTOXIN PEPTIDE [SPLIT]_a___a___a___>

   1830        1840        1850        1860         1870
 *     *     *     *     *     *     *     *     *     *
GTT CAC TAT AGC CGT GGA AAC TAT GGT GCT TTA ACT ATT GAT GCA ACC
CAA GTG ATA TCG GCA CCT TTG ATA CCA CGA AAT TGA TAA CTA CGT TGG
Val His Tyr Ser Arg Gly Asn Tyr Gly Ala Leu Thr Ile Asp Ala Thr>
___a___a____RECOMBINANT LEUKOTOXIN PEPTIDE [SPLIT]_a___a___a___>

      1880        1890         1900        1910        1920
  *     *     *     *     *     *     *     *     *     *
AAA GAG ACC GAG CAA GGT AGT TAT ACC GTA AAT CGT TTC GTA GAA ACC
TTT CTC TGG CTC GTT CCA TCA ATA TGG CAT TTA GCA AAG CAT CTT TGG
Lys Glu Thr Glu Gln Gly Ser Tyr Thr Val Asn Arg Phe Val Glu Thr>
___a___a____RECOMBINANT LEUKOTOXIN PEPTIDE [SPLIT]_a___a___a___>

         1930        1940        1950         1960
      *     *     *     *     *     *     *     *     *
GGT AAA GCA CTA CAC GAA GTG ACT TCA ACC CAT ACC GCA TTA GTG GGC
CCA TTT CGT GAT GTG CTT CAC TGA AGT TGG GTA TGG CGT AAT CAC CCG
Gly Lys Ala Leu His Glu Val Thr Ser Thr His Thr Ala Leu Val Gly>
___a___a____RECOMBINANT LEUKOTOXIN PEPTIDE [SPLIT]_a___a___a___>

1970        1980         1990        2000        2010
 *     *     *     *     *     *     *     *     *     *
AAC CGT GAA GAA AAA ATA GAA TAT CGT CAT AGC AAT AAC CAG CAC CAT
TTG GCA CTT CTT TTT TAT CTT ATA GCA GTA TCG TTA TTG GTC GTG GTA
Asn Arg Glu Glu Lys Ile Glu Tyr Arg His Ser Asn Asn Gln His His>
___a___a____RECOMBINANT LEUKOTOXIN PEPTIDE [SPLIT]_a___a___a___>

 2020        2030        2040         2050        2060
    *     *     *     *     *     *     *     *     *
GCC GGT TAT TAC ACC AAA GAT ACC TTG AAA GCT GTT GAA GAA ATT ATC
CGG CCA ATA ATG TGG TTT CTA TGG AAC TTT CGA CAA CTT CTT TAA TAG
Ala Gly Tyr Tyr Thr Lys Asp Thr Leu Lys Ala Val Glu Glu Ile Ile>
___a___a____RECOMBINANT LEUKOTOXIN PEPTIDE [SPLIT]_a___a___a___>

   2070        2080        2090        2100         2110
 *     *     *     *     *     *     *     *     *     *
GGT ACA TCA CAT AAC GAT ATC TTT AAA GGT AGT AAG TTC AAT GAT GCC
CCA TGT AGT GTA TTG CTA TAG AAA TTT CCA TCA TTC AAG TTA CTA CGG
Gly Thr Ser His Asn Asp Ile Phe Lys Gly Ser Lys Phe Asn Asp Ala>
___a___a____RECOMBINANT LEUKOTOXIN PEPTIDE [SPLIT]_a___a___a___>
```

Figure 6-7

```
     2120       2130        2140       2150       2160
 *     *     *     *     *     *     *     *     *     *
TTT AAC GGT GGT GAT GGT GTC GAT ACT ATT GAC GGT AAC GAC GGC AAT
AAA TTG CCA CCA CTA CCA CAG CTA TGA TAA CTG CCA TTG CTG CCG TTA
Phe Asn Gly Gly Asp Gly Val Asp Thr Ile Asp Gly Asn Asp Gly Asn>
___a___a____RECOMBINANT LEUKOTOXIN PEPTIDE [SPLIT]_a___a___a___>

        2170       2180       2190        2200
   *     *     *     *     *     *     *     *     *
GAC CGC TTA TTT GGT GGT AAA GGC GAT GAT ATT CTC GAT GGT GGA AAT
CTG GCG AAT AAA CCA CCA TTT CCG CTA CTA TAA GAG CTA CCA CCT TTA
Asp Arg Leu Phe Gly Gly Lys Gly Asp Asp Ile Leu Asp Gly Gly Asn>
___a___a____RECOMBINANT LEUKOTOXIN PEPTIDE [SPLIT]_a___a___a___>

2210        2220        2230        2240       2250
 *     *     *     *     *     *     *     *     *     *
GGT GAT GAT TTT ATC GAT GGC GGT AAA GGC AAC GAC CTA TTA CAC GGT
CCA CTA CTA AAA TAG CTA CCG CCA TTT CCG TTG CTG GAT AAT GTG CCA
Gly Asp Asp Phe Ile Asp Gly Gly Lys Gly Asn Asp Leu Leu His Gly>
___a___a____RECOMBINANT LEUKOTOXIN PEPTIDE [SPLIT]_a___a___a___>

 2260       2270        2280        2290       2300
    *     *     *     *     *     *     *     *     *
GGC AAG GGC GAT GAT ATT TTC GTT CAC CGT AAA GGC GAT GGT AAT GAT
CCG TTC CCG CTA CTA TAA AAG CAA GTG GCA TTT CCG CTA CCA TTA CTA
Gly Lys Gly Asp Asp Ile Phe Val His Arg Lys Gly Asp Gly Asn Asp>
___a___a____RECOMBINANT LEUKOTOXIN PEPTIDE [SPLIT]_a___a___a___>

   2310       2320        2330       2340       2350
 *     *     *     *     *     *     *     *     *     *
ATT ATT ACC GAT TCT GAC GGC AAT GAT AAA TTA TCA TTC TCT GAT TCG
TAA TAA TGG CTA AGA CTG CCG TTA CTA TTT AAT AGT AAG AGA CTA AGC
Ile Ile Thr Asp Ser Asp Gly Asn Asp Lys Leu Ser Phe Ser Asp Ser>
___a___a____RECOMBINANT LEUKOTOXIN PEPTIDE [SPLIT]_a___a___a___>

      2360       2370        2380       2390       2400
 *     *     *     *     *     *     *     *     *     *
AAC TTA AAA GAT TTA ACA TTT GAA AAA GTT AAA CAT AAT CTT GTC ATC
TTG AAT TTT CTA AAT TGT AAA CTT TTT CAA TTT GTA TTA GAA CAG TAG
Asn Leu Lys Asp Leu Thr Phe Glu Lys Val Lys His Asn Leu Val Ile>
___a___a____RECOMBINANT LEUKOTOXIN PEPTIDE [SPLIT]_a___a___a___>
```

Figure 6-8

```
         2410       2420       2430        2440
      *     *    *    *     *    *     *     *     *
ACG AAT AGC AAA AAA GAG AAA GTG ACC ATT CAA AAC TGG TTC CGA GAG
TGC TTA TCG TTT TTT CTC TTT CAC TGG TAA GTT TTG ACC AAG GCT CTC
Thr Asn Ser Lys Lys Glu Lys Val Thr Ile Gln Asn Trp Phe Arg Glu>
___a___a____RECOMBINANT LEUKOTOXIN PEPTIDE [SPLIT]_a___a___a___>

2450       2460       2470       2480       2490
 *     *    *     *     *     *    *     *    *     *
GCT GAT TTT GCT AAA GAA GTG CCT AAT TAT AAA GCA ACT AAA GAT GAG
CGA CTA AAA CGA TTT CTT CAC GGA TTA ATA TTT CGT TGA TTT CTA CTC
Ala Asp Phe Ala Lys Glu Val Pro Asn Tyr Lys Ala Thr Lys Asp Glu>
___a___a____RECOMBINANT LEUKOTOXIN PEPTIDE [SPLIT]_a___a___a___>

 2500       2510       2520        2530       2540
      *    *     *     *     *     *     *    *     *
AAA ATC GAA GAA ATC ATC GGT CAA AAT GGC GAG CGG ATC ACC TCA AAG
TTT TAG CTT CTT TAG TAG CCA GTT TTA CCG CTC GCC TAG TGG AGT TTC
Lys Ile Glu Glu Ile Ile Gly Gln Asn Gly Glu Arg Ile Thr Ser Lys>
___a___a____RECOMBINANT LEUKOTOXIN PEPTIDE [SPLIT]_a___a___a___>

   2550        2560       2570       2580        2590
*    *     *     *    *     *     *    *     *     *
CAA GTT GAT GAT CTT ATC GCA AAA GGT AAC GGC AAA ATT ACC CAA GAT
GTT CAA CTA CTA GAA TAG CGT TTT CCA TTG CCG TTT TAA TGG GTT CTA
Gln Val Asp Asp Leu Ile Ala Lys Gly Asn Gly Lys Ile Thr Gln Asp>
___a___a____RECOMBINANT LEUKOTOXIN PEPTIDE [SPLIT]_a___a___a___>

      2600       2610        2620       2630       2640
  *     *     *    *     *     *     *     *    *     *
GAG CTA TCA AAA GTT GTT GAT AAC TAT GAA TTG CTC AAA CAT AGC AAA
CTC GAT AGT TTT CAA CAA CTA TTG ATA CTT AAC GAG TTT GTA TCG TTT
Glu Leu Ser Lys Val Val Asp Asn Tyr Glu Leu Leu Lys His Ser Lys>
___a___a____RECOMBINANT LEUKOTOXIN PEPTIDE [SPLIT]_a___a___a___>

         2650       2660       2670        2680
      *     *    *     *     *    *     *     *    *
AAT GTG ACA AAC AGC TTA GAT AAG TTA ATC TCA TCT GTA AGT GCA TTT
TTA CAC TGT TTG TCG AAT CTA TTC AAT TAG AGT AGA CAT TCA CGT AAA
Asn Val Thr Asn Ser Leu Asp Lys Leu Ile Ser Ser Val Ser Ala Phe>
___a___a____RECOMBINANT LEUKOTOXIN PEPTIDE [SPLIT]_a___a___a___>

2690       2700       2710       2720       2730
 *     *    *     *     *    *     *     *    *     *
ACC TCG TCT AAT GAT TCG AGA AAT GTA TTA GTG GCT CCA ACT TCA ATG
TGG AGC AGA TTA CTA AGC TCT TTA CAT AAT CAC CGA GGT TGA AGT TAC
Thr Ser Ser Asn Asp Ser Arg Asn Val Leu Val Ala Pro Thr Ser Met>
___a___a____RECOMBINANT LEUKOTOXIN PEPTIDE [SPLIT]_a___a___a___>
```

Figure 6-9

```
 2740          2750          2760           2770          2780
    *     *      *      *      *      *      *      *      *
TTG GAT CAA AGT TTA TCT TCT CTT CAA TTT GCT AGG GGA TCC AGC TCT
AAC CTA GTT TCA AAT AGA AGA GAA GTT AAA CGA TCC CCT AGG TCG AGA
Leu Asp Gln Ser Leu Ser Ser Leu Gln Phe Ala Arg Gly Ser>
___a____RECOMBINANT LEUKOTOXIN PEPTIDE [SPLIT]_a___a___>
                                                        Ser Ser>
                                                        ___b___>

  2790          2800          2810          2820          2830
*      *      *      *      *      *      *      *      *      *
TCT GCC GGC TGC AAA AAC TTC TTC TGG AAA ACC TTC ACC AGC TGC TAG
AGA CGG CCG ACG TTT TTG AAG AAG ACC TTT TGG AAG TGG TCG ACG ATC
Ser>
___>
    Ala Gly Cys Lys Asn Phe Phe Trp Lys Thr Phe Thr Ser Cys End>
    ___c___c___c___c___c___SRIF PEPTIDE____c___c___c___c___c___>

  *
GGATCC
CCTAGG
```

Figure 6-10

*tac = hybrid trp::lac promoter from E. coli*
*bla = beta lactamase gene (ampicillin resistance)*
*lktA = Pasteurella haemolytica structural gene*
*GnRH = GnRH gene*
*lacI = E. coli lac operon repressor*

```
              10          20          30          40
     *     *     *     *     *     *     *     *     *
ATG GCT ACT GTT ATA GAT CTA AGC TTC CCA AAA ACT GGG GCA AAA AAA
TAC CGA TGA CAA TAT CTA GAT TCG AAG GGT TTT TGA CCC CGT TTT TTT
Met Ala Thr Val Ile Asp Leu Ser Phe Pro Lys Thr Gly Ala Lys Lys>
___b___b____RECOMBINANT LEUKOTOXIN PEPTIDE [SPLIT]_b___b___b___>

50          60          70          80          90
 *     *     *     *     *     *     *     *     *     *
ATT ATC CTC TAT ATT CCC CAA AAT TAC CAA TAT GAT ACT GAA CAA GGT
TAA TAG GAG ATA TAA GGG GTT TTA ATG GTT ATA CTA TGA CTT GTT CCA
Ile Ile Leu Tyr Ile Pro Gln Asn Tyr Gln Tyr Asp Thr Glu Gln Gly>
___b___b____RECOMBINANT LEUKOTOXIN PEPTIDE [SPLIT]_b___b___b___>

  100         110         120         130         140
     *     *     *     *     *     *     *     *     *
AAT GGT TTA CAG GAT TTA GTC AAA GCG GCC GAA GAG TTG GGG ATT GAG
TTA CCA AAT GTC CTA AAT CAG TTT CGC CGG CTT CTC AAC CCC TAA CTC
Asn Gly Leu Gln Asp Leu Val Lys Ala Ala Glu Glu Leu Gly Ile Glu>
___b___b____RECOMBINANT LEUKOTOXIN PEPTIDE [SPLIT]_b___b___b___>

    150         160         170         180         190
*     *     *     *     *     *     *     *     *     *
GTA CAA AGA GAA GAA CGC AAT AAT ATT GCA ACA GCT CAA ACC AGT TTA
CAT GTT TCT CTT CTT GCG TTA TTA TAA CGT TGT CGA GTT TGG TCA AAT
Val Gln Arg Glu Glu Arg Asn Asn Ile Ala Thr Ala Gln Thr Ser Leu>
___b___b____RECOMBINANT LEUKOTOXIN PEPTIDE [SPLIT]_b___b___b___>

        200         210         220         230         240
  *     *     *     *     *     *     *     *     *     *
GGC ACG ATT CAA ACC GCT ATT GGC TTA ACT GAG CGT GGC ATT GTG TTA
CCG TGC TAA GTT TGG CGA TAA CCG AAT TGA CTC GCA CCG TAA CAC AAT
Gly Thr Ile Gln Thr Ala Ile Gly Leu Thr Glu Arg Gly Ile Val Leu>
___b___b____RECOMBINANT LEUKOTOXIN PEPTIDE [SPLIT]_b___b___b___>
```

Figure 8-1

```
                 250         260         270          280
          *      *     *     *     *     *     *      *     *
TCC GCT CCA CAA ATT GAT AAA TTG CTA CAG AAA ACT AAA GCA GGC CAA
AGG CGA GGT GTT TAA CTA TTT AAC GAT GTC TTT TGA TTT CGT CCG GTT
Ser Ala Pro Gln Ile Asp Lys Leu Leu Gln Lys Thr Lys Ala Gly Gln>
___b___b____RECOMBINANT LEUKOTOXIN PEPTIDE [SPLIT]_b___b___b___>

290         300         310         320         330
 *     *     *     *     *     *     *     *     *     *
GCA TTA GGT TCT GCC GAA AGC ATT GTA CAA AAT GCA AAT AAA GCC AAA
CGT AAT CCA AGA CGG CTT TCG TAA CAT GTT TTA CGT TTA TTT CGG TTT
Ala Leu Gly Ser Ala Glu Ser Ile Val Gln Asn Ala Asn Lys Ala Lys>
___b___b____RECOMBINANT LEUKOTOXIN PEPTIDE [SPLIT]_b___b___b___>

  340         350         360          370         380
    *     *     *     *     *     *     *     *     *
ACT GTA TTA TCT GGC ATT CAA TCT ATT TTA GGC TCA GTA TTG GCT GGA
TGA CAT AAT AGA CCG TAA GTT AGA TAA AAT CCG AGT CAT AAC CGA CCT
Thr Val Leu Ser Gly Ile Gln Ser Ile Leu Gly Ser Val Leu Ala Gly>
___b___b____RECOMBINANT LEUKOTOXIN PEPTIDE [SPLIT]_b___b___b___>

    390          400         410         420          430
 *     *     *     *     *     *     *     *     *     *
ATG GAT TTA GAT GAG GCC TTA CAG AAT AAC AGC AAC CAA CAT GCT CTT
TAC CTA AAT CTA CTC CGG AAT GTC TTA TTG TCG TTG GTT GTA CGA GAA
Met Asp Leu Asp Glu Ala Leu Gln Asn Asn Ser Asn Gln His Ala Leu>
___b___b____RECOMBINANT LEUKOTOXIN PEPTIDE [SPLIT]_b___b___b___>

       440         450          460         470         480
    *     *     *     *     *     *     *     *     *     *
GCT AAA GCT GGC TTG GAG CTA ACA AAT TCA TTA ATT GAA AAT ATT GCT
CGA TTT CGA CCG AAC CTC GAT TGT TTA AGT AAT TAA CTT TTA TAA CGA
Ala Lys Ala Gly Leu Glu Leu Thr Asn Ser Leu Ile Glu Asn Ile Ala>
___b___b____RECOMBINANT LEUKOTOXIN PEPTIDE [SPLIT]_b___b___b___>

              490         500         510          520
          *      *     *     *     *     *     *      *     *
AAT TCA GTA AAA ACA CTT GAC GAA TTN -GT GAG CAA ATT AGT CAA TTT
TTA AGT CAT TTT TGT GAA CTG CTT AAN -CA CTC GTT TAA TCA GTT AAA
Asn Ser Val Lys Thr Leu Asp Glu Xxx Cys Glu Gln Ile Ser Gln Phe>
___b___b____RECOMBINANT LEUKOTOXIN PEPTIDE [SPLIT]_b___b___b___>

530         540          550         560         570
 *     *     *     *     *     *     *     *     *     *
GGT TCA AAA CTA CAA AAT ATC AAA GGC TTA GGG ACT TTA GGA GAC AAA
CCA AGT TTT GAT GTT TTA TAG TTT CCG AAT CCC TGA AAT CCT CTG TTT
Gly Ser Lys Leu Gln Asn Ile Lys Gly Leu Gly Thr Leu Gly Asp Lys>
___b___b____RECOMBINANT LEUKOTOXIN PEPTIDE [SPLIT]_b___b___b___>
```

Figure 8-2

```
   580         590         600          610         620
     *    *     *     *    *     *     *    *     *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
___b___b____RECOMBINANT LEUKOTOXIN PEPTIDE [SPLIT]_b___b___b___>

     630         640         650         660         670
*    *     *     *     *     *     *     *     *     *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
___b___b____RECOMBINANT LEUKOTOXIN PEPTIDE [SPLIT]_b___b___b___>

        680         690          700         710         720
  *      *     *     *     *     *     *     *     *     *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
___b___b____RECOMBINANT LEUKOTOXIN PEPTIDE [SPLIT]_b___b___b___>

             730         740         750          760
     *        *     *     *     *     *     *     *     *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
___b___b____RECOMBINANT LEUKOTOXIN PEPTIDE [SPLIT]_b___b___b___>

770          780         790          800         810
 *      *     *     *     *     *     *     *     *     *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
___b___b____RECOMBINANT LEUKOTOXIN PEPTIDE [SPLIT]_b___b___b___>

   820         830         840          850         860
     *    *     *     *    *     *     *    *     *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
___b___b____RECOMBINANT LEUKOTOXIN PEPTIDE [SPLIT]_b___b___b___>
```

Figure 8-3

```
    870         880         890         900         910
 *     *     *     *     *     *     *     *     *     *
GGT ATT GCC GAT AAA TTT AAT CAT GCA AAA AGT TTA GAG AGT TAT GCC
CCA TAA CGG CTA TTT AAA TTA GTA CGT TTT TCA AAT CTC TCA ATA CGG
Gly Ile Ala Asp Lys Phe Asn His Ala Lys Ser Leu Glu Ser Tyr Ala>
___b___b____RECOMBINANT LEUKOTOXIN PEPTIDE [SPLIT]_b___b___b___>

       920         930         940         950         960
  *     *     *     *     *     *     *     *     *     *
GAA CGC TTT AAA AAA TTA GGC TAT GAC GGA GAT AAT TTA TTA GCA GAA
CTT GCG AAA TTT TTT AAT CCG ATA CTG CCT CTA TTA AAT AAT CGT CTT
Glu Arg Phe Lys Lys Leu Gly Tyr Asp Gly Asp Asn Leu Leu Ala Glu>
___b___b____RECOMBINANT LEUKOTOXIN PEPTIDE [SPLIT]_b___b___b___>

          970         980         990        1000
      *     *     *     *     *     *     *     *     *
TAT CAG CGG GGA ACA GGG ACT ATT GAT GCA TCG GTT ACT GCA ATT AAT
ATA GTC GCC CCT TGT CCC TGA TAA CTA CGT AGC CAA TGA CGT TAA TTA
Tyr Gln Arg Gly Thr Gly Thr Ile Asp Ala Ser Val Thr Ala Ile Asn>
___b___b____RECOMBINANT LEUKOTOXIN PEPTIDE [SPLIT]_b___b___b___>

1010        1020        1030        1040        1050
 *     *     *     *     *     *     *     *     *     *
ACC GCA TTG GCC GCT ATT GCT GGT GGT GTG TCT GCT GCT GCA GCC GGC
TGG CGT AAC CGG CGA TAA CGA CCA CCA CAC AGA CGA CGA CGT CGG CCG
Thr Ala Leu Ala Ala Ile Ala Gly Gly Val Ser Ala Ala Ala Ala Gly>
___b___b____RECOMBINANT LEUKOTOXIN PEPTIDE [SPLIT]_b___b___b___>

 1060        1070        1080        1090        1100
    *     *     *     *     *     *     *     *     *
TCG GTT ATT GCT TCA CCG ATT GCC TTA TTA GTA TCT GGG ATT ACC GGT
AGC CAA TAA CGA AGT GGC TAA CGG AAT AAT CAT AGA CCC TAA TGG CCA
Ser Val Ile Ala Ser Pro Ile Ala Leu Leu Val Ser Gly Ile Thr Gly>
___b___b____RECOMBINANT LEUKOTOXIN PEPTIDE [SPLIT]_b___b___b___>

   1110        1120        1130        1140        1150
 *     *     *     *     *     *     *     *     *     *
GTA ATT TCT ACG ATT CTG CAA TAT TCT AAA CAA GCA ATG TTT GAG CAC
CAT TAA AGA TGC TAA GAC GTT ATA AGA TTT GTT CGT TAC AAA CTC GTG
Val Ile Ser Thr Ile Leu Gln Tyr Ser Lys Gln Ala Met Phe Glu His>
___b___b____RECOMBINANT LEUKOTOXIN PEPTIDE [SPLIT]_b___b___b___>

      1160        1170        1180        1190        1200
  *     *     *     *     *     *     *     *     *     *
GTT GCA AAT AAA ATT CAT AAC AAA ATT GTA GAA TGG GAA AAA AAT AAT
CAA CGT TTA TTT TAA GTA TTG TTT TAA CAT CTT ACC CTT TTT TTA TTA
Val Ala Asn Lys Ile His Asn Lys Ile Val Glu Trp Glu Lys Asn Asn>
___b___b____RECOMBINANT LEUKOTOXIN PEPTIDE [SPLIT]_b___b___b___>
```

Figure 8-4

```
        1210        1220        1230        1240
   *     *     *     *     *     *     *     *     *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___b___b____RECOMBINANT LEUKOTOXIN PEPTIDE [SPLIT]_b___b___b___>

1250        1260        1270        1280        1290
 *     *     *     *     *     *     *     *     *     *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___b___b____RECOMBINANT LEUKOTOXIN PEPTIDE [SPLIT]_b___b___b___>

 1300        1310        1320        1330        1340
   *     *     *     *     *     *     *     *     *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___b___b____RECOMBINANT LEUKOTOXIN PEPTIDE [SPLIT]_b___b___b___>

    1350        1360        1370        1380        1390
*     *     *     *     *     *     *     *     *     *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___b___b____RECOMBINANT LEUKOTOXIN PEPTIDE [SPLIT]_b___b___b___>

      1400        1410        1420        1430        1440
  *     *     *     *     *     *     *     *     *     *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___b___b____RECOMBINANT LEUKOTOXIN PEPTIDE [SPLIT]_b___b___b___>

        1450        1460        1470        1480
     *     *     *     *     *     *     *     *     *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___b___b____RECOMBINANT LEUKOTOXIN PEPTIDE [SPLIT]_b___b___b___>
```

Figure 8-5

```
1490          1500          1510          1520          1530
   *       *      *       *       *      *       *       *      *      *
  AAT TCG GGT AAA GCG AAA ACT CAG CAT ATC TTA TTC AGA ACG CCA TTA
  TTA AGC CCA TTT CGC TTT TGA GTC GTA TAG AAT AAG TCT TGC GGT AAT
  Asn Ser Gly Lys Ala Lys Thr Gln His Ile Leu Phe Arg Thr Pro Leu>
  ___b___b____RECOMBINANT LEUKOTOXIN PEPTIDE [SPLIT]_b___b___b___>

   1540          1550          1560           1570          1580
       *      *       *       *       *       *      *      *      *
  TTG ACG CCG GGA ACA GAG CAT CGT GAA CGC GTA CAA ACA GGT AAA TAT
  AAC TGC GGC CCT TGT CTC GTA GCA CTT GCG CAT GTT TGT CCA TTT ATA
  Leu Thr Pro Gly Thr Glu His Arg Glu Arg Val Gln Thr Gly Lys Tyr>
  ___b___b____RECOMBINANT LEUKOTOXIN PEPTIDE [SPLIT]_b___b___b___>

     1590           1600          1610          1620           1630
  *      *       *       *       *       *       *      *      *      *
  GAA TAT ATT ACC AAG CTC AAT ATT AAC CGT GTA GAT AGC TGG AAA ATT
  CTT ATA TAA TGG TTC GAG TTA TAA TTG GCA CAT CTA TCG ACC TTT TAA
  Glu Tyr Ile Thr Lys Leu Asn Ile Asn Arg Val Asp Ser Trp Lys Ile>
  ___b___b____RECOMBINANT LEUKOTOXIN PEPTIDE [SPLIT]_b___b___b___>

        1640          1650           1660          1670          1680
    *       *      *       *       *      *       *      *      *      *
  ACA GAT GGT GCA GCA AGT TCT ACC TTT GAT TTA ACT AAC GTT GTT CAG
  TGT CTA CCA CGT CGT TCA AGA TGG AAA CTA AAT TGA TTG CAA CAA GTC
  Thr Asp Gly Ala Ala Ser Ser Thr Phe Asp Leu Thr Asn Val Val Gln>
  ___b___b____RECOMBINANT LEUKOTOXIN PEPTIDE [SPLIT]_b___b___b___>

           1690          1700          1710           1720
        *      *      *       *       *      *      *      *      *
  CGT ATT GGT ATT GAA TTA GAC AAT GCT GGA AAT GTA ACT AAA ACC AAA
  GCA TAA CCA TAA CTT AAT CTG TTA CGA CCT TTA CAT TGA TTT TGG TTT
  Arg Ile Gly Ile Glu Leu Asp Asn Ala Gly Asn Val Thr Lys Thr Lys>
  ___b___b____RECOMBINANT LEUKOTOXIN PEPTIDE [SPLIT]_b___b___b___>

1730          1740           1750          1760          1770
   *       *      *       *       *      *       *       *      *      *
  GAA ACA AAA ATT ATT GCC AAA CTT GGT GAA GGT GAT GAC AAC GTA TTT
  CTT TGT TTT TAA TAA CGG TTT GAA CCA CTT CCA CTA CTG TTG CAT AAA
  Glu Thr Lys Ile Ile Ala Lys Leu Gly Glu Gly Asp Asp Asn Val Phe>
  ___b___b____RECOMBINANT LEUKOTOXIN PEPTIDE [SPLIT]_b___b___b___>

   1780          1790          1800           1810          1820
       *      *       *       *       *       *      *      *      *
  GTT GGT TCT GGT ACG ACG GAA ATT GAT GGC GGT GAA GGT TAC GAC CGA
  CAA CCA AGA CCA TGC TGC CTT TAA CTA CCG CCA CTT CCA ATG CTG GCT
  Val Gly Ser Gly Thr Thr Glu Ile Asp Gly Gly Glu Gly Tyr Asp Arg>
  ___b___b____RECOMBINANT LEUKOTOXIN PEPTIDE [SPLIT]_b___b___b___>
```

Figure 8-6

```
   1830        1840        1850        1860         1870
*    *     *     *    *     *     *     *     *     *
GTT CAC TAT AGC CGT GGA AAC TAT GGT GCT TTA ACT ATT GAT GCA ACC
CAA GTG ATA TCG GCA CCT TTG ATA CCA CGA AAT TGA TAA CTA CGT TGG
Val His Tyr Ser Arg Gly Asn Tyr Gly Ala Leu Thr Ile Asp Ala Thr>
___b___b____RECOMBINANT LEUKOTOXIN PEPTIDE [SPLIT]_b___b___b___>

     1880        1890        1900        1910        1920
  *     *     *     *     *     *     *     *     *     *
AAA GAG ACC GAG CAA GGT AGT TAT ACC GTA AAT CGT TTC GTA GAA ACC
TTT CTC TGG CTC GTT CCA TCA ATA TGG CAT TTA GCA AAG CAT CTT TGG
Lys Glu Thr Glu Gln Gly Ser Tyr Thr Val Asn Arg Phe Val Glu Thr>
___b___b____RECOMBINANT LEUKOTOXIN PEPTIDE [SPLIT]_b___b___b___>

        1930       1940        1950        1960
    *     *     *     *     *     *     *     *     *
GGT AAA GCA CTA CAC GAA GTG ACT TCA ACC CAT ACC GCA TTA GTG GGC
CCA TTT CGT GAT GTG CTT CAC TGA AGT TGG GTA TGG CGT AAT CAC CCG
Gly Lys Ala Leu His Glu Val Thr Ser Thr His Thr Ala Leu Val Gly>
___b___b____RECOMBINANT LEUKOTOXIN PEPTIDE [SPLIT]_b___b___b___>

1970        1980        1990        2000        2010
 *     *     *     *     *     *     *     *     *     *
AAC CGT GAA GAA AAA ATA GAA TAT CGT CAT AGC AAT AAC CAG CAC CAT
TTG GCA CTT CTT TTT TAT CTT ATA GCA GTA TCG TTA TTG GTC GTG GTA
Asn Arg Glu Glu Lys Ile Glu Tyr Arg His Ser Asn Asn Gln His His>
___b___b____RECOMBINANT LEUKOTOXIN PEPTIDE [SPLIT]_b___b___b___>

  2020        2030        2040        2050        2060
    *     *     *     *     *     *     *     *     *
GCC GGT TAT TAC ACC AAA GAT ACC TTG AAA GCT GTT GAA GAA ATT ATC
CGG CCA ATA ATG TGG TTT CTA TGG AAC TTT CGA CAA CTT CTT TAA TAG
Ala Gly Tyr Tyr Thr Lys Asp Thr Leu Lys Ala Val Glu Glu Ile Ile>
___b___b____RECOMBINANT LEUKOTOXIN PEPTIDE [SPLIT]_b___b___b___>

   2070        2080        2090        2100        2110
*    *     *     *    *     *     *     *     *     *
GGT ACA TCA CAT AAC GAT ATC TTT AAA GGT AGT AAG TTC AAT GAT GCC
CCA TGT AGT GTA TTG CTA TAG AAA TTT CCA TCA TTC AAG TTA CTA CGG
Gly Thr Ser His Asn Asp Ile Phe Lys Gly Ser Lys Phe Asn Asp Ala>
___b___b____RECOMBINANT LEUKOTOXIN PEPTIDE [SPLIT]_b___b___b___>
```

Figure 8-7

```
       2120      2130       2140      2150      2160
  *     *     *     *     *     *     *     *     *     *
TTT AAC GGT GGT GAT GGT GTC GAT ACT ATT GAC GGT AAC GAC GGC AAT
AAA TTG CCA CCA CTA CCA CAG CTA TGA TAA CTG CCA TTG CTG CCG TTA
Phe Asn Gly Gly Asp Gly Val Asp Thr Ile Asp Gly Asn Asp Gly Asn>
___b___b____RECOMBINANT LEUKOTOXIN PEPTIDE [SPLIT]_b___b___b___>

        2170      2180      2190       2200
   *     *     *     *     *     *     *     *     *
GAC CGC TTA TTT GGT GGT AAA GGC GAT GAT ATT CTC GAT GGT GGA AAT
CTG GCG AAT AAA CCA CCA TTT CCG CTA CTA TAA GAG CTA CCA CCT TTA
Asp Arg Leu Phe Gly Gly Lys Gly Asp Asp Ile Leu Asp Gly Gly Asn>
___b___b____RECOMBINANT LEUKOTOXIN PEPTIDE [SPLIT]_b___b___b___>

2210      2220       2230      2240      2250
 *     *     *     *     *     *     *     *     *     *
GGT GAT GAT TTT ATC GAT GGC GGT AAA GGC AAC GAC CTA TTA CAC GGT
CCA CTA CTA AAA TAG CTA CCG CCA TTT CCG TTG CTG GAT AAT GTG CCA
Gly Asp Asp Phe Ile Asp Gly Gly Lys Gly Asn Asp Leu Leu His Gly>
___b___b____RECOMBINANT LEUKOTOXIN PEPTIDE [SPLIT]_b___b___b___>

 2260      2270      2280       2290      2300
   *     *     *     *     *     *     *     *     *
GGC AAG GGC GAT GAT ATT TTC GTT CAC CGT AAA GGC GAT GGT AAT GAT
CCG TTC CCG CTA CTA TAA AAG CAA GTG GCA TTT CCG CTA CCA TTA CTA
Gly Lys Gly Asp Asp Ile Phe Val His Arg Lys Gly Asp Gly Asn Asp>
___b___b____RECOMBINANT LEUKOTOXIN PEPTIDE [SPLIT]_b___b___b___>

   2310       2320      2330      2340       2350
 *     *     *     *     *     *     *     *     *     *
ATT ATT ACC GAT TCT GAC GGC AAT GAT AAA TTA TCA TTC TCT GAT TCG
TAA TAA TGG CTA AGA CTG CCG TTA CTA TTT AAT AGT AAG AGA CTA AGC
Ile Ile Thr Asp Ser Asp Gly Asn Asp Lys Leu Ser Phe Ser Asp Ser>
___b___b____RECOMBINANT LEUKOTOXIN PEPTIDE [SPLIT]_b___b___b___>

       2360      2370       2380      2390      2400
  *     *     *     *     *     *     *     *     *     *
AAC TTA AAA GAT TTA ACA TTT GAA AAA GTT AAA CAT AAT CTT GTC ATC
TTG AAT TTT CTA AAT TGT AAA CTT TTT CAA TTT GTA TTA GAA CAG TAG
Asn Leu Lys Asp Leu Thr Phe Glu Lys Val Lys His Asn Leu Val Ile>
___b___b____RECOMBINANT LEUKOTOXIN PEPTIDE [SPLIT]_b___b___b___>

        2410      2420      2430       2440
   *     *     *     *     *     *     *     *     *
ACG AAT AGC AAA AAA GAG AAA GTG ACC ATT CAA AAC TGG TTC CGA GAG
TGC TTA TCG TTT TTT CTC TTT CAC TGG TAA GTT TTG ACC AAG GCT CTC
Thr Asn Ser Lys Lys Glu Lys Val Thr Ile Gln Asn Trp Phe Arg Glu>
___b___b____RECOMBINANT LEUKOTOXIN PEPTIDE [SPLIT]_b___b___b___>
```

Figure 8-8

```
2450       2460            2470         2480          2490
 *     *     *     *     *     *     *     *     *     *
GCT GAT TTT GCT AAA GAA GTG CCT AAT TAT AAA GCA ACT AAA GAT GAG
CGA CTA AAA CGA TTT CTT CAC GGA TTA ATA TTT CGT TGA TTT CTA CTC
Ala Asp Phe Ala Lys Glu Val Pro Asn Tyr Lys Ala Thr Lys Asp Glu>
___b___b____RECOMBINANT LEUKOTOXIN PEPTIDE [SPLIT]_b___b___b___>

  2500       2510       2520        2530        2540
    *     *     *     *     *     *     *     *     *
AAA ATC GAA GAA ATC ATC GGT CAA AAT GGC GAG CGG ATC ACC TCA AAG
TTT TAG CTT CTT TAG TAG CCA GTT TTA CCG CTC GCC TAG TGG AGT TTC
Lys Ile Glu Glu Ile Ile Gly Gln Asn Gly Glu Arg Ile Thr Ser Lys>
___b___b____RECOMBINANT LEUKOTOXIN PEPTIDE [SPLIT]_b___b___b___>

   2550        2560       2570        2580        2590
 *     *     *     *     *     *     *     *     *     *
CAA GTT GAT GAT CTT ATC GCA AAA GGT AAC GGC AAA ATT ACC CAA GAT
GTT CAA CTA CTA GAA TAG CGT TTT CCA TTG CCG TTT TAA TGG GTT CTA
Gln Val Asp Asp Leu Ile Ala Lys Gly Asn Gly Lys Ile Thr Gln Asp>
___b___b____RECOMBINANT LEUKOTOXIN PEPTIDE [SPLIT]_b___b___b___>

      2600       2610        2620       2630       2640
   *     *     *     *     *     *     *     *     *     *
GAG CTA TCA AAA GTT GTT GAT AAC TAT GAA TTG CTC AAA CAT AGC AAA
CTC GAT AGT TTT CAA CAA CTA TTG ATA CTT AAC GAG TTT GTA TCG TTT
Glu Leu Ser Lys Val Val Asp Asn Tyr Glu Leu Leu Lys His Ser Lys>
___b___b____RECOMBINANT LEUKOTOXIN PEPTIDE [SPLIT]_b___b___b___>

         2650       2660        2670       2680
      *     *     *     *     *     *     *     *     *
AAT GTG ACA AAC AGC TTA GAT AAG TTA ATC TCA TCT GTA AGT GCA TTT
TTA CAC TGT TTG TCG AAT CTA TTC AAT TAG AGT AGA CAT TCA CGT AAA
Asn Val Thr Asn Ser Leu Asp Lys Leu Ile Ser Ser Val Ser Ala Phe>
___b___b____RECOMBINANT LEUKOTOXIN PEPTIDE [SPLIT]_b___b___b___>

2690       2700         2710        2720       2730
 *     *     *     *     *     *     *     *     *     *
ACC TCG TCT AAT GAT TCG AGA AAT GTA TTA GTG GCT CCA ACT TCA ATG
TGG AGC AGA TTA CTA AGC TCT TTA CAT AAT CAC CGA GGT TGA AGT TAC
Thr Ser Ser Asn Asp Ser Arg Asn Val Leu Val Ala Pro Thr Ser Met>
___b___b____RECOMBINANT LEUKOTOXIN PEPTIDE [SPLIT]_b___b___b___>
```

Figure 8-9

```
 2740      2750      2760       2770       2780
    *    *    *    *    *    *    *    *    *
TTG GAT CAA AGT TTA TCT TCT CTT CAA TTT GCT AGG GGA TCT CAG CAT
AAC CTA GTT TCA AAT AGA AGA GAA GTT AAA CGA TCC CCT AGA GTC GTA
                                                        Gln His>
                                                        ___a___>
Leu Asp Gln Ser Leu Ser Ser Leu Gln Phe Ala Arg Gly Ser>
___b____RECOMBINANT LEUKOTOXIN PEPTIDE [SPLIT]_b___b___>

  2790      2800       2810
*    *    *    *    *    *    *
TGG AGC TAC GGC CTG CGC CCT GGC TAA GGATCC
ACC TCG ATG CCG GAC GCG GGA CCG ATT CCTAGG
Trp Ser Tyr Gly Leu Arg Pro Gly End>
___a___a___a___GNRH____a___a___a___>
```

Figure 8-10 tac = hybrid trp::lac promoter from E. coli
bla = beta lactamase gene (ampicillin resistance)
lktA = Pasteurella haemolytica structural gene
VP4= Bovine rotavirus VP4(232 - 255) gene
lacI = E. coli lac operon repressor

```
                10          20          30          40
         *      *    *      *     *     *     *     *     *
ATG GCT ACT GTT ATA GAT CTA AGC TTC CCA AAA ACT GGG GCA AAA AAA
TAC CGA TGA CAA TAT CTA GAT TCG AAG GGT TTT TGA CCC CGT TTT TTT
Met Ala Thr Val Ile Asp Leu Ser Phe Pro Lys Thr Gly Ala Lys Lys>
___b___b____RECOMBINANT LEUKOTOXIN PEPTIDE [SPLIT]_b___b___b___>

50          60          70          80          90
 *     *    *     *     *     *     *     *     *     *
ATT ATC CTC TAT ATT CCC CAA AAT TAC CAA TAT GAT ACT GAA CAA GGT
TAA TAG GAG ATA TAA GGG GTT TTA ATG GTT ATA CTA TGA CTT GTT CCA
Ile Ile Leu Tyr Ile Pro Gln Asn Tyr Gln Tyr Asp Thr Glu Gln Gly>
___b___b____RECOMBINANT LEUKOTOXIN PEPTIDE [SPLIT]_b___b___b___>

  100         110         120         130         140
    *     *     *     *     *     *     *     *     *
AAT GGT TTA CAG GAT TTA GTC AAA GCG GCC GAA GAG TTG GGG ATT GAG
TTA CCA AAT GTC CTA AAT CAG TTT CGC CGG CTT CTC AAC CCC TAA CTC
Asn Gly Leu Gln Asp Leu Val Lys Ala Ala Glu Glu Leu Gly Ile Glu>
___b___b____RECOMBINANT LEUKOTOXIN PEPTIDE [SPLIT]_b___b___b___>

    150         160         170         180         190
*     *     *     *     *     *     *     *     *     *
GTA CAA AGA GAA GAA CGC AAT AAT ATT GCA ACA GCT CAA ACC AGT TTA
CAT GTT TCT CTT CTT GCG TTA TTA TAA CGT TGT CGA GTT TGG TCA AAT
Val Gln Arg Glu Glu Arg Asn Asn Ile Ala Thr Ala Gln Thr Ser Leu>
___b___b____RECOMBINANT LEUKOTOXIN PEPTIDE [SPLIT]_b___b___b___>

        200         210         220         230         240
  *     *     *     *     *     *     *     *     *     *
GGC ACG ATT CAA ACC GCT ATT GGC TTA ACT GAG CGT GGC ATT GTG TTA
CCG TGC TAA GTT TGG CGA TAA CCG AAT TGA CTC GCA CCG TAA CAC AAT
Gly Thr Ile Gln Thr Ala Ile Gly Leu Thr Glu Arg Gly Ile Val Leu>
___b___b____RECOMBINANT LEUKOTOXIN PEPTIDE [SPLIT]_b___b___b___>
```

Figure 10-1

```
              250          260          270           280
          *          *    *     *     *     *     *     *     *
TCC GCT CCA CAA ATT GAT AAA TTG CTA CAG AAA ACT AAA GCA GGC CAA
AGG CGA GGT GTT TAA CTA TTT AAC GAT GTC TTT TGA TTT CGT CCG GTT
Ser Ala Pro Gln Ile Asp Lys Leu Leu Gln Lys Thr Lys Ala Gly Gln>
___b___b____RECOMBINANT LEUKOTOXIN PEPTIDE [SPLIT]_b___b___b___>

290         300          310          320          330
 *     *     *     *     *     *     *     *     *     *
GCA TTA GGT TCT GCC GAA AGC ATT GTA CAA AAT GCA AAT AAA GCC AAA
CGT AAT CCA AGA CGG CTT TCG TAA CAT GTT TTA CGT TTA TTT CGG TTT
Ala Leu Gly Ser Ala Glu Ser Ile Val Gln Asn Ala Asn Lys Ala Lys>
___b___b____RECOMBINANT LEUKOTOXIN PEPTIDE [SPLIT]_b___b___b___>

   340         350          360           370         380
     *     *     *     *     *     *     *     *     *
ACT GTA TTA TCT GGC ATT CAA TCT ATT TTA GGC TCA GTA TTG GCT GGA
TGA CAT AAT AGA CCG TAA GTT AGA TAA AAT CCG AGT CAT AAC CGA CCT
Thr Val Leu Ser Gly Ile Gln Ser Ile Leu Gly Ser Val Leu Ala Gly>
___b___b____RECOMBINANT LEUKOTOXIN PEPTIDE [SPLIT]_b___b___b___>

     390          400          410          420          430
 *     *     *     *     *     *     *     *     *     *
ATG GAT TTA GAT GAG GCC TTA CAG AAT AAC AGC AAC CAA CAT GCT CTT
TAC CTA AAT CTA CTC CGG AAT GTC TTA TTG TCG TTG GTT GTA CGA GAA
Met Asp Leu Asp Glu Ala Leu Gln Asn Asn Ser Asn Gln His Ala Leu>
___b___b____RECOMBINANT LEUKOTOXIN PEPTIDE [SPLIT]_b___b___b___>

        440          450           460          470         480
  *      *     *     *     *     *     *     *     *     *
GCT AAA GCT GGC TTG GAG CTA ACA AAT TCA TTA ATT GAA AAT ATT GCT
CGA TTT CGA CCG AAC CTC GAT TGT TTA AGT AAT TAA CTT TTA TAA CGA
Ala Lys Ala Gly Leu Glu Leu Thr Asn Ser Leu Ile Glu Asn Ile Ala>
___b___b____RECOMBINANT LEUKOTOXIN PEPTIDE [SPLIT]_b___b___b___>

              490          500          510           520
      *     *     *     *     *     *     *     *     *
AAT TCA GTA AAA ACA CTT GAC GAA TTN -GT GAG CAA ATT AGT CAA TTT
TTA AGT CAT TTT TGT GAA CTG CTT AAN -CA CTC GTT TAA TCA GTT AAA
Asn Ser Val Lys Thr Leu Asp Glu Xxx Cys Glu Gln Ile Ser Gln Phe>
___b___b____RECOMBINANT LEUKOTOXIN PEPTIDE [SPLIT]_b___b___b___>

530         540          550          560          570
 *     *     *     *     *     *     *     *     *     *
GGT TCA AAA CTA CAA AAT ATC AAA GGC TTA GGG ACT TTA GGA GAC AAA
CCA AGT TTT GAT GTT TTA TAG TTT CCG AAT CCC TGA AAT CCT CTG TTT
Gly Ser Lys Leu Gln Asn Ile Lys Gly Leu Gly Thr Leu Gly Asp Lys>
___b___b____RECOMBINANT LEUKOTOXIN PEPTIDE [SPLIT]_b___b___b___>
```

Figure 10-2

```
         580         590         600         610         620
           *     *     *     *     *     *     *     *     *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
___b___b____RECOMBINANT LEUKOTOXIN PEPTIDE [SPLIT]_b___b___b___>

        630         640         650         660         670
*     *     *     *     *     *     *     *     *     *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
___b___b____RECOMBINANT LEUKOTOXIN PEPTIDE [SPLIT]_b___b___b___>

           680         690         700         710         720
  *     *     *     *     *     *     *     *     *     *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
___b___b____RECOMBINANT LEUKOTOXIN PEPTIDE [SPLIT]_b___b___b___>

              730         740         750         760
     *     *     *     *     *     *     *     *     *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
___b___b____RECOMBINANT LEUKOTOXIN PEPTIDE [SPLIT]_b___b___b___>

770         780         790         800         810
 *     *     *     *     *     *     *     *     *     *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
___b___b____RECOMBINANT LEUKOTOXIN PEPTIDE [SPLIT]_b___b___b___>

     820         830         840         850         860
       *     *     *     *     *     *     *     *     *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
___b___b____RECOMBINANT LEUKOTOXIN PEPTIDE [SPLIT]_b___b___b___>
```

Figure 10-3

```
     870         880         890         900         910
*     *     *     *     *     *     *     *     *     *
GGT ATT GCC GAT AAA TTT AAT CAT GCA AAA AGT TTA GAG AGT TAT GCC
CCA TAA CGG CTA TTT AAA TTA GTA CGT TTT TCA AAT CTC TCA ATA CGG
Gly Ile Ala Asp Lys Phe Asn His Ala Lys Ser Leu Glu Ser Tyr Ala>
___b___b____RECOMBINANT LEUKOTOXIN PEPTIDE [SPLIT]_b___b___b___>

         920         930         940         950         960
   *     *     *     *     *     *     *     *     *     *
GAA CGC TTT AAA AAA TTA GGC TAT GAC GGA GAT AAT TTA TTA GCA GAA
CTT GCG AAA TTT TTT AAT CCG ATA CTG CCT CTA TTA AAT AAT CGT CTT
Glu Arg Phe Lys Lys Leu Gly Tyr Asp Gly Asp Asn Leu Leu Ala Glu>
___b___b____RECOMBINANT LEUKOTOXIN PEPTIDE [SPLIT]_b___b___b___>

             970         980         990        1000
       *     *     *     *     *     *     *     *     *
TAT CAG CGG GGA ACA GGG ACT ATT GAT GCA TCG GTT ACT GCA ATT AAT
ATA GTC GCC CCT TGT CCC TGA TAA CTA CGT AGC CAA TGA CGT TAA TTA
Tyr Gln Arg Gly Thr Gly Thr Ile Asp Ala Ser Val Thr Ala Ile Asn>
___b___b____RECOMBINANT LEUKOTOXIN PEPTIDE [SPLIT]_b___b___b___>

1010        1020        1030        1040        1050
  *     *     *     *     *     *     *     *     *     *
ACC GCA TTG GCC GCT ATT GCT GGT GGT GTG TCT GCT GCT GCA GCC GGC
TGG CGT AAC CGG CGA TAA CGA CCA CCA CAC AGA CGA CGA CGT CGG CCG
Thr Ala Leu Ala Ala Ile Ala Gly Gly Val Ser Ala Ala Ala Ala Gly>
___b___b____RECOMBINANT LEUKOTOXIN PEPTIDE [SPLIT]_b___b___b___>

 1060        1070        1080        1090        1100
     *     *     *     *     *     *     *     *     *
TCG GTT ATT GCT TCA CCG ATT GCC TTA TTA GTA TCT GGG ATT ACC GGT
AGC CAA TAA CGA AGT GGC TAA CGG AAT AAT CAT AGA CCC TAA TGG CCA
Ser Val Ile Ala Ser Pro Ile Ala Leu Leu Val Ser Gly Ile Thr Gly>
___b___b____RECOMBINANT LEUKOTOXIN PEPTIDE [SPLIT]_b___b___b___>

     1110        1120        1130        1140        1150
*     *     *     *     *     *     *     *     *     *
GTA ATT TCT ACG ATT CTG CAA TAT TCT AAA CAA GCA ATG TTT GAG CAC
CAT TAA AGA TGC TAA GAC GTT ATA AGA TTT GTT CGT TAC AAA CTC GTG
Val Ile Ser Thr Ile Leu Gln Tyr Ser Lys Gln Ala Met Phe Glu His>
___b___b____RECOMBINANT LEUKOTOXIN PEPTIDE [SPLIT]_b___b___b___>

        1160        1170        1180        1190        1200
   *     *     *     *     *     *     *     *     *     *
GTT GCA AAT AAA ATT CAT AAC AAA ATT GTA GAA TGG GAA AAA AAT AAT
CAA CGT TTA TTT TAA GTA TTG TTT TAA CAT CTT ACC CTT TTT TTA TTA
Val Ala Asn Lys Ile His Asn Lys Ile Val Glu Trp Glu Lys Asn Asn>
___b___b____RECOMBINANT LEUKOTOXIN PEPTIDE [SPLIT]_b___b___b___>
```

Figure 10-4

```
             1210        1220        1230         1240
        *     *    *     *     *    *     *     *    *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___b___b____RECOMBINANT LEUKOTOXIN PEPTIDE [SPLIT]_b___b___b___>

1250          1260        1270       1280       1290
  *     *     *     *     *     *    *     *     *     *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___b___b____RECOMBINANT LEUKOTOXIN PEPTIDE [SPLIT]_b___b___b___>

  1300        1310        1320        1330        1340
    *     *     *     *     *     *     *     *     *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___b___b____RECOMBINANT LEUKOTOXIN PEPTIDE [SPLIT]_b___b___b___>

    1350        1360        1370        1380        1390
*     *     *     *     *     *     *     *     *     *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___b___b____RECOMBINANT LEUKOTOXIN PEPTIDE [SPLIT]_b___b___b___>

       1400        1410        1420        1430        1440
  *     *     *     *     *     *     *     *     *     *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___b___b____RECOMBINANT LEUKOTOXIN PEPTIDE [SPLIT]_b___b___b___>

            1450        1460        1470         1480
       *     *    *     *     *    *     *     *    *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___b___b____RECOMBINANT LEUKOTOXIN PEPTIDE [SPLIT]_b___b___b___>
```

Figure 10-5

```
1490       1500        1510        1520        1530
  *     *     *     *     *     *     *     *     *     *
AAT TCG GGT AAA GCG AAA ACT CAG CAT ATC TTA TTC AGA ACG CCA TTA
TTA AGC CCA TTT CGC TTT TGA GTC GTA TAG AAT AAG TCT TGC GGT AAT
Asn Ser Gly Lys Ala Lys Thr Gln His Ile Leu Phe Arg Thr Pro Leu>
___b___b____RECOMBINANT LEUKOTOXIN PEPTIDE [SPLIT]_b___b___b___>

  1540        1550        1560        1570        1580
      *     *     *     *     *     *     *     *     *
TTG ACG CCG GGA ACA GAG CAT CGT GAA CGC GTA CAA ACA GGT AAA TAT
AAC TGC GGC CCT TGT CTC GTA GCA CTT GCG CAT GTT TGT CCA TTT ATA
Leu Thr Pro Gly Thr Glu His Arg Glu Arg Val Gln Thr Gly Lys Tyr>
___b___b____RECOMBINANT LEUKOTOXIN PEPTIDE [SPLIT]_b___b___b___>

    1590        1600        1610        1620        1630
  *     *     *     *     *     *     *     *     *     *
GAA TAT ATT ACC AAG CTC AAT ATT AAC CGT GTA GAT AGC TGG AAA ATT
CTT ATA TAA TGG TTC GAG TTA TAA TTG GCA CAT CTA TCG ACC TTT TAA
Glu Tyr Ile Thr Lys Leu Asn Ile Asn Arg Val Asp Ser Trp Lys Ile>
___b___b____RECOMBINANT LEUKOTOXIN PEPTIDE [SPLIT]_b___b___b___>

       1640        1650        1660        1670        1680
    *     *     *     *     *     *     *     *     *     *
ACA GAT GGT GCA GCA AGT TCT ACC TTT GAT TTA ACT AAC GTT GTT CAG
TGT CTA CCA CGT CGT TCA AGA TGG AAA CTA AAT TGA TTG CAA CAA GTC
Thr Asp Gly Ala Ala Ser Ser Thr Phe Asp Leu Thr Asn Val Val Gln>
___b___b____RECOMBINANT LEUKOTOXIN PEPTIDE [SPLIT]_b___b___b___>

          1690        1700        1710        1720
      *     *     *     *     *     *     *     *     *
CGT ATT GGT ATT GAA TTA GAC AAT GCT GGA AAT GTA ACT AAA ACC AAA
GCA TAA CCA TAA CTT AAT CTG TTA CGA CCT TTA CAT TGA TTT TGG TTT
Arg Ile Gly Ile Glu Leu Asp Asn Ala Gly Asn Val Thr Lys Thr Lys>
___b___b____RECOMBINANT LEUKOTOXIN PEPTIDE [SPLIT]_b___b___b___>

1730        1740        1750        1760        1770
  *     *     *     *     *     *     *     *     *     *
GAA ACA AAA ATT ATT GCC AAA CTT GGT GAA GGT GAT GAC AAC GTA TTT
CTT TGT TTT TAA TAA CGG TTT GAA CCA CTT CCA CTA CTG TTG CAT AAA
Glu Thr Lys Ile Ile Ala Lys Leu Gly Glu Gly Asp Asp Asn Val Phe>
___b___b____RECOMBINANT LEUKOTOXIN PEPTIDE [SPLIT]_b___b___b___>

  1780        1790        1800        1810        1820
      *     *     *     *     *     *     *     *     *
GTT GGT TCT GGT ACG ACG GAA ATT GAT GGC GGT GAA GGT TAC GAC CGA
CAA CCA AGA CCA TGC TGC CTT TAA CTA CCG CCA CTT CCA ATG CTG GCT
Val Gly Ser Gly Thr Thr Glu Ile Asp Gly Gly Glu Gly Tyr Asp Arg>
___b___b____RECOMBINANT LEUKOTOXIN PEPTIDE [SPLIT]_b___b___b___>
```

Figure 10-6

```
  1830       1840       1850       1860       1870
*   *    *    *    *    *    *    *    *    *
GTT CAC TAT AGC CGT GGA AAC TAT GGT GCT TTA ACT ATT GAT GCA ACC
CAA GTG ATA TCG GCA CCT TTG ATA CCA CGA AAT TGA TAA CTA CGT TGG
Val His Tyr Ser Arg Gly Asn Tyr Gly Ala Leu Thr Ile Asp Ala Thr>
___b___b____RECOMBINANT LEUKOTOXIN PEPTIDE [SPLIT]_b___b___b___>

     1880       1890       1900       1910       1920
  *    *    *    *    *    *    *    *    *    *
AAA GAG ACC GAG CAA GGT AGT TAT ACC GTA AAT CGT TTC GTA GAA ACC
TTT CTC TGG CTC GTT CCA TCA ATA TGG CAT TTA GCA AAG CAT CTT TGG
Lys Glu Thr Glu Gln Gly Ser Tyr Thr Val Asn Arg Phe Val Glu Thr>
___b___b____RECOMBINANT LEUKOTOXIN PEPTIDE [SPLIT]_b___b___b___>

        1930       1940       1950       1960
    *    *    *    *    *    *    *    *    *
GGT AAA GCA CTA CAC GAA GTG ACT TCA ACC CAT ACC GCA TTA GTG GGC
CCA TTT CGT GAT GTG CTT CAC TGA AGT TGG GTA TGG CGT AAT CAC CCG
Gly Lys Ala Leu His Glu Val Thr Ser Thr His Thr Ala Leu Val Gly>
___b___b____RECOMBINANT LEUKOTOXIN PEPTIDE [SPLIT]_b___b___b___>

1970        1980       1990       2000       2010
 *      *     *    *    *    *    *    *    *    *
AAC CGT GAA GAA AAA ATA GAA TAT CGT CAT AGC AAT AAC CAG CAC CAT
TTG GCA CTT CTT TTT TAT CTT ATA GCA GTA TCG TTA TTG GTC GTG GTA
Asn Arg Glu Glu Lys Ile Glu Tyr Arg His Ser Asn Asn Gln His His>
___b___b____RECOMBINANT LEUKOTOXIN PEPTIDE [SPLIT]_b___b___b___>

 2020       2030       2040       2050       2060
    *    *    *    *    *    *    *    *    *
GCC GGT TAT TAC ACC AAA GAT ACC TTG AAA GCT GTT GAA GAA ATT ATC
CGG CCA ATA ATG TGG TTT CTA TGG AAC TTT CGA CAA CTT CTT TAA TAG
Ala Gly Tyr Tyr Thr Lys Asp Thr Leu Lys Ala Val Glu Glu Ile Ile>
___b___b____RECOMBINANT LEUKOTOXIN PEPTIDE [SPLIT]_b___b___b___>

  2070       2080       2090       2100       2110
*   *    *    *    *    *    *    *    *    *
GGT ACA TCA CAT AAC GAT ATC TTT AAA GGT AGT AAG TTC AAT GAT GCC
CCA TGT AGT GTA TTG CTA TAG AAA TTT CCA TCA TTC AAG TTA CTA CGG
Gly Thr Ser His Asn Asp Ile Phe Lys Gly Ser Lys Phe Asn Asp Ala>
___b___b____RECOMBINANT LEUKOTOXIN PEPTIDE [SPLIT]_b___b___b___>
```

Figure 10-7

```
      2120        2130          2140        2150        2160
 *     *     *     *      *     *     *     *     *     *
TTT AAC GGT GGT GAT GGT GTC GAT ACT ATT GAC GGT AAC GAC GGC AAT
AAA TTG CCA CCA CTA CCA CAG CTA TGA TAA CTG CCA TTG CTG CCG TTA
Phe Asn Gly Gly Asp Gly Val Asp Thr Ile Asp Gly Asn Asp Gly Asn>
___b___b____RECOMBINANT LEUKOTOXIN PEPTIDE [SPLIT]_b___b___b___>

         2170        2180        2190        2200
    *     *     *     *     *     *     *     *     *
GAC CGC TTA TTT GGT GGT AAA GGC GAT GAT ATT CTC GAT GGT GGA AAT
CTG GCG AAT AAA CCA CCA TTT CCG CTA CTA TAA GAG CTA CCA CCT TTA
Asp Arg Leu Phe Gly Gly Lys Gly Asp Asp Ile Leu Asp Gly Gly Asn>
___b___b____RECOMBINANT LEUKOTOXIN PEPTIDE [SPLIT]_b___b___b___>

2210        2220        2230        2240        2250
 *     *     *     *     *     *     *     *     *     *
GGT GAT GAT TTT ATC GAT GGC GGT AAA GGC AAC GAC CTA TTA CAC GGT
CCA CTA CTA AAA TAG CTA CCG CCA TTT CCG TTG CTG GAT AAT GTG CCA
Gly Asp Asp Phe Ile Asp Gly Gly Lys Gly Asn Asp Leu Leu His Gly>
___b___b____RECOMBINANT LEUKOTOXIN PEPTIDE [SPLIT]_b___b___b___>

 2260        2270        2280        2290        2300
  *     *     *     *     *     *     *     *     *
GGC AAG GGC GAT GAT ATT TTC GTT CAC CGT AAA GGC GAT GGT AAT GAT
CCG TTC CCG CTA CTA TAA AAG CAA GTG GCA TTT CCG CTA CCA TTA CTA
Gly Lys Gly Asp Asp Ile Phe Val His Arg Lys Gly Asp Gly Asn Asp>
___b___b____RECOMBINANT LEUKOTOXIN PEPTIDE [SPLIT]_b___b___b___>

   2310        2320        2330        2340        2350
 *     *     *     *     *     *     *     *     *     *
ATT ATT ACC GAT TCT GAC GGC AAT GAT AAA TTA TCA TTC TCT GAT TCG
TAA TAA TGG CTA AGA CTG CCG TTA CTA TTT AAT AGT AAG AGA CTA AGC
Ile Ile Thr Asp Ser Asp Gly Asn Asp Lys Leu Ser Phe Ser Asp Ser>
___b___b____RECOMBINANT LEUKOTOXIN PEPTIDE [SPLIT]_b___b___b___>

      2360        2370        2380        2390        2400
 *     *     *     *     *     *     *     *     *     *
AAC TTA AAA GAT TTA ACA TTT GAA AAA GTT AAA CAT AAT CTT GTC ATC
TTG AAT TTT CTA AAT TGT AAA CTT TTT CAA TTT GTA TTA GAA CAG TAG
Asn Leu Lys Asp Leu Thr Phe Glu Lys Val Lys His Asn Leu Val Ile>
___b___b____RECOMBINANT LEUKOTOXIN PEPTIDE [SPLIT]_b___b___b___>

         2410        2420        2430        2440
    *     *     *     *     *     *     *     *     *
ACG AAT AGC AAA AAA GAG AAA GTG ACC ATT CAA AAC TGG TTC CGA GAG
TGC TTA TCG TTT TTT CTC TTT CAC TGG TAA GTT TTG ACC AAG GCT CTC
Thr Asn Ser Lys Lys Glu Lys Val Thr Ile Gln Asn Trp Phe Arg Glu>
___b___b____RECOMBINANT LEUKOTOXIN PEPTIDE [SPLIT]_b___b___b___>
```

Figure 10-8

```
2450          2460          2470          2480          2490
  *       *      *      *      *      *      *      *      *      *
GCT GAT TTT GCT AAA GAA GTG CCT AAT TAT AAA GCA ACT AAA GAT GAG
CGA CTA AAA CGA TTT CTT CAC GGA TTA ATA TTT CGT TGA TTT CTA CTC
Ala Asp Phe Ala Lys Glu Val Pro Asn Tyr Lys Ala Thr Lys Asp Glu>
___b___b____RECOMBINANT LEUKOTOXIN PEPTIDE [SPLIT]_b___b___b___>

   2500          2510          2520          2530          2540
     *      *      *      *      *      *      *      *      *
AAA ATC GAA GAA ATC ATC GGT CAA AAT GGC GAG CGG ATC ACC TCA AAG
TTT TAG CTT CTT TAG TAG CCA GTT TTA CCG CTC GCC TAG TGG AGT TTC
Lys Ile Glu Glu Ile Ile Gly Gln Asn Gly Glu Arg Ile Thr Ser Lys>
___b___b____RECOMBINANT LEUKOTOXIN PEPTIDE [SPLIT]_b___b___b___>

     2550          2560          2570          2580          2590
*      *      *      *      *      *      *      *      *      *
CAA GTT GAT GAT CTT ATC GCA AAA GGT AAC GGC AAA ATT ACC CAA GAT
GTT CAA CTA CTA GAA TAG CGT TTT CCA TTG CCG TTT TAA TGG GTT CTA
Gln Val Asp Asp Leu Ile Ala Lys Gly Asn Gly Lys Ile Thr Gln Asp>
___b___b____RECOMBINANT LEUKOTOXIN PEPTIDE [SPLIT]_b___b___b___>

        2600          2610          2620          2630          2640
  *      *      *      *      *      *      *      *      *      *
GAG CTA TCA AAA GTT GTT GAT AAC TAT GAA TTG CTC AAA CAT AGC AAA
CTC GAT AGT TTT CAA CAA CTA TTG ATA CTT AAC GAG TTT GTA TCG TTT
Glu Leu Ser Lys Val Val Asp Asn Tyr Glu Leu Leu Lys His Ser Lys>
___b___b____RECOMBINANT LEUKOTOXIN PEPTIDE [SPLIT]_b___b___b___>

           2650          2660          2670          2680
     *      *      *      *      *      *      *      *      *
AAT GTG ACA AAC AGC TTA GAT AAG TTA ATC TCA TCT GTA AGT GCA TTT
TTA CAC TGT TTG TCG AAT CTA TTC AAT TAG AGT AGA CAT TCA CGT AAA
Asn Val Thr Asn Ser Leu Asp Lys Leu Ile Ser Ser Val Ser Ala Phe>
___b___b____RECOMBINANT LEUKOTOXIN PEPTIDE [SPLIT]_b___b___b___>

2690          2700          2710          2720          2730
  *      *      *      *      *      *      *      *      *      *
ACC TCG TCT AAT GAT TCG AGA AAT GTA TTA GTG GCT CCA ACT TCA ATG
TGG AGC AGA TTA CTA AGC TCT TTA CAT AAT CAC CGA GGT TGA AGT TAC
Thr Ser Ser Asn Asp Ser Arg Asn Val Leu Val Ala Pro Thr Ser Met>
___b___b____RECOMBINANT LEUKOTOXIN PEPTIDE [SPLIT]_b___b___b___>
```

Figure 10-9

```
 2740       2750       2760        2770       2780
    *    *     *    *     *    *     *    *     *
TTG GAT CAA AGT TTA TCT TCT CTT CAA TTT GCT AGG GGA TCT TGC AAC
AAC CTA GTT TCA AAT AGA AGA GAA GTT AAA CGA TCC CCT AGA ACG TTG
                                                        Cys Asn>
                                                        ___a___>
Leu Asp Gln Ser Leu Ser Ser Leu Gln Phe Ala Arg Gly Ser>
___b____RECOMBINANT LEUKOTOXIN PEPTIDE [SPLIT]_b___b___>

   2790        2800       2810       2820        2830
*    *     *     *    *     *     *    *     *     *
ATT GTG CCT GTG AGC ATT GTG AGC CGC AAC ATT GTG TAC ACC CGC GCG
TAA CAC GGA CAC TCG TAA CAC TCG GCG TTG TAA CAC ATG TGG GCG CGC
Ile Val Pro Val Ser Ile Val Ser Arg Asn Ile Val Tyr Thr Arg Ala>
___a___a___a___a___a___a___a_¦VP4__a___a___a___a___a___a___a___>

     2840       2850       2860
  *     *     *    *     *    *
CAA CCT AAC CAA GAC ATT GTG TAG GATCC
GTT GGA TTG GTT CTG TAA CAC ATC CTAGG
Gln Pro Asn Gln Asp Ile Val End>
___a___a___a_¦VP4__a___a___a___>
```

Figure 10-10

ENHANCED IMMUNOGENICITY USING LEUKOTOXIN CHIMERAS

CROSS-REFERENCE TO RELATED APPLICATION

This application is a continuation-in-part of U.S. patent application Ser. No. 07/779,171, filed 16 Oct. 1991, now abandoned, from which priority is claimed pursuant to 35 USC §120 and which is hereby incorporated by reference in its entirety.

TECHNICAL FIELD

The present invention relates generally to immunological carrier systems. More particularly, the invention pertains to leukotoxin-antigen chimeras which demonstrate enhanced immunogenicity as compared to the immunogenicity of the antigen alone.

BACKGROUND OF THE INVENTION

Subunit vaccines are vaccines which are devoid of intact pathogen cells. These vaccines are usually composed of substantially purified antigens. Such vaccines are generally preferable to compositions which use attenuated or inactivated pathogens. However, many subunit vaccines which include proteins, such as peptide hormones and bacterial and viral antigens, require the help of a carrier protein in order to elicit a strong immune response. This is especially true for small proteins or endogenous substances, such as hormones, which are poorly immunogenic.

The carrier serves to non-specifically stimulate T helper cell activity and to direct the antigen to the antigen presenting cell, where the antigen is processed and presented at the cell surface in the context of molecules of the major histocompatibility complex (MHC).

Several carrier systems have been developed for this purpose. For example, small peptide antigens are often coupled to protein carriers such as keyhole limpet haemocyanin (Bittle, J. L., et al., *Nature* (1982) 298:30–33), tetanus toxoid (Muller, G., et al., *Proc. Natl. Acad. Sci. U.S.A.* (1982) 79:569–573), ovalbumin, and sperm whale myoglobin, to produce an immune response. However, carriers may elicit strong immunity not relevant to the peptide antigen and this may inhibit the immune response to the peptide vaccine on secondary immunization (Schutze, M. P., et al, *J. Immun.* (1985) 135:2319–2322).

Antigen delivery systems have also been based on particulate carriers. For example, preformed particles have been used as platforms onto which antigens can be coupled and incorporated. Systems based on proteosomes (Lowell, G. H., et al., *Science* (1988) 240:800–802), immune stimulatory complexes (Morein, B., et al., *Nature* (1984) 308:457–460), and viral particles such as HBsAg (Neurath, A. R., et al., *Mol. Immunol.* (1989) 26:53–62) and rotavirus inner capsid protein (Redmond, M. J., et al., *Mol. Immunol.* (1991) 28:269–278) have been developed.

Other carrier systems have been devised using recombinantly produced chimeric proteins that self assemble into particles. For example, the yeast retrotransposon, Ty, encodes a series of proteins that assemble into virus like particles (Ty-VLPs; Kingsman, S. M., and A. J. Kingsman *Vacc.* (1988) 6:304–306). Foreign genes have been inserted into the TyA gene and expressed in yeast as a fusion protein. The fusion protein retains the capacity to self assemble into particles of uniform size.

Other chimeric protein particles have been examined such as HBsAg, (Valenzuela, P., et al., *Bio/Technol.* (1985) 3:323–326; U.S. Pat. No. 4,722,840; Delpeyroux, F. N., et al., *Science* (1986) 233:472–475), Hepatitis B core antigen (Clarke, B. E., et al., *Vaccines* 88 (Ed. H. Ginsberg, et al., 1988) pp. 127–131), Poliovirus (Burke, K. L., et al., *Nature* (1988) 332:81–82), and Tobacco Mosaic Virus (Haynes, J. R., et al., *Bio/Technol.* (1986) 4:637–641). However, these carriers are restricted in their usefulness by virtue of the limited size of the active agent which may be inserted into the structural protein without interfering with particle assembly.

Gene fusions provide a convenient method for the production of chimeric proteins. The expression of chimeric proteins affords an efficient means of linking a carrier protein to a desired antigen.

*Pasteurella haemolytica* produces a cytotoxin which is a leukotoxin. See, e.g. Gentry et al. *Vet. Immunology and Immunopathology* (1985) 9:239–250; Shewen, P. E., and Wilkie, B. N. *Infect. Immun.* (1987) 55:3233–3236. The gene encoding this cytotoxin has been cloned and expressed in bacterial cells. Lo et al. *Infect. Immun.* (1985) 50:667–671; U.S. Pat. No. 5,055,400. The leukotoxin has been used as an antigen in vaccine formulations to fight shipping fever pneumonia in livestock (See, e.g. U.S. Pat. No. 4,957,739) as well as to produce chimeric molecules for use in vaccines against shipping fever (see, e.g. International Publication No. WO 92/03558, published 5 Mar. 1992; and U.S. Pat. No. 5,028,423). However, the use of leukotoxin as a carrier molecule to increase the immune response of antigens associated therewith has not heretofore been described.

DISCLOSURE OF THE INVENTION

The present invention is based on the construction of novel gene fusions between the *P. haemolytica* leukotoxin gene and a nucleotide sequence encoding a selected antigen. These constructs produce a chimeric protein that displays enhanced immunogenicity when compared to the immunologic reaction elicited by administration of the antigen alone.

In one embodiment, the present invention is directed to an immunological carrier system comprising an immunogenic chimeric protein. The chimeric protein comprises a leukotoxin polypeptide fused to a selected antigen, whereby the leukotoxin portion of the chimeric protein acts to increase the immunogenicity of the antigen. In particularly preferred embodiments, the selected antigen is somatostatin (SRIF), gonadotropin releasing hormone (GnRH) or rotavirus viral protein 4 (VP4).

Also disclosed are vaccine compositions comprising the chimeric proteins and a pharmaceutically acceptable vehicle and methods of using the same.

In another embodiment, the subject invention is directed to DNA constructs encoding the chimeric proteins. The DNA constructs comprise a first nucleotide sequence encoding a leukotoxin polypeptide operably linked to a second nucleotide sequence encoding the selected antigen.

In yet another embodiment, the subject invention is directed to expression cassettes comprised of (a) the DNA constructs above and (b) control sequences that direct the transcription of the construct whereby the constructs can be transcribed and translated in a host cell.

In another embodiment, the invention is directed to host cells transformed with these expression cassettes.

Another embodiment of the invention provides a method of producing a recombinant polypeptide. The method comprises (a) providing a population of host cells described above and (b) growing the population of cells under conditions whereby the polypeptide encoded by the expression cassette is expressed.

These and other embodiments of the present invention will readily occur to those of ordinary skill in the art in view of the disclosure herein.

BRIEF DESCRIPTION OF THE FIGURES

FIGS. 3-1 to 3-10 shows the nucleotide sequence and predicted amino acid sequence of leukotoxin 352 (LKT 352) from plasmid pAA352 (SEQ ID NO:1). Both the structural gene for LKT 352 and the sequences of the flanking vector regions are shown.

FIG. 4 shows the nucleotide sequences of SRIF, GnRH and bovine rotavirus VP4 (SEQ ID NOS:2-7), used in the construction of the leukotoxin-antigen gene fusions.

FIG. 5 shows the structure of Plasmid pAA496 carrying a leukotoxin-SRIF (LKT-SRIF) gene fusion wherein tac is the hybrid trp::lac promoter from *E. coli*; bla represents the β-lactamase gene (ampicillin resistance); lktA is the *P. haemolytica* leukotoxin structural gene; SRIF is the somatostatin structural gene; and lacl is the *E. coli* lac operon repressor. The direction of transcription/translation of the leukotoxin gene is indicated by the arrow. The size of each component is not drawn to scale.

FIG. 6-1 to 6-10 depicts the nucleotide sequence and predicted amino acid sequence of the LKT-SRIF chimeric protein from pAA496 (SEQ ID NO:8).

FIG. 7 shows the structure of Plasmid pAA502 carrying a leukotoxin-GnRH (LKT-GnRH) gene fusion wherein tac is the hybrid trp::lac promoter from *E. coli*; bla represents the β-lactamase gene (ampicillin resistance); lktA is the *P. haemolytica* leukotoxin structural gene; GnRH is the gonadotropin releasing hormone structural gene; and lacl is the *E. coli* lac operon repressor. The direction of transcription/translation of the leukotoxin gene is indicated by the arrow. The size of each component is not drawn to scale.

FIGS. 8-1 to 8-10 shows the nucleotide sequence and predicted amino acid sequence of the LKT-GnRH chimeric protein from pAA502 (SEQ ID NO:9).

FIG. 9 depicts the structure of Plasmid pAA501 carrying a leukotoxin-VP4 (LKT-VP4) gene, fusion wherein tac is the hybrid trp::lac promoter from *E. coli*; bla represents the β-lactamase gene (ampicillin resistance); lktA is the *P. haemolytica* leukotoxin structural gene; VP4 is the bovine rotavirus viral protein 4 (232–255) structural gene; and lacl is the *E. coli* lac operon repressor. The direction of transcription/translation of the leukotoxin gene is indicated by the arrow. The size of each component is not drawn to scale.

FIGS. 10-1 to 10-10 shows the nucleotide sequence and predicted amino acid sequence of the LKT-VP4 chimeric protein from pAA501 (SEQ ID NO:10).

DETAILED DESCRIPTION

Figure 1:
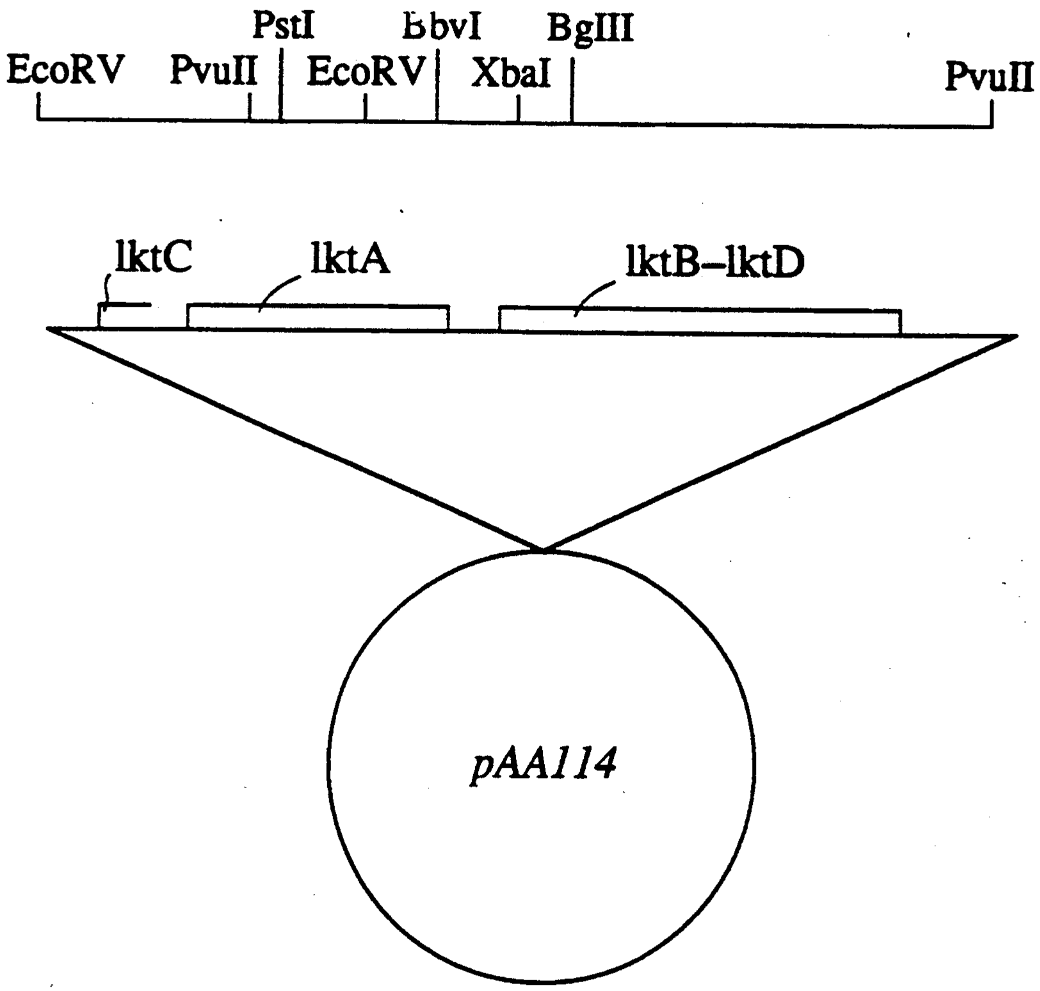
FIG. 1 depicts the structure of the leukotoxin gene of *P. haemolytica* cloned in *E. coli* (Plasmid pAA114).

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); B. Perbal, *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All patents, patent applications, and publications mentioned herein, whether supra or infra, are hereby incorporated by reference in their entirety.

A. Definitions

In describing the present invention, the following terms will be employed, and are intended to be defined as indicated below.

An "antigen" refers to a molecule containing one or more epitopes that will stimulate a host's immune system to make a humoral and/or cellular antigen-specific response. The term is also used interchangeably with "immunogen." An antigen will include one or more epitopes from a protein molecule, such as but not limited to, bacterial and viral proteins, as well as peptide hormones which elicit an immune response. Additionally, an antigen can comprise one or more identical or different immunogenic repeating sequences of a protein. Specifically excluded from the definition for purposes of this application are cytokines such as interleukin-1 (IL1), interleukin-2 (IL2), interleukin-3 (IL3), interleukin-4 (IL4), and gamma-interferon (γIFN).

The term "leukotoxin polypeptide" intends a polypeptide derived from a protein belonging to the family of molecules characterized by the carboxy-terminus consensus amino acid sequence Gly-Gly-X-Gly-X-Asp (SEQ ID NO:11) (Highlander et al., *DNA* (1989) 8:15–28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee, C. A., and Lo, R. Y. C. Infect. *Immun.* (1987) 55:3233–3236; Lo, R. Y. C., *Can. J. Vet. Res.* (1990) 54:S33–S35; Welch, R. A., *Mol. Microbiol.* (1991) 5:521–528). This family of toxins is known as the "RTX" family of toxins (Lo, R. Y. C., *Can. J. Vet. Res.* (1990) 54:S33–S35). In addition, the term "leukotoxin polypeptide" refers to a leukotoxin polypeptide which is chemically synthesized, isolated from an organism expressing the same, or recombinantly produced. Furthermore, the term intends an immunogenic protein having an amino acid sequence substantially homologous to a contiguous amino acid sequence found in the particular native leukotoxin molecule. Thus, the term includes both full-length and partial sequences, as well as analogs. Although native full-length leukotoxins display leukotoxic activity, the term "leukotoxin" also intends molecules which remain immunogenic yet lack the cytotoxic character of native leukotoxins. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee, C. A., and Lo, R. Y. C., *Infect. Immun.* (1987) 55:3233-3236; Highlander et al., *DNA* (1989) 8:15-28; Welch, R. A., *Mol. Microbiol.* (1991) 5:521-528.

Figure 2:
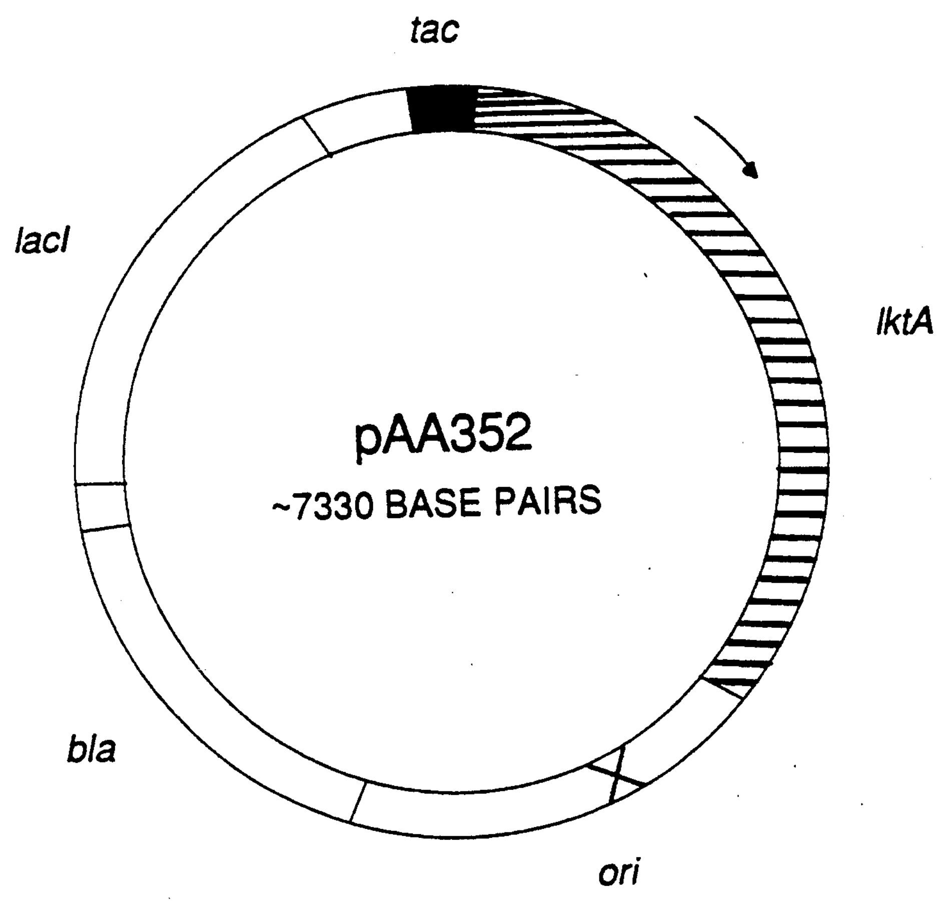
FIG. 2 depicts the structure of Plasmid pAA352 wherein tac is the hybrid trp::lac promoter from *E. coli*; bla represents the β-lactamase gene (ampicillin resistance); ori is the ColEl-based plasmid origin of replication; lktA is the *P. haemolytica* leukotoxin structural gene; and lacl is the *E. coli* lac operon repressor. The direction of transcription/translation of the leukotoxin gene is indicated by the arrow. The size of each component is not drawn to scale.
Figure 5:
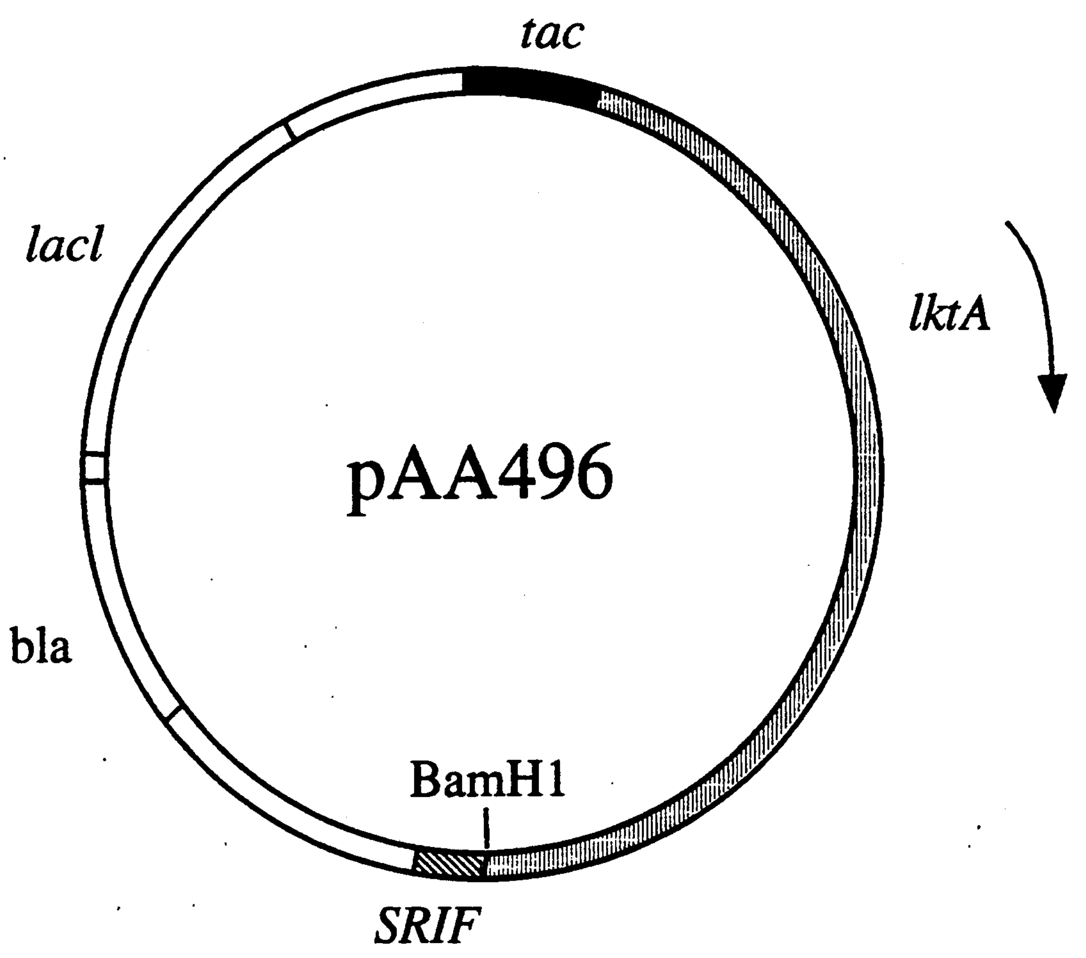
Figure 7:
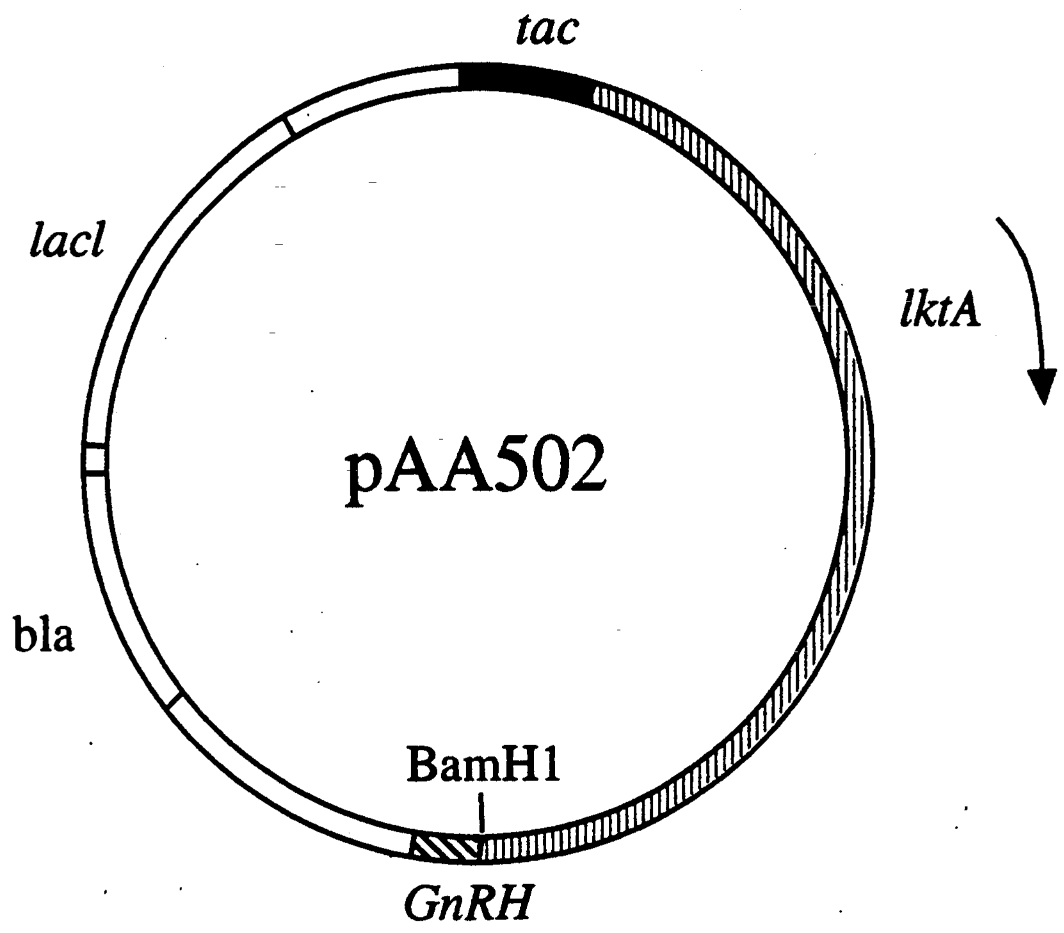
Figure 9:
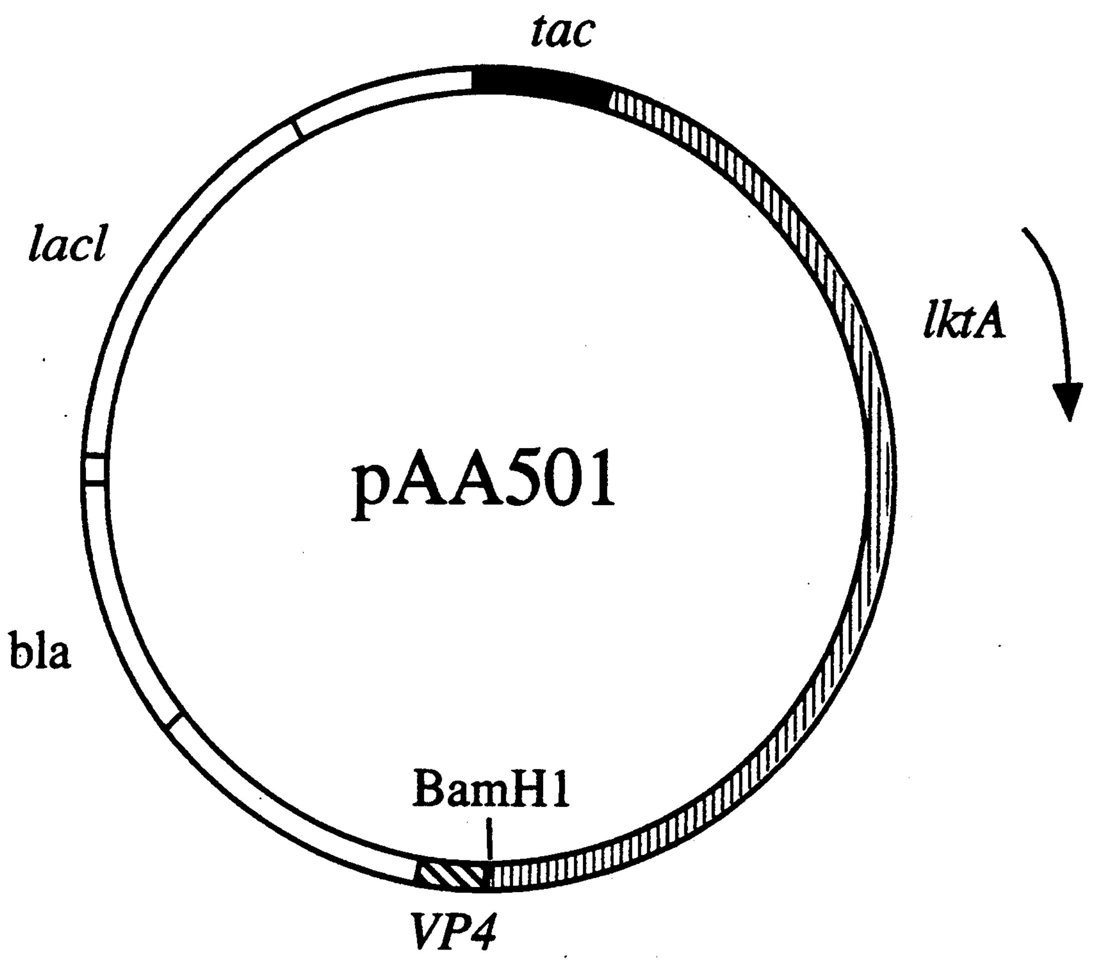

By "LKT 352" is meant a protein which is derived from the lktA gene present in plasmid pAA352 (FIG. 2, ATCC Accession No. 68283). The nucleotide sequence and corresponding amino acid sequence of this gene are described in International Publication No. WO91/15237 and shown in FIGS. 3-1 to 3-10 (SEQ ID NO:1). The gene encodes a truncated leukotoxin, having 931 amino acids, which lacks the cytotoxic portion of the molecule. The derived LKT 352 is not necessarily physically derived from the sequence present in plasmid pAA352. Rather, it may be generated in any manner, including for example, by chemical synthesis or recombinant production. In addition, the amino acid sequence of the protein need only be substantially homologous to the depicted sequence. Thus, sequence variations may be present so long as the protein functions to enhance the immunogenicity of the antigen with which it is associated.

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

An "immunological response" to an antigen or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or $\gamma\delta$ T cells, directed specifically to an antigen or antigens included in the composition or vaccine of interest.

An "immunogenic protein" or "immunogenic amino acid sequence" is a protein or amino acid sequence, respectively, which elicits an immunological response in a subject to which it is administered.

A leukotoxin-antigen chimera displays "increased immunogenicity" when it possesses a greater capacity to elicit an immune response than the corresponding antigen alone. Such increased immunogenicity can be determined by administering the particular leukotoxin-antigen and antigen controls to animals and comparing antibody titers against the two using standard assays such as radioimmunoassays and ELISAs, well known in the art.

By "carrier system" is meant a system-which includes a molecule that serves to increase the immunogenicity of an antigen administered therewith, as defined above. Without being bound by any particular theory, the molecule may function to increase the immunogenicity of the antigen by presenting the same to cells of the immune system, such as antigen presenting cells, macrophages, follicular dendritic cells, B cells and T cells; or by stimulating the immune system to respond at a level greater than that observed when the antigen is administered alone.

By "subunit antigen composition" is meant a composition containing at least one immunogenic polypeptide, but not all antigens, derived from or homologous to an antigen from a pathogen of interest. Such a composition is substantially free of intact pathogen cells or particles. Generally, a "subunit antigen composition" is prepared from at least partially purified (preferably substantially purified) immunogenic polypeptides from the pathogen, or recombinant analogs thereof.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from a source occurring in nature. Thus, the term "native leukotoxin" would include naturally occurring leukotoxin and fragments thereof.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "rotavirus VP6 protein" refers to the art-recognized major viral protein of the inner capsid from any species or strain within the family Reoviridae. See, e.g., Kapikian et al., 1985. Examples of rotavirus strains from which the VP6 protein can be isolated and employed in the present invention include, but are not limited to, Simian SA-11, human D rotavirus, bovine UK rotavirus, human Wa or W rotavirus, human DS-1 rotavirus, rhesus rotavirus, the "O" agent, bovine NCDV rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, bovine C486 rotavirus, and strains derived from them. Thus the present invention encompasses the use of VP6 from any rotavirus strain, whether from subgroup I, subgroup II, or any as yet unidentified subgroup, as well as from any of the serotypes 1-7, as well as any as yet unidentified serotypes. Such VP6 proteins can be used as immunologic carriers of polypeptides. These carrier molecules comprise amino acid sequences of rotavirus VP6 amino acid sequences which are unique to the class, or any member of the class, of VP6 polypeptides. Such unique sequences of VP6 proteins are referred to as a "rotavirus VP6 inner capsid protein amino acid sequence." VP6 carriers are further disclosed in U.S. Pat. No. 5,071,651, incorporated herein by reference in its entirety.

A carrier that is "substantially homologous to a rotavirus VP6 inner capsid protein or a functional fragment thereof" is one in which at least about 85%, preferably at least about 90%, and most preferably at least about 95%, of the amino acids match over a defined length of the molecule. A "functional fragment" of a rotavirus VP6 inner capsid protein is a fragment with the capability of acting as a carrier molecule for the novel chimeric proteins of the instant invention.

A "replicon" is any genetic element (e.g., plasmid, chromosome, virus) that functions as an autonomous unit of DNA replication in vivo or in vitro; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5′ to 3′ direction along the nontranscribed strand of DNA (i.e., the strand having the sequence homologous to the mRNA).

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5′ (amino) terminus and a translation stop codon at the 3′ (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3′ to the coding sequence.

A "promoter sequence" is a DNA regulatory region capable of binding RNA polymerase in a cell and initiating transcription of a downstream (3′ direction) coding sequence. For purposes of defining the present invention, the promoter sequence is bound at the 3′ terminus by the translation start codon (ATG) of a coding sequence and extends upstream (5′ direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" another coding sequence when RNA polymerase will transcribe the two coding sequences into mRNA, which is then translated into a chimeric polypeptide encoded by the two coding sequences. The coding sequences need not be contiguous to one another so long as the transcribed sequence is ultimately processed to produce the desired chimeric protein.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The term "functionally equivalent" intends that the amino acid sequence of the subject fusion protein is one that will elicit an immunological response, as defined above, equivalent to an unmodified immunogenic leukotoxin-antigen chimeric protein.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms or the disease of interest (therapy).

B. General Methods

Central to the instant invention is the discovery that leukotoxin polypeptides, when coupled to selected antigens, are able to increase the immunogenicity of the antigen as compared to the immunogenicity of the antigen when presented alone. Thus, leukotoxin polypeptides can act as carrier proteins for the presentation of a desired antigen to the immune system. Accordingly, the chimeric proteins can be formulated into vaccine compositions which provide enhanced immunogenicity to the antigen presented therewith. The fusion of the leukotoxin gene to the selected antigen further functions to facilitate purification of the chimeric protein from cells expressing the same.

The leukotoxin carrier is especially useful for the presentation of small or endogenous peptide antigens, including peptide hormones, and bacterial and viral antigens, which typically elicit poor immune responses when presented without the aid of a carrier. Exemplified herein are leukotoxin chimeras which include leukotoxin fused to small peptide hormones—somatostatin (SRIF) and gonadatropin releasing hormone (GnRH). SRIF-14 has 14 amino acids and GnRH possesses 10 amino acids. The nucleotide sequences of SRIF and GnRH are depicted in FIG. 4 (SEQ ID NOS:2-7). Because the sequences are relatively short, they can easily be generated using synthetic techniques, as described further below. Because these hormones are small in size and are endogenous to several mammals such as humans, bovines etc., these substances require the use of carrier proteins in order to elicit an adequate immune response in such mammals. Immunization with these hormones can regulate growth rate, lactation and reproductive efficiency. A detailed discussion of SRIF can be found in U.S. Pat. No. 5,212,156, filed 18 Jun. 1990, which is incorporated herein by reference in its entirety. GnRH is further discussed in U.S. Pat. No. 4,975,420, incorporated herein by reference in its entirety.

Also exemplified herein is a chimera comprised of leukotoxin and bovine rotavirus viral protein 4 (VP4). VP4 (molecular weight 86,719), functions as the viral hamagglutinin and forms the spike-like projections protruding from the surface of the virus. Antibodies capable of neutralizing the virus bind to the tip of the spike. VP4 appears to play a major role in viral attachment during infection. The nucleotide sequence of VP4 is depicted in FIG. 4. For a further discussion of rotavirus infection and VP4, see, Redmond, M. J. et al. in *Viral Diseases* (Ed. E. Kurstak, Marcel Dekker, New York, 1991, pp. 387-404); and International Publication No. WO/9207941, published 14 May 1992, both incorporated herein by reference in their entirety. Although the invention is described with respect to these particular proteins, leukotoxin polypeptides, or proteins functionally equivalent and substantially homologous thereto, can be easily fused to other antigens, based on the disclosure herein, in order to increase the immunogenicity thereof.

The leukotoxin-antigen complex can be conveniently produced recombinantly as a chimeric protein. The antigen portion of the chimera can be fused either 5' or 3' to the leukotoxin portion of the molecule.

Actively growing cells of *P. haemolytica* have been shown to secrete leukotoxin which can be cloned, the gene encoding the same isolated, and fused with a gene encoding a desired antigen, using techniques well known in the art. The resulting chimeric proteins can be expressed and used to immunize subjects against the particular antigen fused to leukotoxin.

The nucleotide sequence coding for full-length *P. haemolytica* A1 leukotoxin has been determined. See, e.g., Lo, R. Y. C. *Infect. Immun.* (1987) 55:1987-1996; U.S. Pat. No. 5,055,400, incorporated herein by reference in its entirety. *P. haemolytica* leukotoxin can be produced using recombinant techniques and purified from, for example, bacterial cells. The leukotoxin can also be purified from native bacteria using immunoadsorbent chromatography.

Similarly, the coding sequences for numerous antigens are known or can be determined. Again, these antigens can be purified using standard techniques.

Purification of the above proteins, using standard techniques including those described herein, permits the sequencing of the same by any of the various methods known to those skilled in the art. For example, the amino acid sequences can be determined by repetitive cycles of Edman degradation, followed by amino acid analysis by HPLC. Other methods of amino acid sequencing are also known in the art. Furthermore, fragments of the proteins can be tested for biological activity and active epitopes used in compositions in lieu of the entire protein.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; T. Maniatis et al., supra.

First, a DNA library is prepared. The library can consist of genomic DNA from *P. haemolytica* (for the isolation of the leukotoxin gene) or from appropriate cells or viruses (for the isolation of the desired antigen gene). Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin, using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature* (1981) 292:756; Nambair et al. *Science* (1984) 223:1299; Jay et al. *J. Biol. Chem.* (1984) 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; T. Maniatis et al., supra; B. Perbal, supra.

Suitable restriction enzymes can then be employed to isolate the appropriate antigen gene or leukotoxin gene and these sequences can be ligated together and cloned to form a leukotoxin-antigen fusion gene.

The fusion gene can be placed under the control of a promoter, ribosome binding site (for bacterial expression) and, optionally, an operator (collectively referred to herein as "control" elements), so that the DNA sequence encoding the chimeric protein is transcribed into RNA in the host cell transformed by a vector containing this expression construction. The coding sequence may or may not contain a signal peptide or leader sequence. The chimeric proteins of the present invention can be expressed using, for example, native *P. haemolytica* promoter, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular fusion coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular chimeric protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the chimeric proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The chimeric protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired antigen.

The chimeric proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the chimeric protein, or an active fragment thereof, or an analog thereof. The chimeric protein can consist of leukotoxin fused to an epitope of the desired antigen, as defined above. Thus, if the fragment or analog of the fusion protein is used, it will include the amino acid sequence of leukotoxin, or a fragment of the same which interacts with the immune system to increase the immunogenicity of the antigen or epitope thereof, linked to the antigen of interest.

Prior to immunization, it may be desirable to further increase the immunogenicity of the particular chimeric protein, or an analog of the protein, or particularly fragments of the protein. This can be accomplished in any one of several ways known to those of skill in the art. For example, the antigenic peptide may be administered linked to a carrier, in addition to the leukotoxin carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric proteins of the present invention include VP6 polypeptides of rotaviruses, or functional fragments thereof, as disclosed in U.S. Pat. No. 5,071,651, and incorporated herein by reference. Also useful is a fusion product of a viral protein and the subject leukotoxin-antigen immunogen made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the fusion proteins of the present invention may be coupled to erythrocytes, preferably the subject's own erythrocytes. Methods of coupling peptides to proteins or cells are known to those of skill in the art.

The novel chimeric proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel chimeric proteins can be constructed as follows. The DNA encoding the particular leukotoxin-antigen chimeric protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant chimeric protein into the viral genome. The resulting TK recombinant can be selected by culturing the cells in the presence of 5-bromodeoxyuridine and picking viral plaques resistant thereto.

It is also possible to immunize a subject with a protein of the present invention, or an immunogenic fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975. The composition or formulation to be administered will, in any event, contain a quantity of the protein adequate to achieve the desired immunized state in the subject being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the chimeric protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric proteins can also be presented using implanted mini-pumps, well known in the art.

Furthermore, the chimeric proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, the polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, approximately 1 μg to 1 mg, more generally 5 μg to 100 μg of antigen per ml of injected solution, should be adequate to raise an immunological response when administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required under 35 USC §112. The nucleic acid sequences of these plasmids, as well as the amino sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| *P. haemolytica* serotype 1 B122 | February 1, 1989 | 53863 |
| pAA352 in *E. coli* W1485 | March 30, 1990 | 68283 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, *E. coli*, DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt11, respectively. See DNA CLONING: Vols I and II, supra.

*P. haemolytica* biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

Isolation of *P. haemolytica* Leukotoxin Gene

To isolate the leukotoxin gene, gene libraries of *P. haemolytica* A1 (strain B122) were constructed using standard techniques. See, Lo et al., *Infect. Immun.*, supra; *DNA CLONING: Vols. I and II*, supra; and T. MANIATIS et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See, Lo et al., *Infect. Immun.*, supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence. The structure of this plasmid is shown in FIG. 1.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432: lacI digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BamHI-digested pAA342, yielding the plasmid pAA352. The structure of pAA352 is shown in FIG. 2 and the nucleotide sequence and predicted amino acid sequence of *P. haemolytica* leukotoxin shown in FIGS. 3-1 to 3-10 (SEQ ID NO:1).

EXAMPLE 2

Construction of LKT-antigen Fusions

Three representative LKT-antigen fusions were constructed as follows. Oligonucleotides containing sequences from the bovine rotavirus VP4, GnRH and SRIF genes were constructed on a Pharmacia Gene Assembler using standard phosphoramidite chemistry. The sequences of these oligonucleotides are shown in FIG. 4 (SEQ ID NOS:2-7). The oligonucleotides were annealed and ligated into the vector pAA352 (ATCC No. 68283, and described above), which had been digested with the restriction endonuclease BamH1. This vector contains the *P. haemolytica* leukotoxin gene. The ligated DNA was used to transform *E. coli* strain JM105 (in the case of SRIF) or MH3000 (for VP4 and GnRH). Transformants containing the oligonucleotide inserts were identified by restriction endonuclease mapping. Plasmid DNA from the *E. coli* MH3000 strains was then isolated and used to transform the strain JM105. The recombinant plasmids were designated pAA496 (LKT-SRIF, FIG. 5), pAA502 (LKT-GnRH, FIG. 7), and pAA501 (LKT-VP4, FIG. 9). The nucleotide sequences of these three fusions are shown in FIGS. 6-1 to 6-10 (SEQ ID NO:8), 8-1 to 8-10 (SEQ ID NO:9) and 10-1 to 10-10 (SEQ ID NO:10), respectively.

EXAMPLE 3

Purification of LKT-antigen Fusions

The recombinant LKT-antigen fusions from Example 2 were purified using the following procedure. For each fusion, five to ten colonies of the transformed *E. coli* strains were inoculated into 10 ml of TB broth supplemented with 100 micrograms/ml of ampicillin and incubated at 37° C. for 6 hours on a G10 shaker, 220 rpm. Four ml of this culture was diluted into each of two baffled Fernbach flasks containing 400 ml of TB broth+ampicillin and incubated overnight as described above. Cells were harvested by centrifugation for 10 minutes at 4,000 rpm in polypropylene bottles, 500 ml volume, using a Sorvall GS3 rotor. The pellet was resuspended in an equal volume of TB broth containing ampicillin which had been prewarmed to 37° C. (i.e., 2×400 ml), and the cells were incubated for 2 hours as described above.

3.2 ml of isopropyl-B,D-thiogalactopyranoside (IPTG, Gibco/BRL), 500 mM in water (final concentration=4 mM), was added to each culture in order to induce synthesis of the recombinant fusion proteins. Cultures were incubated for two hours. Cells were harvested by centrifugation as described above, resuspended in 30 ml of 50 mM Tris-hydrochloride, 25% (w/v) sucrose, pH 8.0, and frozen at −70° C. The frozen cells were thawed at room temperature after 60 minutes at −70° C., and 5 ml of lysozyme (Sigma, 20 mg/ml in 250 mM Tris-HCl, pH 8.0) was added. The mixture was vortexed at high speed for 10 seconds and then placed on ice for 15 minutes. The cells were then added to 500 ml of lysis buffer in a 1000 ml beaker and mixed by stirring with a 2 ml pipette. The beaker containing the lysed cell suspension was-placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes at 10,000 rpm in a Sorvall SS34 rotor. The pellets were resuspended in a total of 100 ml of sterile double distilled water by vortexing at high speed, and the centrifugation step repeated. Supernatants were discarded and the pellets combined in 20 ml of 10 mM Tris-HCl, 150 mM NaCl, pH 8.0 (Tris-buffered saline) and the suspension frozen overnight at −20° C.

The recombinant suspension was thawed at room temperature and added to 100 ml of 8M Guanidine HCl (Sigma) in Tris-buffered saline and mixed vigorously. A magnetic stir bar was placed in the bottle and the solubilized sample was mixed at room temperature for 30 minutes. The solution was transferred to a 2000 ml Ehrlenmyer flask and 1200 ml of Tris-buffered saline was quickly added. This mixture was stirred at room temperature for an additional 2 hours. 500 ml aliquots were placed in dialysis bags (Spectrum, 63.7 mm diameter, 6,000–8,000 MW cutoff, #132670, from Fisher scientific) and these were placed in 4,000 ml beakers containing 3,500 ml of Tris-buffered saline+0.5M Guanidine HCl. The beakers were placed in a 4° C. room on a magnetic stirrer overnight after which dialysis buffer was replaced with Tris-buffered saline+0.1M Guanidine HCl and dialysis continued for 12 hours. The buffer was then replaced with Tris-buffered saline+0.05M Guanidine HCl and dialysis continued overnight. The buffer was replaced with Tris-buffered saline (no guanidine), and dialysis continued for 12 hours. This was repeated three more times. The final solution was poured into a 2000 ml plastic roller bottle (Corning) and 13 ml of 100 mM PMSF (in ethanol) was added to inhibit protease activity. The solution was stored at −20° C. in 100 ml aliquots.

To confirm that the fusion proteins had been isolated, aliquots of each preparation were diluted 20-fold in double distilled water, mixed with an equal volume of SDS-PAGE sample buffer, placed in a boiling water bath for five minutes and run through 12% polyacrylamide gels. Recombinant leukotoxin controls were also run. Western blots of the purification products were performed by reacting the LKT-SRIF preparation with swine anti-SRIF serum at a 1:500 dilution and the LKT-GnRH and LKT-VP4 preparations with mouse anti-VP4 serum at a 1:50 dilution. The only band visible in the LKT-SRIF western blot was that associated with the LKT-SRIF protein sample. No cross-reactivity with the leukotoxin was observed. Both the LKT-GnRH and LKT-VP4 proteins had similar apparent molecular weights, however, the anti-VP4 serum reacted only with the LKT-VP4 fusion protein.

All fusion proteins were expressed at high levels as inclusion bodies. The predicted molecular weights based on the DNA sequences of the three proteins (depicted in FIGS. 6-1 to 6-10 (SEQ ID NO:8), 8-1 to 8-10 (SEQ ID NO:9) and 10-1 to 10-10 (SEQ ID NO:10)) were 101,366 (LKT-SRIF); 100,521 (LKT-GnRH); and 102,120 (LKT-VP4). The molecular weight of the recombinant leukotoxin molecule was 99,338. Both the SRIF and VP4 fusions were shown to react with monospecific antisera against the corresponding peptide.

EXAMPLE 4

In Vivo Immunologic Activity of LKT-antigen Fusions

To test for enhanced immunogenicity of the LKT-antigen fusions as compared to the antigens alone, LKT-SRIF fusion protein was purified from *E. coli* cultures induced with IPTG, as described in Example 2. Aggregated protein was dissolved by treating with guanidine-HCl at a final concentration of three molar. The leukotoxin concentration of this material was assayed using a standard quantitative leukotoxin specific ELISA. The assay utilized recombinant leukotoxin in 4M guanidine-HCl (2 mg/ml) as a standard. Rabbit anti-leukotoxin antiserum was used as a detection and quantitation system.

A vaccine was formulated to a volume of 1 ml by mixing equal volumes of LKT-SRIF, diluted in Hanks Buffered Saline, and Emulsigen Plus (MVP Laboratories, Ralston, Nebr.). Four three month old lambs were immunized twice with 100 micrograms of fusion protein (containing an equivalent of approximately 1.4 micrograms of SRIF peptide). Blood samples were taken 10 days after the second injection and were analyzed for leukotoxin and SRIF specific antisera. All of the animals were found to have anti-leukotoxin titers of greater than 1 in 50,000, as determined by a leukotoxin specific ELISA. SRIF titers were assayed by a radioimmunoassay as described in Laarveld, B., et al., *Can. J. Anim. Sci.* (1986) 66:77–83. Two animals were found to have titers greater than 1 in 100.

To further test the ability of the LKT-SRIF chimeras to induce an anti-SRIF immunological response in vivo, and to compare this response to that produced by other SRIF conjugates, the following vaccination trial was performed. Three groups of 8 female pigs, approximately 8 weeks of age (35–50 kg) were used which were Specific Pathogen Free. The animals were maintained in a minimal disease facility and were vaccinated on days 0, 21 and 35 of the trial with the following formulations:

Group 1—placebo which was saline formulated in Emulsigen Plus adjuvant containing 15 mg DDA (Kodak) (2 ml);

Group 2—LKT-SRIF (250 μg LKT, prepared as described above) formulated in the same adjuvant (2 ml);

Group 3—SRIF-avidin, biotinylated SRIF (10 μg) and 2.5 μg avidin, formulated in the same adjuvant (2 ml).

Blood samples were taken on days 0, 21 and 35, allowed to clot, centrifuged at 1500 g, and the serum removed. The serum antibody titers against SRIF were measured using the RIA procedure of Laarveld et al., *Can. J. Anim. Sci.* (1986) 66:77–83.

7 of the 8 animals immunized with the LKT-SRIF formulation produced significant titers against SRIF (>1:700) whereas only 2 of 8 animals immunized with the SRIF-Avidin responded with serum titers of >700.

This example demonstrates that leukotoxin chimeric molecules are highly immunogenic. It has been reported by Laarveld, et al., *Can. J. Animal Sci.* (1986) 66:77, that repeated immunization with greater than 100 micrograms of SRIF peptide conjugated to an ovalbumin carrier was necessary to evoke an immune reaction.

EXAMPLE 5

In Vivo Immunologic Activity of LKT-GnRH Fusions

To test for the ability of LKT-GnRH to induce an anti GnRH immunological response in vivo, and to compare this response to other GnRH carrier conjugates, the following vaccination trial was performed. Three groups of 8 male pigs, approximately 8 weeks of age (35-50 kg) were used which were Specific Pathogen Free. The animals were maintained in a minimal disease facility and were vaccinated on days 0 and 21 of the trial with the following formulations:

Group 1—placebo which consisted of saline formulated in Emulsigen Plus adjuvant containing 15 mg of DDA (2 ml);

Group 2—LKT-GnRH (250 μg LKT, prepared as described in the previous examples) formulated in the same adjuvant (2 ml);

Group 3—VP6-GnRH, 0.5 μg VP6 and 5 μg GnRH, formulated in the same adjuvant (2 ml). The VP6 preparation was made as described in U.S. Pat. No. 5,071,651, using the binding peptide described therein.

Blood samples were taken on days 0, 21 and 35, allowed to clot, centrifuged at 1500 g, and the serum removed. The serum antibody titers against GnRH were measured using the RIA procedure of Silversides et al., *J. Reprod. Immunol.* (1985) 7:171-184.

The results of this trial indicated that only those animals immunized with the LKT-GnRH formulation produced significant titers against GnRH (titers >1:70). Neither the placebo nor the VP6-GnRH groups produced anti-GnRH titers. Previously, multiple vaccinations with doses of GnRH of more than 100 μg, conjugated to other carrier proteins, were required to induce anti-hormone titers.

Thus, chimeric proteins including leukotoxin fused to a selected antigen, have been disclosed. Although preferred embodiments of the subject invention have been described in some detail, it is understood that obvious variations can be made without departing from the spirit and the scope of the invention as defined by the appended claims.

---

We claim:

1. An immunological carrier system comprising a chimeric protein, said chimeric protein consisting of a leukotoxin molecule which lacks leukotoxic activity, fused to somatostatin (SRIF), whereby said leukotoxin of said chimeric protein acts to increase the immunogenicity of said SRIF.

2. The carrier system of claim 1 wherein said chimetic protein consists of the amino acid sequence depicted in FIG. 6 (SEQ ID NO:8).

3. A vaccine composition comprising the chimetic protein of claim 1 and a pharmaceutically acceptable vehicle.

4. A method for presenting a selected antigen to a subject comprising administering to said subject an effective amount of a vaccine composition according to claim 3.

5. An immunological carrier system comprising a chimeric protein, said chimeric protein consisting of a leukotoxin molecule which lacks leukotoxic activity, fused to gonadotropin releasing hormone (GnRH), whereby said leukotoxin of said chimeric protein acts to increase the immunogenicity of said GnRH.

6. The carrier system of claim 5 wherein said chimeric protein consists of the amino acid sequence depicted in FIG. 8 (SEQ ID NO:9).

7. A vaccine composition comprising the chimeric protein of claim 5 and a pharmaceutically acceptable vehicle.

8. A method for presenting a selected antigen to a subject comprising administering to said subject an effective amount of a vaccine composition according to claim 7.

9. An immunological carrier system comprising a chimetic protein, said chimetic protein consisting of a leukotoxin molecule which lacks leukotoxic activity, fused to bovine rotavirus VP4, whereby said leukotoxin of said chimeric protein acts to increase the immunogenicity of said VP4.

10. The carrier system of claim 9 wherein said chimetic protein consists of the amino acid sequence depicted in FIG. 10 (SEQ ID NO:10).

11. A vaccine composition comprising the chimetic protein of claim 9 and a pharmaceutically acceptable vehicle.

12. A method for presenting a selected antigen to a subject comprising administering to said subject an effective amount of a vaccine composition according to claim 11.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2794 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..2778

( x i ) SEQUENCE DESCRIPTION: SEQ ID NO:1:

```
ATGGCTACTG TTATAGATCT AAGCTTCCCA AAAACTGGGG CAAAAAAAAT TATCCTCTAT    60
ATTCCCCAAA ATTACCAATA TGATACTGAA CAAGGTAATG GTTTACAGGA TTTAGTCAAA   120
GCGGCCGAAG AGTTGGGGAT TGAGGTACAA AGAGAAGAAC GCAATAATAT TGCAACAGCT   180
CAAACCAGTT TAGGCACGAT TCAAACCGCT ATTGGCTTAA CTGAGCGTGG CATTGTGTTA   240
TCCGCTCCAC AAATTGATAA ATTGCTACAG AAAACTAAAG CAGGCCAAGC ATTAGGTTCT   300
GCCGAAAGCA TTGTACAAAA TGCAAATAAA GCCAAAACTG TATTATCTGG CATTCAATCT   360
ATTTTAGGCT CAGTATTGGC TGGAATGGAT TTAGATGAGG CCTTACAGAA TAACAGCAAC   420
CAACATGCTC TTGCTAAAGC TGGCTTGGAG CTAACAAATT CATTAATTGA AAATATTGCT   480
AATTCAGTAA AAACACTTGA CGAATTTGGT GAGCAAATTA GTCAATTTGG TTCAAAACTA   540
CAAAATATCA AAGGCTTAGG GACTTTAGGA GACAAACTCA AAAATATCGG TGGACTTGAT   600
AAAGCTGGCC TTGGTTTAGA TGTTATCTCA GGGCTATTAT CGGGCGCAAC AGCTGCACTT   660
GTACTTGCAG ATAAAAATGC TTCAACAGCT AAAAAAGTGG GTGCGGGTTT TGAATTGGCA   720
```

-continued

```
AACCAAGTTG TTGGTAATAT TACCAAAGCC GTTTCTTCTT ACATTTTAGC CCAACGTGTT    780
GCAGCAGGTT TATCTTCAAC TGGGCCTGTG GCTGCTTTAA TTGCTTCTAC TGTTTCTCTT    840
GCGATTAGCC CATTAGCATT TGCCGGTATT GCCGATAAAT TTAATCATGC AAAAAGTTTA    900
GAGAGTTATG CCGAACGCTT TAAAAAATTA GGCTATGACG GAGATAATTT ATTAGCAGAA    960
TATCAGCGGG GAACAGGGAC TATTGATGCA TCGGTTACTG CAATTAATAC CGCATTGGCC   1020
GCTATTGCTG GTGGTGTGTC TGCTGCTGCA GCCGGCTCGG TTATTGCTTC ACCGATTGCC   1080
TTATTAGTAT CTGGGATTAC CGGTGTAATT TCTACGATTC TGCAATATTC TAAACAAGCA   1140
ATGTTTGAGC ACGTTGCAAA TAAAATTCAT AACAAAATTG TAGAATGGGA AAAAAATAAT   1200
CACGGTAAGA ACTACTTTGA AAATGGTTAC GATGCCCGTT ATCTTGCGAA TTTACAAGAT   1260
AATATGAAAT TCTTACTGAA CTTAAACAAA GAGTTACAGG CAGAACGTGT CATCGCTATT   1320
ACTCAGCAGC AATGGGATAA CAACATTGGT GATTTAGCTG GTATTAGCCG TTTAGGTGAA   1380
AAAGTCCTTA GTGGTAAAGC CTATGTGGAT GCGTTTGAAG AAGGCAAACA CATTAAAGCC   1440
GATAAATTAG TACAGTTGGA TTCGGCAAAC GGTATTATTG ATGTGAGTAA TTCGGGTAAA   1500
GCGAAAACTC AGCATATCTT ATTCAGAACG CCATTATTGA CGCCGGGAAC AGAGCATCGT   1560
GAACGCGTAC AAACAGGTAA ATATGAATAT ATTACCAAGC TCAATATTAA CCGTGTAGAT   1620
AGCTGGAAAA TTACAGATGG TGCAGCAAGT TCTACCTTTG ATTTAACTAA CGTTGTTCAG   1680
CGTATTGGTA TTGAATTAGA CAATGCTGGA AATGTAACTA AAACCAAAGA AACAAAAATT   1740
ATTGCCAAAC TTGGTGAAGG TGATGACAAC GTATTTGTTG GTTCTGGTAC GACGGAAATT   1800
GATGGCGGTG AAGGTTACGA CCGAGTTCAC TATAGCCGTG GAAACTATGG TGCTTTAACT   1860
ATTGATGCAA CCAAAGAGAC CGAGCAAGGT AGTTATACCG TAAATCGTTT CGTAGAAACC   1920
GGTAAAGCAC TACACGAAGT GACTTCAACC CATACCGCAT TAGTGGGCAA CCGTGAAGAA   1980
AAAATAGAAT ATCGTCATAG CAATAACCAG CACCATGCCG GTTATTACAC CAAAGATACC   2040
TTGAAAGCTG TTGAAGAAAT TATCGGTACA TCACATAACG ATATCTTTAA AGGTAGTAAG   2100
TTCAATGATG CCTTTAACGG TGGTGATGGT GTCGATACTA TTGACGGTAA CGACGGCAAT   2160
GACCGCTTAT TTGGTGGTAA AGGCGATGAT ATTCTCGATG GTGGAAATGG TGATGATTTT   2220
ATCGATGGCG GTAAAGGCAA CGACCTATTA CACGGTGGCA AGGGCGATGA TATTTTCGTT   2280
CACCGTAAAG GCGATGGTAA TGATATTATT ACCGATTCTG ACGGCAATGA TAAATTATCA   2340
TTCTCTGATT CGAACTTAAA AGATTTAACA TTTGAAAAAG TTAAACATAA TCTTGTCATC   2400
ACGAATAGCA AAAAAGAGAA AGTGACCATT CAAAACTGGT TCCGAGAGGC TGATTTTGCT   2460
AAAGAAGTGC CTAATTATAA AGCAACTAAA GATGAGAAAA TCGAAGAAAT CATCGGTCAA   2520
AATGGCGAGC GGATCACCTC AAAGCAAGTT GATGATCTTA TCGCAAAAGG TAACGGCAAA   2580
ATTACCCAAG ATGAGCTATC AAAAGTTGTT GATAACTATG AATTGCTCAA ACATAGCAAA   2640
AATGTGACAA ACAGCTTAGA TAAGTTAATC TCATCTGTAA GTGCATTTAC CTCGTCTAAT   2700
GATTCGAGAA ATGTATTAGT GGCTCCAACT TCAATGTTGG ATCAAAGTTT ATCTTCTCTT   2760
CAATTTGCTA GGGGATCCTA GCTAGCTAGC CATG                                2794
```

( 2 ) INFORMATION FOR SEQ ID NO:2:

( i ) SEQUENCE CHARACTERISTICS:
- ( A ) LENGTH: 60 base pairs
- ( B ) TYPE: nucleic acid
- ( C ) STRANDEDNESS: single
- ( D ) TOPOLOGY: linear ( i i ) MOLECULE TYPE: DNA (genomic)

-continued ( x i ) SEQUENCE DESCRIPTION: SEQ ID NO:2:

GATCCAGCTC TTCTGCCGGC TGCAAAAACT TCTTCTGGAA AACCTTCACC AGCTGCTAGG 60

( 2 ) INFORMATION FOR SEQ ID NO:3:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GATCCCTAGC AGCTGGTGAA GGTTTTCCAG AAGAAGTTTT TGCAGCCGGC AGAAGAGCTG 60

( 2 ) INFORMATION FOR SEQ ID NO:4:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GATCTCAGCA TTGGAGCTAC GGCCTGCGCC CTGGCTAAG 39

( 2 ) INFORMATION FOR SEQ ID NO:5:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GATCCTTAGC CAGGGCGCAG GCCGTAGCTC CAATGCTGA 39

( 2 ) INFORMATION FOR SEQ ID NO:6:

( i ) SEQUENCE CHARACTERISTICS:
( A ) LENGTH: 83 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GATCTTGCAA CATTGTGCCT GTGAGCATTG TGAGCCGCAA CATTGTGTAC ACCCGCGCGC 60

AACCTAACCA AGACATTGTG TAG 83

( 2 ) INFORMATION FOR SEQ ID NO:7:

( i ) SEQUENCE CHARACTERISTICS:
( A ) LENGTH: 83 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

GATCCTACAC AATGTCTTGG TTAAGTTGCG CGCGGGTGTA CACAATGTTG CGGCTCACAA 60

TCGTCACAGG CACAATGTTG CAA 83

-continued ( 2 ) INFORMATION FOR SEQ ID NO:8:

( i ) SEQUENCE CHARACTERISTICS:
( A ) LENGTH: 2838 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..2829

( x i ) SEQUENCE DESCRIPTION: SEQ ID NO:8:

ATGGCTACTG TTATAGATCT AAGCTTCCCA AAAACTGGGG CAAAAAAAAT TATCCTCTAT 60
ATTCCCCAAA ATTACCAATA TGATACTGAA CAAGGTAATG GTTTACAGGA TTTAGTCAAA 120
GCGGCCGAAG AGTTGGGGAT TGAGGTACAA AGAGAAGAAC GCAATAATAT TGCAACAGCT 180
CAAACCAGTT TAGGCACGAT TCAAACCGCT ATTGGCTTAA CTGAGCGTGG CATTGTGTTA 240
TCCGCTCCAC AAATTGATAA ATTGCTACAG AAAACTAAAG CAGGCCAAGC ATTAGGTTCT 300
GCCGAAAGCA TTGTACAAAA TGCAAATAAA GCCAAAACTG TATTATCTGG CATTCAATCT 360
ATTTTAGGCT CAGTATTGGC TGGAATGGAT TTAGATGAGG CCTTACAGAA TAACAGCAAC 420
CAACATGCTC TTGCTAAAGC TGGCTTGGAG CTAACAAATT CATTAATTGA AAATATTGCT 480
AATTCAGTAA AAACACTTGA CGAATTTGGT GAGCAAATTA GTCAATTTGG TTCAAAACTA 540
CAAAATATCA AAGGCTTAGG GACTTTAGGA GACAAACTCA AAAATATCGG TGGACTTGAT 600
AAAGCTGGCC TTGGTTTAGA TGTTATCTCA GGGCTATTAT CGGGCGCAAC AGCTGCACTT 660
GTACTTGCAG ATAAAAATGC TTCAACAGCT AAAAAAGTGG GTGCGGGTTT TGAATTGGCA 720
AACCAAGTTG TTGGTAATAT TACCAAAGCC GTTTCTTCTT ACATTTTAGC CCAACGTGTT 780
GCAGCAGGTT TATCTTCAAC TGGGCCTGTG GCTGCTTTAA TTGCTTCTAC TGTTTCTCTT 840
GCGATTAGCC CATTAGCATT TGCCGGTATT GCCGATAAAT TTAATCATGC AAAAAGTTTA 900
GAGAGTTATG CCGAACGCTT TAAAAAATTA GGCTATGACG GAGATAATTT ATTAGCAGAA 960
TATCAGCGGG GAACAGGGAC TATTGATGCA TCGGTTACTG CAATTAATAC CGCATTGGCC 1020
GCTATTGCTG GTGGTGTGTC TGCTGCTGCA GCCGGCTCGG TTATTGCTTC ACCGATTGCC 1080
TTATTAGTAT CTGGGATTAC CGGTGTAATT TCTACGATTC TGCAATATTC TAAACAAGCA 1140
ATGTTTGAGC ACGTTGCAAA TAAAATTCAT AACAAAATTG TAGAATGGGA AAAAAATAAT 1200
CACGGTAAGA ACTACTTTGA AAATGGTTAC GATGCCCGTT ATCTTGCGAA TTTACAAGAT 1260
AATATGAAAT TCTTACTGAA CTTAAACAAA GAGTTACAGG CAGAACGTGT CATCGCTATT 1320
ACTCAGCAGC AATGGGATAA CAACATTGGT GATTTAGCTG GTATTAGCCG TTTAGGTGAA 1380
AAAGTCCTTA GTGGTAAAGC CTATGTGGAT GCGTTTGAAG AAGGCAAACA CATTAAAGCC 1440
GATAAATTAG TACAGTTGGA TTCGGCAAAC GGTATTATTG ATGTGAGTAA TTCGGGTAAA 1500
GCGAAAACTC AGCATATCTT ATTCAGAACG CCATTATTGA CGCCGGGAAC AGAGCATCGT 1560
GAACGCGTAC AAACAGGTAA ATATGAATAT ATTACCAAGC TCAATATTAA CCGTGTAGAT 1620
AGCTGGAAAA TTACAGATGG TGCAGCAAGT TCTACCTTTG ATTTAACTAA CGTTGTTCAG 1680
CGTATTGGTA TTGAATTAGA CAATGCTGGA AATGTAACTA AAACCAAAGA AACAAAAATT 1740
ATTGCCAAAC TTGGTGAAGG TGATGACAAC GTATTTGTTG GTTCTGGTAC GACGGAAATT 1800
GATGGCGGTG AAGGTTACGA CCGAGTTCAC TATAGCCGTG GAAACTATGG TGCTTTAACT 1860
ATTGATGCAA CCAAAGAGAC CGAGCAAGGT AGTTATACCG TAAATCGTTT CGTAGAAACC 1920

-continued

GGTAAAGCAC TACACGAAGT GACTTCAACC CATACCGCAT TAGTGGGCAA CCGTGAAGAA 1980

AAAATAGAAT ATCGTCATAG CAATAACCAG CACCATGCCG GTTATTACAC CAAAGATACC 2040

TTGAAAGCTG TTGAAGAAAT TATCGGTACA TCACATAACG ATATCTTTAA AGGTAGTAAG 2100

TTCAATGATG CCTTTAACGG TGGTGATGGT GTCGATACTA TTGACGGTAA CGACGGCAAT 2160

GACCGCTTAT TTGGTGGTAA AGGCGATGAT ATTCTCGATG GTGGAAATGG TGATGATTTT 2220

ATCGATGGCG GTAAAGGCAA CGACCTATTA CACGGTGGCA AGGGCGATGA TATTTTCGTT 2280

CACCGTAAAG GCGATGGTAA TGATATTATT ACCGATTCTG ACGGCAATGA TAAATTATCA 2340

TTCTCTGATT CGAACTTAAA AGATTTAACA TTTGAAAAAG TTAAACATAA TCTTGTCATC 2400

ACGAATAGCA AAAAAGAGAA AGTGACCATT CAAAACTGGT TCCGAGAGGC TGATTTTGCT 2460

AAAGAAGTGC CTAATTATAA AGCAACTAAA GATGAGAAAA TCGAAGAAAT CATCGGTCAA 2520

AATGGCGAGC GGATCACCTC AAAGCAAGTT GATGATCTTA TCGCAAAAGG TAACGGCAAA 2580

ATTACCCAAG ATGAGCTATC AAAAGTTGTT GATAACTATG AATTGCTCAA ACATAGCAAA 2640

AATGTGACAA ACAGCTTAGA TAAGTTAATC TCATCTGTAA GTGCATTTAC CTCGTCTAAT 2700

GATTCGAGAA ATGTATTAGT GGCTCCAACT TCAATGTTGG ATCAAAGTTT ATCTTCTCTT 2760

CAATTTGCTA GGGGATCCAG CTCTTCTGCC GGCTGCAAAA ACTTCTTCTG GAAAACCTTC 2820

ACCAGCTGCT AGGGATCC 2838

( 2 ) INFORMATION FOR SEQ ID NO:9:

( i ) SEQUENCE CHARACTERISTICS:
( A ) LENGTH: 2817 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..2808

( x i ) SEQUENCE DESCRIPTION: SEQ ID NO:9:

ATGGCTACTG TTATAGATCT AAGCTTCCCA AAAACTGGGG CAAAAAAAAT TATCCTCTAT 60

ATTCCCCAAA ATTACCAATA TGATACTGAA CAAGGTAATG GTTTACAGGA TTTAGTCAAA 120

GCGGCCGAAG AGTTGGGGAT TGAGGTACAA AGAGAAGAAC GCAATAATAT TGCAACAGCT 180

CAAACCAGTT TAGGCACGAT TCAAACCGCT ATTGGCTTAA CTGAGCGTGG CATTGTGTTA 240

TCCGCTCCAC AAATTGATAA ATTGCTACAG AAAACTAAAG CAGGCCAAGC ATTAGGTTCT 300

GCCGAAAGCA TTGTACAAAA TGCAAATAAA GCCAAAACTG TATTATCTGG CATTCAATCT 360

ATTTTAGGCT CAGTATTGGC TGGAATGGAT TTAGATGAGG CCTTACAGAA TAACAGCAAC 420

CAACATGCTC TTGCTAAAGC TGGCTTGGAG CTAACAAATT CATTAATTGA AAATATTGCT 480

AATTCAGTAA AAACACTTGA CGAATTTGGT GAGCAAATTA GTCAATTTGG TTCAAAACTA 540

CAAAATATCA AAGGCTTAGG GACTTTAGGA GACAAACTCA AAAATATCGG TGGACTTGAT 600

AAAGCTGGCC TTGGTTTAGA TGTTATCTCA GGGCTATTAT CGGGCGCAAC AGCTGCACTT 660

GTACTTGCAG ATAAAAATGC TTCAACAGCT AAAAAAGTGG GTGCGGGTTT TGAATTGGCA 720

AACCAAGTTG TTGGTAATAT TACCAAAGCC GTTTCTTCTT ACATTTTAGC CCAACGTGTT 780

GCAGCAGGTT TATCTTCAAC TGGGCCTGTG GCTGCTTTAA TTGCTTCTAC TGTTTCTCTT 840

GCGATTAGCC CATTAGCATT TGCCGGTATT GCCGATAAAT TTAATCATGC AAAAAGTTTA 900

GAGAGTTATG CCGAACGCTT TAAAAAATTA GGCTATGACG GAGATAATTT ATTAGCAGAA 960

TATCAGCGGG GAACAGGGAC TATTGATGCA TCGGTTACTG CAATTAATAC CGCATTGGCC 1020

-continued

GCTATTGCTG GTGGTGTGTC TGCTGCTGCA GCCGGCTCGG TTATTGCTTC ACCGATTGCC 1080

TTATTAGTAT CTGGGATTAC CGGTGTAATT TCTACGATTC TGCAATATTC TAAACAAGCA 1140

ATGTTTGAGC ACGTTGCAAA TAAAATTCAT AACAAAATTG TAGAATGGGA AAAAAATAAT 1200

CACGGTAAGA ACTACTTTGA AAATGGTTAC GATGCCCGTT ATCTTGCGAA TTTACAAGAT 1260

AATATGAAAT TCTTACTGAA CTTAAACAAA GAGTTACAGG CAGAACGTGT CATCGCTATT 1320

ACTCAGCAGC AATGGGATAA CAACATTGGT GATTTAGCTG GTATTAGCCG TTTAGGTGAA 1380

AAAGTCCTTA GTGGTAAAGC CTATGTGGAT GCGTTTGAAG AAGGCAAACA CATTAAAGCC 1440

GATAAATTAG TACAGTTGGA TTCGGCAAAC GGTATTATTG ATGTGAGTAA TTCGGGTAAA 1500

GCGAAAACTC AGCATATCTT ATTCAGAACG CCATTATTGA CGCCGGGAAC AGAGCATCGT 1560

GAACGCGTAC AAACAGGTAA ATATGAATAT ATTACCAAGC TCAATATTAA CCGTGTAGAT 1620

AGCTGGAAAA TTACAGATGG TGCAGCAAGT TCTACCTTTG ATTTAACTAA CGTTGTTCAG 1680

CGTATTGGTA TTGAATTAGA CAATGCTGGA AATGTAACTA AAACCAAAGA AACAAAAATT 1740

ATTGCCAAAC TTGGTGAAGG TGATGACAAC GTATTTGTTG GTTCTGGTAC GACGGAAATT 1800

GATGGCGGTG AAGGTTACGA CCGAGTTCAC TATAGCCGTG GAAACTATGG TGCTTTAACT 1860

ATTGATGCAA CCAAAGAGAC CGAGCAAGGT AGTTATACCG TAAATCGTTT CGTAGAAACC 1920

GGTAAAGCAC TACACGAAGT GACTTCAACC CATACCGCAT TAGTGGGCAA CCGTGAAGAA 1980

AAAATAGAAT ATCGTCATAG CAATAACCAG CACCATGCCG GTTATTACAC CAAAGATACC 2040

TTGAAAGCTG TTGAAGAAAT TATCGGTACA TCACATAACG ATATCTTTAA AGGTAGTAAG 2100

TTCAATGATG CCTTTAACGG TGGTGATGGT GTCGATACTA TTGACGGTAA CGACGGCAAT 2160

GACCGCTTAT TTGGTGGTAA AGGCGATGAT ATTCTCGATG GTGGAAATGG TGATGATTTT 2220

ATCGATGGCG GTAAAGGCAA CGACCTATTA CACGGTGGCA AGGGCGATGA TATTTTCGTT 2280

CACCGTAAAG GCGATGGTAA TGATATTATT ACCGATTCTG ACGGCAATGA TAAATTATCA 2340

TTCTCTGATT CGAACTTAAA AGATTTAACA TTTGAAAAAG TTAAACATAA TCTTGTCATC 2400

ACGAATAGCA AAAAAGAGAA AGTGACCATT CAAAACTGGT TCCGAGAGGC TGATTTTGCT 2460

AAAGAAGTGC CTAATTATAA AGCAACTAAA GATGAGAAAA TCGAAGAAAT CATCGGTCAA 2520

AATGGCGAGC GGATCACCTC AAAGCAAGTT GATGATCTTA TCGCAAAAGG TAACGGCAAA 2580

ATTACCCAAG ATGAGCTATC AAAAGTTGTT GATAACTATG AATTGCTCAA ACATAGCAAA 2640

AATGTGACAA ACAGCTTAGA TAAGTTAATC TCATCTGTAA GTGCATTTAC CTCGTCTAAT 2700

GATTCGAGAA ATGTATTAGT GGCTCCAACT TCAATGTTGG ATCAAAGTTT ATCTTCTCTT 2760

CAATTTGCTA GGGGATCTCA GCATTGGAGC TACGGCCTGC GCCCTGGCTA AGGATCC 2817

( 2 ) INFORMATION FOR SEQ ID NO:10:

( i ) SEQUENCE CHARACTERISTICS:
( A ) LENGTH: 2861 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..2853

( x i ) SEQUENCE DESCRIPTION: SEQ ID NO:10:

ATGGCTACTG TTATAGATCT AAGCTTCCCA AAAACTGGGG CAAAAAAAAT TATCCTCTAT 60

ATTCCCCAAA ATTACCAATA TGATACTGAA CAAGGTAATG GTTTACAGGA TTTAGTCAAA 120

-continued

```
GCGGCCGAAG AGTTGGGGAT TGAGGTACAA AGAGAAGAAC GCAATAATAT TGCAACAGCT   180
CAAACCAGTT TAGGCACGAT TCAAACCGCT ATTGGCTTAA CTGAGCGTGG CATTGTGTTA   240
TCCGCTCCAC AAATTGATAA ATTGCTACAG AAAACTAAAG CAGGCCAAGC ATTAGGTTCT   300
GCCGAAAGCA TTGTACAAAA TGCAAATAAA GCCAAAACTG TATTATCTGG CATTCAATCT   360
ATTTTAGGCT CAGTATTGGC TGGAATGGAT TTAGATGAGG CCTTACAGAA TAACAGCAAC   420
CAACATGCTC TTGCTAAAGC TGGCTTGGAG CTAACAAATT CATTAATTGA AAATATTGCT   480
AATTCAGTAA AAACACTTGA CGAATTTGGT GAGCAAATTA GTCAATTTGG TTCAAAACTA   540
CAAAATATCA AAGGCTTAGG GACTTTAGGA GACAAACTCA AAAATATCGG TGGACTTGAT   600
AAAGCTGGCC TTGGTTTAGA TGTTATCTCA GGGCTATTAT CGGGCGCAAC AGCTGCACTT   660
GTACTTGCAG ATAAAAATGC TTCAACAGCT AAAAAAGTGG GTGCGGGTTT TGAATTGGCA   720
AACCAAGTTG TTGGTAATAT TACCAAAGCC GTTTCTTCTT ACATTTTAGC CCAACGTGTT   780
GCAGCAGGTT TATCTTCAAC TGGGCCTGTG GCTGCTTTAA TTGCTTCTAC TGTTTCTCTT   840
GCGATTAGCC CATTAGCATT TGCCGGTATT GCCGATAAAT TTAATCATGC AAAAAGTTTA   900
GAGAGTTATG CCGAACGCTT TAAAAAATTA GGCTATGACG GAGATAATTT ATTAGCAGAA   960
TATCAGCGGG GAACAGGGAC TATTGATGCA TCGGTTACTG CAATTAATAC CGCATTGGCC  1020
GCTATTGCTG GTGGTGTGTC TGCTGCTGCA GCCGGCTCGG TTATTGCTTC ACCGATTGCC  1080
TTATTAGTAT CTGGGATTAC CGGTGTAATT TCTACGATTC TGCAATATTC TAAACAAGCA  1140
ATGTTTGAGC ACGTTGCAAA TAAAATTCAT AACAAAATTG TAGAATGGGA AAAAAATAAT  1200
CACGGTAAGA ACTACTTTGA AAATGGTTAC GATGCCCGTT ATCTTGCGAA TTTACAAGAT  1260
AATATGAAAT TCTTACTGAA CTTAAACAAA GAGTTACAGG CAGAACGTGT CATCGCTATT  1320
ACTCAGCAGC AATGGGATAA CAACATTGGT GATTTAGCTG GTATTAGCCG TTTAGGTGAA  1380
AAAGTCCTTA GTGGTAAAGC CTATGTGGAT GCGTTTGAAG AAGGCAAACA CATTAAAGCC  1440
GATAAATTAG TACAGTTGGA TTCGGCAAAC GGTATTATTG ATGTGAGTAA TTCGGGTAAA  1500
GCGAAAACTC AGCATATCTT ATTCAGAACG CCATTATTGA CGCCGGGAAC AGAGCATCGT  1560
GAACGCGTAC AAACAGGTAA ATATGAATAT ATTACCAAGC TCAATATTAA CCGTGTAGAT  1620
AGCTGGAAAA TTACAGATGG TGCAGCAAGT TCTACCTTTG ATTTAACTAA CGTTGTTCAG  1680
CGTATTGGTA TTGAATTAGA CAATGCTGGA AATGTAACTA AAACCAAAGA AACAAAAATT  1740
ATTGCCAAAC TTGGTGAAGG TGATGACAAC GTATTTGTTG GTTCTGGTAC GACGGAAATT  1800
GATGGCGGTG AAGGTTACGA CCGAGTTCAC TATAGCCGTG GAAACTATGG TGCTTTAACT  1860
ATTGATGCAA CCAAAGAGAC CGAGCAAGGT AGTTATACCG TAAATCGTTT CGTAGAAACC  1920
GGTAAAGCAC TACACGAAGT GACTTCAACC CATACCGCAT TAGTGGGCAA CCGTGAAGAA  1980
AAAATAGAAT ATCGTCATAG CAATAACCAG CACCATGCCG GTTATTACAC CAAAGATACC  2040
TTGAAAGCTG TTGAAGAAAT TATCGGTACA TCACATAACG ATATCTTTAA AGGTAGTAAG  2100
TTCAATGATG CCTTTAACGG TGGTGATGGT GTCGATACTA TTGACGGTAA CGACGGCAAT  2160
GACCGCTTAT TTGGTGGTAA AGGCGATGAT ATTCTCGATG GTGGAAATGG TGATGATTTT  2220
ATCGATGGCG GTAAAGGCAA CGACCTATTA CACGGTGGCA AGGGCGATGA TATTTTCGTT  2280
CACCGTAAAG GCGATGGTAA TGATATTATT ACCGATTCTG ACGGCAATGA TAAATTATCA  2340
TTCTCTGATT CGAACTTAAA AGATTTAACA TTTGAAAAAG TTAAACATAA TCTTGTCATC  2400
ACGAATAGCA AAAAAGAGAA AGTGACCATT CAAAACTGGT TCCGAGAGGC TGATTTTGCT  2460
AAAGAAGTGC CTAATTATAA AGCAACTAAA GATGAGAAAA TCGAAGAAAT CATCGGTCAA  2520
AATGGCGAGC GGATCACCTC AAAGCAAGTT GATGATCTTA TCGCAAAAGG TAACGGCAAA  2580
```

-continued

| | | | | | | |
|---|---|---|---|---|---|---|
| ATTACCCAAG | ATGAGCTATC | AAAAGTTGTT | GATAACTATG | AATTGCTCAA | ACATAGCAAA | 2640 |
| AATGTGACAA | ACAGCTTAGA | TAAGTTAATC | TCATCTGTAA | GTGCATTTAC | CTCGTCTAAT | 2700 |
| GATTCGAGAA | ATGTATTAGT | GGCTCCAACT | TCAATGTTGG | ATCAAAGTTT | ATCTTCTCTT | 2760 |
| CAATTTGCTA | GGGGATCTTG | CAACATTGTG | CCTGTGAGCA | TTGTGAGCCG | CAACATTGTG | 2820 |
| TACACCCGCG | CGCAACCTAA | CCAAGACATT | GTGTAGGATC | C | | 2861 |

( 2 ) INFORMATION FOR SEQ ID NO:11:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 3
( D ) OTHER INFORMATION: /note="The amino acid at this location can be either Lys, Asp, Val or Asn."

( i x ) FEATURE:
( A ) NAME/KEY: Modified-site
( B ) LOCATION: 5
( D ) OTHER INFORMATION: /note="The amino acid at this location can be either Lys, Asp, Val or Asn."

( x i ) SEQUENCE DESCRIPTION: SEQ ID NO:11:

Gly Gly Xaa Gly Xaa Asp
1 5